(12) United States Patent
Venn-Watson

(10) Patent No.: US 12,370,166 B2
(45) Date of Patent: Jul. 29, 2025

(54) PENTADECANOYLCARNITINE FOR TREATMENT OF CONDITIONS RELATED TO THE QUALITY OF AGING AND LONGEVITY

(71) Applicant: EPITRACKER, INC., San Diego, CA (US)

(72) Inventor: Stephanie Venn-Watson, San Diego, CA (US)

(73) Assignee: Epitracker, Inc., San Diego, CA (US)

( * ) Notice: Subject to any disclaimer, the term of this patent is extended or adjusted under 35 U.S.C. 154(b) by 0 days.

(21) Appl. No.: 17/816,950

(22) Filed: Aug. 2, 2022

(65) Prior Publication Data

US 2023/0132955 A1 May 4, 2023

Related U.S. Application Data

(60) Provisional application No. 63/340,710, filed on May 11, 2022, provisional application No. 63/275,353, filed on Nov. 3, 2021.

(51) Int. Cl.
| | | |
|---|---|---|
| A61K 31/23 | (2006.01) | |
| A61K 31/20 | (2006.01) | |
| A61P 9/00 | (2006.01) | |
| A61P 11/06 | (2006.01) | |
| A61P 13/12 | (2006.01) | |
| A61P 17/06 | (2006.01) | |
| A61P 25/16 | (2006.01) | |
| A61P 25/24 | (2006.01) | |
| A61P 37/06 | (2006.01) | |
| A61P 37/08 | (2006.01) | |

(52) U.S. Cl.
CPC .............. *A61K 31/23* (2013.01); *A61K 31/20* (2013.01); *A61P 9/00* (2018.01); *A61P 11/06* (2018.01); *A61P 13/12* (2018.01); *A61P 17/06* (2018.01); *A61P 25/16* (2018.01); *A61P 25/24* (2018.01); *A61P 37/06* (2018.01); *A61P 37/08* (2018.01)

(58) Field of Classification Search
CPC ......... A61K 31/23; A61K 31/20; A61P 17/06; A61P 9/00; A61P 11/06; A61P 37/06; A61P 37/08; A61P 13/12; A61P 25/24; A61P 25/16
See application file for complete search history.

(56) References Cited

U.S. PATENT DOCUMENTS

| | | | |
|---|---|---|---|
| 4,252,159 | A | 2/1981 | Maki |
| 4,718,430 | A | 1/1988 | Holzer |
| 4,985,015 | A | 1/1991 | Obermann et al. |
| 5,318,521 | A | 6/1994 | Slettenmark |
| 5,449,688 | A | 9/1995 | Wahl et al. |
| 5,465,728 | A | 11/1995 | Phillips |
| 5,741,816 | A | 4/1998 | Tsujihara et al. |
| 6,214,875 | B1 | 4/2001 | Yang |
| 6,384,252 | B1 | 5/2002 | Pageat |
| 6,441,036 | B1 | 8/2002 | Berge |
| 6,544,541 | B1 | 4/2003 | Zahradka |
| 7,012,053 | B1 | 3/2006 | Barnabas et al. |
| 7,375,135 | B2 | 5/2008 | Najib-Fruchart et al. |

(Continued)

FOREIGN PATENT DOCUMENTS

| | | |
|---|---|---|
| CA | 2337484 A1 | 8/2001 |
| CN | 1939332 A | 4/2007 |

(Continued)

OTHER PUBLICATIONS

Anxiety Disorders. Cleveland Clinic: 2020. my.clevelandclinic.org/health/diseases/ 9536-anxiety-disorders (Year: 2020).*
Staner, Luc. Sleep and Anxiety Disorders. Dialogues in Clinical Neuroscience—vol. 5 . No. 3 . 2003 (Year: 2003).*
Bianchi Current Opinion in Cell Biology 2020, 63:135-143 (Year: 2020).*
https://www.cancer.org/cancer/risk-prevention.html (Year: 2023).*
Adachi et al., "Effect of the glyceride of pentadecanoic acid on energy metabolism in hair follicles". Int J Cosmetic Sci. Jun. 1993;15(3): 125-131.

(Continued)

*Primary Examiner* — Clinton A Brooks
*Assistant Examiner* — Jerica Katlynn Wilson
(74) *Attorney, Agent, or Firm* — Knobbe, Martens, Olson & Bear LLP

(57) ABSTRACT

Administration of pentadecanoylcarnitine or pentadecanoic acid is provided for prevention, management or treatment of aggression, allergies, allergic rhinitis, Alzheimer's disease, anxiety and anxiety disorders, amyotrophic lateral sclerosis, arthritis, asthma, atherosclerosis, attention-deficit hyperactivity disorder, bipolar disorder, brain damage, cancer, cardiovascular disease, cholestatic pruritis, depression, chronic obstructive pulmonary disease (COPD), cocaine abuse, cough, dermatitis, depression, drug-seeking behavior, gastrointestinal disorders, facial erythema associated with rosacea, glaucoma, hepatic diseases, hyperactive bladder, hypersensitivity disorders, hypertension, impulsivity, inflammation, mental disorders and conditions, metabolic disorders, migraines, nasal and sinus congestion, nausea, neuropathic pain with and symptoms of multiple sclerosis, neurological and neuropsychiatric disorders, obesity, obsessive-compulsive disorders, opioid-induced respiratory depression, osteoarthritis, pain, Parkinson disease, pathological gambling, peptic ulcers, schizophrenia, sleep disorders, spinal cord injury, tardive dyskinesia, tics and behavioral problems with Tourette's syndrome; as well as for supporting appetite, cardiovascular health, hematologic health, memory, metabolic health, mood, prolonged REM sleep, renal health, sexuality, sociability and metabolic, hematological, renal, and weight loss.

30 Claims, 1 Drawing Sheet

(56) References Cited

U.S. PATENT DOCUMENTS

| | | |
|---|---|---|
| 7,651,845 B2 | 1/2010 | Doyle et al. |
| 8,030,348 B2 | 10/2011 | Sampalis |
| 8,088,825 B2 | 1/2012 | Berge et al. |
| 8,106,093 B2 | 1/2012 | Roe |
| 8,251,904 B2 | 8/2012 | Zivitz et al. |
| 8,759,558 B2 | 6/2014 | Holmeide et al. |
| 8,827,957 B2 | 9/2014 | Searle et al. |
| 9,282,760 B2 | 3/2016 | Bryhn et al. |
| 9,295,637 B2 | 3/2016 | Perricone |
| 9,561,206 B2 | 2/2017 | Venn-Watson |
| 9,662,306 B2 | 5/2017 | Venn-Watson |
| 9,687,461 B2 | 6/2017 | Venn-Watson |
| 9,707,199 B2 | 7/2017 | Venn-Watson |
| 9,713,600 B2 | 7/2017 | Venn-Watson |
| 10,022,347 B2 | 7/2018 | Venn-Watson |
| 10,111,849 B2 | 10/2018 | Henderson |
| 10,238,618 B2 | 3/2019 | Venn-Watson |
| 10,307,388 B2 | 6/2019 | Venn-Watson |
| 10,449,170 B2 | 10/2019 | Venn-Watson |
| 10,449,171 B2 | 10/2019 | Venn-Watson |
| 10,792,266 B2 | 10/2020 | Venn-Watson et al. |
| 11,116,740 B2 | 9/2021 | Venn-Watson |
| 11,951,088 B2 | 4/2024 | Venn-Watson et al. |
| 11,992,473 B2 | 5/2024 | Venn-Watson |
| 2002/0156351 A1 | 10/2002 | Sagel |
| 2003/0086869 A1 | 5/2003 | Stallings |
| 2003/0203004 A1 | 10/2003 | Kelm et al. |
| 2003/0203042 A1 | 10/2003 | Cook |
| 2006/0154833 A1 | 7/2006 | Katou et al. |
| 2006/0269495 A1 | 11/2006 | Popp et al. |
| 2006/0275294 A1 | 12/2006 | Omoigui |
| 2007/0088170 A1 | 4/2007 | Bryhn et al. |
| 2009/0069331 A1 | 3/2009 | Vallance et al. |
| 2009/0318369 A1 | 12/2009 | Paige et al. |
| 2011/0077301 A1 | 3/2011 | Deminiere et al. |
| 2011/0098358 A1 | 4/2011 | Fujimoto et al. |
| 2011/0182943 A1 | 7/2011 | Kanwar et al. |
| 2011/0190395 A1 | 8/2011 | Holmeide et al. |
| 2011/0190702 A1 | 8/2011 | Stumber |
| 2011/0201558 A1 | 8/2011 | Roe et al. |
| 2012/0071418 A1 | 3/2012 | Copeland et al. |
| 2012/0072236 A1 | 3/2012 | Atkin |
| 2012/0122940 A1 | 5/2012 | Hovland et al. |
| 2013/0053362 A1 | 2/2013 | Castro et al. |
| 2013/0303616 A1 | 11/2013 | Williams et al. |
| 2014/0303228 A1 | 10/2014 | Lawton et al. |
| 2015/0291523 A1 | 10/2015 | Ishikawa et al. |
| 2016/0045533 A1 | 2/2016 | Power et al. |
| 2016/0193170 A1 | 7/2016 | Venn-Watson et al. |
| 2016/0193171 A1 | 7/2016 | Venn-Watson |
| 2016/0193172 A1 | 7/2016 | Venn-Watson |
| 2016/0195558 A1 | 7/2016 | Venn-Watson et al. |
| 2016/0195559 A1 | 7/2016 | Venn-Watson |
| 2016/0324814 A1 | 11/2016 | Venn-Watson |
| 2017/0266144 A1 | 9/2017 | Venn-Watson |
| 2017/0319149 A1 | 11/2017 | Koehler et al. |
| 2018/0148682 A1 | 5/2018 | Ross |
| 2018/0185316 A1 | 7/2018 | Venn-Watson |
| 2018/0311303 A1 | 11/2018 | Maione et al. |
| 2019/0054052 A1 | 2/2019 | Shchepinov |
| 2019/0117607 A1 | 4/2019 | Venn-Watson et al. |
| 2019/0240181 A1 | 8/2019 | Venn-Watson |
| 2019/0358183 A1 | 11/2019 | Venn-Watson |
| 2020/0222351 A1 | 7/2020 | Dhamane et al. |
| 2020/0345676 A1 | 11/2020 | Venn-Watson et al. |
| 2021/0046034 A1 | 2/2021 | Venn-Watson |
| 2021/0052535 A1 | 2/2021 | Venn-Watson |
| 2021/0330734 A1 | 10/2021 | Venn-Watson |
| 2021/0346419 A1 | 11/2021 | Venn-Watson |
| 2021/0386710 A1 | 12/2021 | Venn-Watson |
| 2023/0201153 A1 | 6/2023 | Venn-Watson |
| 2023/0293491 A1 | 9/2023 | Venn-Watson |
| 2023/0381127 A1 | 11/2023 | Venn-Watson |
| 2024/0016773 A1 | 1/2024 | Venn-Watson |
| 2024/0277649 A1 | 8/2024 | Venn-Watson et al. |
| 2024/0307336 A1 | 9/2024 | Venn-Watson |

FOREIGN PATENT DOCUMENTS

| | | | |
|---|---|---|---|
| CN | 102327368 A | 1/2012 | |
| DE | 2615061 | 10/1977 | |
| DE | 102010010666 A1 | 9/2011 | |
| EP | 1000071 A1 | 5/2000 | |
| EP | 1020179 A2 | 7/2000 | |
| EP | 3301090 A1 | 4/2018 | |
| JP | S60172925 | 9/1985 | |
| JP | S61015809 A | 1/1986 | |
| JP | S62012716 | 1/1987 | |
| JP | S63099063 | 4/1988 | |
| JP | H06172168 A | 6/1994 | |
| JP | 2003160486 A | 6/2003 | |
| JP | 2004115438 A | 4/2004 | |
| JP | 2005523331 A | 8/2005 | |
| JP | 2008255022 A | 10/2008 | |
| JP | 2008540393 | 11/2008 | |
| JP | 2010260833 A | 11/2010 | |
| JP | 2011528350 A | 11/2011 | |
| JP | 2014080432 A | 5/2014 | |
| JP | 2015010067 A | 1/2015 | |
| JP | 2016504403 | 2/2016 | |
| JP | 6029668 B2 | 11/2016 | |
| JP | 2017200910 A | 11/2017 | |
| JP | 2017536879 A | 12/2017 | |
| KR | 20170087813 A | 7/2017 | |
| KR | 201701009096 A | 9/2017 | |
| KR | 102087634 B1 | 3/2020 | |
| WO | WO 1996/26647 | 9/1996 | |
| WO | WO 1996/32850 | 10/1996 | |
| WO | WO 1999/001103 | 1/1999 | |
| WO | WO 1999/002485 | 1/1999 | |
| WO | WO 2000/040217 | 7/2000 | |
| WO | WO 2004/057982 | 7/2004 | |
| WO | WO 2004/069240 | 8/2004 | |
| WO | WO 2005/099483 | 10/2005 | |
| WO | WO 2005/120485 | 12/2005 | |
| WO | WO 2006/038063 | 4/2006 | |
| WO | WO 2006/117668 | 11/2006 | |
| WO | WO 2007/002365 | 1/2007 | |
| WO | WO 2007/100435 | 9/2007 | |
| WO | WO 2008/114732 | 9/2008 | |
| WO | WO 2010/123930 | 10/2010 | |
| WO | WO 2012/001336 | 1/2012 | |
| WO | WO 2012/069790 | 5/2012 | |
| WO | WO 2013/007700 | 1/2013 | |
| WO | WO 2014/108573 | 7/2014 | |
| WO | WO 2014/179341 | 11/2014 | |
| WO | WO 2015/110977 | 7/2015 | |
| WO | WO 2015/140545 | 9/2015 | |
| WO | WO 2015/157514 | 10/2015 | |
| WO | WO 2016/111843 | 7/2016 | |
| WO | WO 2017/186928 | 11/2017 | |
| WO | WO 2018/157013 | 8/2018 | |
| WO | WO 2019/212196 A1 | 11/2019 | |
| WO | WO 2019/222254 | 11/2019 | |
| WO | WO 2019/226572 | 11/2019 | |
| WO | WO-2019226572 A1 * | 11/2019 | ........... A23L 33/175 |
| WO | WO 2020/146263 | 7/2020 | |
| WO | WO 2020/154173 | 7/2020 | |

OTHER PUBLICATIONS

Agius et al., "The metformin mechanism on gluconeogenesis and AMPK activation: the metabolite perspective". Int J Mol Sci. May 3, 2020;21(9): 3240 in 19 pages.

Aglago et al., Association between serum phospholipid fatty acid levels and adiposity in Mexican women. J Lipid Res. Jul. 1, 2017;58(7): 1462-1470.

Ali et al., "Recent advances and limitations of mTOR inhibitors in the treatment of cancer". Cancer Cell Int. Dec. 2022;22(1): 284 in 16 pages.

(56) References Cited

OTHER PUBLICATIONS

Ananthakrishnan et al., Inflammatory bowel disease in the elderly is associated with worse outcomes: a national study of hospitalizations. Inflamm Bowel Dis. Feb. 1, 2009;15(2): 182-189.
Anisimov et al., "Metformin slows down aging and extends life span of female SHR mice". Cell Cycle Sep. 1, 2008;7(17): 2769-2773.
Bartzokis et al., Brain ferritin iron may influence age- and gender-related risks of neurodegeneration. Neurobiol Aging. Mar. 1, 2007;28(3): 414-423.
Barzilai et al., "Metformin as a tool to target aging". Cell Metab. Jun. 14, 2016;23(6): 1060-1065.
Baum et al., Drug utilization in the U.S.—1985: Seventh annual review. Rockville, MD: Food and Drug Administration, Center for Drugs and Biologies. Dec. 1986.; TOC in 4 pages.
Beanes et al., Down-regulation of decorin, a transforming growth factor-beta modulator, is associated with scarless fetal wound healing. J Pediatr Surg. Nov. 1, 2001;36(11): 1666-1671.
Berg E.L. Phenotypic chemical biology for predicting safety and efficacy. Drug Disc Today Technol. Mar. 1, 2017;23: 53-60.
Bettcher et al., Increases in pro-inflammatory chemokine, MCP-1, are related to decreases in memory over time. Frontiers in aging neuroscience. Feb. 13, 2019; 11:25.
Bielec et al., Homologies between human and dolphin chromosomes detected by heterologous chromosome painting. Cytogen Genome Res. 1998;81(1): 18-25.
Biong et al., Intake of milk fat, reflected in adipose tissue fatty acids and risk of myocardial infarction: a case-control study. Eur J Clin Nutr. Feb. 2006;60(2): 236-244.
Bishop et al., Heptadecanoic acid is not a key mediator in the prevention of diet-induced hepatic steatosis and insulin resistance in mice. Nutrients Apr. 24, 2023;15(9): 2052 in 14 pages.
Blagosklonny M.V., Aging and immortality: Quasi-programmed senescence and its pharmacologic inhibition. Cell cycle. Sep. 15, 2006;5(18): 2087-2102.
Blagosklonny M.V., Rapamycin for longevity: opinion article. Aging Oct. 15, 2019;11(19): 8048-8067.
Blagosklonny M.V., "Cell senescence, rapamycin and hyperfunction theory of aging". Cell Cycle Jul. 18, 2022;21(14): 1456-1467.
Bridle et al., "Rapamycin inhibits hepatic fibrosis in rats by attenuating multiple profibrogenic pathways". Transplantation Oct. 2009;15(10): 1315-1324.
Browner et al., "The genetics of human longevity". Am J Med. Dec. 1, 2004;117(11): 851-860.
Brydges et al., Metabolomic and inflammatory signatures of symptom dimensions in major depression. Brain, Behavior, and Immunity. May 1, 2022;102: 42-52 (available Aug. 5, 2021).
Budczies et al., "Remodeling of central metabolism in invasive breast cancer compared to normal breast tissue—a GC-TOFMS based metabolomics study". BMC Genomics Dec. 2012;13(1): 334 in 11 pages.
Chaib et al., "Cellular senescence and senolytics: the path to the clinic". Nat Med. Aug. 2022;28(8): 1556-1568.
Chaudhari et al., Increased mitochondrial fusion allows the survival of older animals in diverse C. elegans longevity pathways. Nat Commun. Aug. 3, 2017;8(1): 182 in 16 pages.
Cheng et al., "Metformin's mechanisms in attenuating hallmarks of aging and age-related disease". Aging Dis. Jul. 7, 2022;13(4): 970-986.
Coccia et al., IL-1B mediates chronic intestinal inflammation by promoting the accumulation of IL-17A secreting innate lymphoid cells and CD4+ Th17 cells. J Exp Med. Aug. 27, 2012;209(9): 1595-1609.
Crimmins E.M., "Lifespan and healthspan: past, present, and promise". The Gerontologist Dec. 1, 2015;55(6): 901-911.
De Martinis et al., Allergy and aging: an old/new emerging health issue. Aging and Dis. Apr. 2017;8(2): 162-175.
De Mello et al., "Serum levels of plasmalogens and fatty acid metabolites associate with retinal microangiopathy in participants from the Finnish Diabetes Prevention Study". Nutrients Dec. 14, 2021;13(12): 4452 in.
Deng et al., Cross-talk between mitochondrial fusion and the hippo pathway in controlling cell proliferation during drosophila development. Genetics Aug. 1, 2016; 203(4): 1777-1788.
Devito et al., "Extending human lifespan and longevity: a symposium report". Ann N Y Acad Sci. Jan. 2022;1507(1): 70-83 [publ. online Sep. 8, 2021].
Djousse et al., Serum individual nonesterified fatty acids and risk of heart failure in older adults. Cardiology Feb. 25, 2021;146(3): 351-358.
Dornan et al., Odd chain fatty acids and odd chain phenolic lipids (alkylresorcinols) are essential for diet. J Am Chem Soc. Aug. 2021;98(8): 813-824.
Dugan et al., Inflammaging as a target for healthy ageing. Age and Ageing. Feb. 1, 2023;52(2): afac328 in 15 Pages.
Ediriweera et al., "Odd-chain fatty acids as novel histone deacetylase 6 HDAC6) inhibitors". Biochimie Jul. 11, 2021;186: 147-156.
Ehninger et al., "Longevity, aging and rapamycin". Cell Mol Life Sci. Nov. 2014;71(22): 4325-4346.
Farage et al., Characteristics of the aging skin. Adv Wound Care. Feb. 1, 2013;2(1): 5-10.
Fonteh et al., Human cerebrospinal fluid fatty acid levels differ between supernatant fluid brain-derived nanoparticle fractions, and are altered in Alzheimer's disease. PloS One. Jun. 23, 2014;9(6): e100519 in 14 pages.
Franceschi et al., Chronic Inflammation (Inflammaging) and Its Potential Contribution to Age-Associated Diseases. J Gerontol. Jun. 2014; 69(suppl 1): S4-S9.
Fu et al., Oleylethanolamide regulates feeding and body weight through activation of the nuclear receptor PPAR-α. Nature. Sep. 4, 2003;425(6953): 90-93.
Fu et al., Pentadecanoic acid promotes basal and insulin-stimulated glucose uptake in C2C12 myotubes. Food Nutr Res. 2021;65: 4527 in 9 pages.
Galdiero et al., Pentadecanoic acid against Candida albicans-Klebsiella pneumoniae biofilm: Towards the development of an anti-biofilm coating to prevent polymicrobial infections. Res Microbiology. Nov. 1, 2021;172(7-8): 103880 in 11 pages.
Garay R.P., "Investigational drugs and nutrients for human longevity. Recent clinical trials registered in ClinicalTrials.gov and clinicaltrialsregister.eu". Expert Opin Investig Drugs Jul. 3, 2021;30(7): 749-758.
Gibson et al., Cooperative care. The time has come. JONA: J Nurs Admin. Mar. 1, 1987;17(3): 19-21.
Giulani A., The application of principal component analysis to drug discovery and biomedical data. Drug Disc Today. Jul. 1, 2017;22(7): 1069-1076.
Gonzalez-Freire et al., "The road ahead for health and lifespan interventions". Ageing Res Rev. May 1, 2020;59:101037 in 46 pages.
Gosmanova et al., "Effect of metformin containing antidiabetic regimens on all-cause mortality in veterans with type 2 diabetes mellitus". Am J Med Sci. Sep. 1, 2008;336(3): 241-247.
Gregg et al., Trends in lifetime risk and years of life lost due to diabetes in the USA, 1985-2011: A modelling study. Lancet Diab Endocrinol. Nov. 1, 2014;2(22): 867-874.
Groarke et al., "Aging and hematopoiesis". Clin Geriatr Med. Aug. 1, 2019;35(3): 285-293.
Gunn-Moore et al., Alzheimer's disease in humans and other animals: a consequence of postreproductive life span and longevity rather than aging. Alzheimer's & Dementia. Feb. 1, 2018;14(2): 195-204.
Harrison et al., "Acarbose, 17—α-estradiol, and nordihydroguaiaretic acid extend mouse lifespan preferentially in males". Aging Cell Apr. 2014;13(2): 273-282.
Hayaishi O., Molecular mechanisms of sleep-wake regulation: roles of prostaglandins D2 and E2. FASEB J. Aug. 1991;5(11): 2575-2581.

(56) References Cited

OTHER PUBLICATIONS

Hirose et al., Age-associated increases in heme oxygenase-1 and ferritin immunoreactivity in the autopsied brain. Legal Med. Mar. 1, 2003;5: S360-366.
Hori et al., "Serum sphingomyelin species profile is altered in hematologic malignancies". Clin Chim Acta Mar. 1, 2021;514: 29-33.
Huang et al., "Circulating saturated fatty acids and incident type 2 diabetes: A systematic review and meta-analysis". Nutrients May 1, 2019;11(5): 998 in 20 pages.
Hulbert A.J. "On the importance of fatty acid composition of membranes for aging". J Theor Biol. May 21, 2005;234(2): 277-288.
Imamura et al., "Fatty acid biomarkers of dairy fat consumption and incidence of type 2 diabetes: A pooled analysis of prospective cohort studies". PLoS Med. Oct. 10, 2018;15(10): e1002670 in 18 pages.
Iwakura et al., The roles of IL-17A in inflammatory immune responses and host defense against pathogens. Immun Rev. Dec. 2008;226(1): 57-79.
Jee et al., "Clinical relevance of glycerophospholipid, sphingomyelin and glutathione metabolism in thepathogenesis of pharyngolaryngeal cancer in smokers: the Korean Cancer Prevention Study—II". Metabolomics Nov. 2016;12: 164 in 12 Pages.
Jiao et al., Circulating fatty acids associated with advanced liver fibrosis and hepatocellular carcinoma in South Texas Hispanics. Cancer Epide., Biomark & Prev. Sep. 1, 2021;30(9): 1643-1651.
Jimenez-Cepeda et al., Dietary intake of fatty acids and its relationship with FEV1/FVC in patients with chronic obstructive pulmonary disease. Clin Nutr. ESPEN. Feb. 1, 2019;29: 92-96.
Jing et al., Metformin improves obesity-associated inflammation by altering macrophages polarization. Mol Cell Endocrin. Feb. 5, 2018;461: 256-264.
Justice et al., "Frameworks for proof-of-concept clinical trials of interventions that target fundamental aging processes". J Gerontol A Biol Sci Med Sci. Nov. 1, 2016;71(11): 1415-1423.
Justice et al., "Development of clinical trials to extend healthy lifespan". Cardiovasc Endocrinol Metab. Dec. 2018;7(4): 80-83.
Kaestner et al., "The potential of erythrocytes as cellular aging models". Cell Death Differ. Sep. 2017;24(9): 1475-1477.
Kaikkonen et al., "Associations of serum fatty acid proportions with obesity, insulin resistance, blood pressure and fatty liver: the cardiovascular risk in young Finns study". J Nutr Apr. 2021;151(4): 970-978.
Kaur et al., "Essential fatty acids as functional components of foods—a review". J Food Sci Technol. Oct. 2014;51: 2289-2303.
Khaw et al., Plasma phospholipid fatty acid concentration and incident coronary heart disease in men and women: the EPIC-Norfolk prospective study. PLoS Med. Jul. 3, 2012;9(7): e1001255 in 12 pages.
Khwaja et al., "Efficacy and Cardiovascular Safety of Alpha Glucosidase Inhibitors". Drug Safety Jul. 1, 2021;16(2): 122-128.
Kirkham T.C., Endocannabinoids in the regulation of appetite and body weight. Behav Pharmacol. Sep. 1, 2005;16(5-6): 297-313.
Kobayashi et al., New directions in cancer and aging: State of the science and recommendations to improve the quality of evidence on the intersection of aging with cancer control. Cancer. May 1, 2022;128(9): 1730-1737.
Kritchevsky et al., "Testing the geroscience hypothesis: early days". J Gerontol A Biol Sci Med Sci. Jan. 1, 2020;75(1): 99-101 [publ. online Dec. 13, 2019].
Kruchinina et al., "Erythrocyte membrane fatty acids as the potential biomarkers for detection of early-stage and progression of colorectal cancer". Ann Oncol. Jun. 1, 2018;29(Suppl 5): v52.
Kurotani et al., "Even- and odd-chain saturated fatty acids in serum phospholipids are differentially associated with adipokines". PLoS One May 26, 2017;12(5): e0178192 in 14 pages.
Lankinen et al., "Plasma fatty acids as predictors of glycaemia and type 2 diabetes". Diabetologia Nov. 2015;58: 2533-2544.
Lee et al., A current review of molecular mechanisms regarding osteoarthritis and pain. Gene Sep. 25, 2013;527(2): 440-447.
Li et al., Design, synthesis and antitumor activity study of a gemcitabine prodrug conjugated with a HDAC6 inhibitor. Bioorg Med Chem Lttrs. Sep. 15, 2022;72: 128881 in 6 pages.
Li et al., "Extraction, purification, and elucidation of six ginkgo homologs from Ginkgo biloba sarcotesta and evaluation of their anticancer activities". Molecules Nov. 11, 2022;27(22): 7777 in 15 pages.
Liang et al., "Biomarkers of dairy fat intake and risk of cardiovascular disease: a systematic review and meta analysis of prospective studies". Crit Rev Food Sci Nutr. May 3, 2018;58(7): 1122-1130.
Liechty K.W., Diminished interleukin-8 (IL-8) production in the fetal wound healing response. J Surg Res. Jun. 1, 1998;77(1): 80-84.
Lim et al., The global impact of hepatic fibrosis and end-stage liver disease. Clinics in Liver Dis. Nov. 1, 2008;12(4): 733-746.
Lin et al., Effects of the mTOR inhibitor Rapamycin on monocyte-secreted chemokines. BMC Immunol. Dec. 2014;15(1): 1-9.
Lin et al., Efficacy and safety of topical mechanistic target of rapamycin inhibitors for facialangiofibromas in patients with tuberous sclerosis complex: a systematic review and network meta-analysis. Biomedicines Mar. 31, 2022;10(4): 826 in 13 pages.
Lipschitz et al., The anemia of senescence. Am J Hematol. Aug. 1981;11(1): 47-54.
Longo et al., "Interventions to slow aging in humans: are we ready?" Aging Cell Aug. 2015;14(4): 497-510.
Lyu et al., Association between anemia and 3-year all-cause mortality among oldest old people in longevity areas in China. Zhonghua Liuxingbingxue Zazhi. Jul. 1, 2015;36(7): 682-686.
Manca et al., Circulating fatty acids and endocannabinoide-related mediator profiles associated to human longevity. GeroScience. Aug. 2021;43(4): 1783-1798.
Martin-Montalvo et al., "Metformin improves healthspan and lifespan in mice". Nat Commun. Jul. 30, 2013;4(1): 2192 in 23 pages.
Matthan et al., Spillover effects of a family-based childhood weight-management intervention on parent nutrient biomarkers and cardiometabolic risk factors. Curr Dev Nutrition Feb. 2022;6(2): 152 in 41 pages.
McArtor et al., Extending multivariate distance matrix regression with an effect size measure and the asymptotic null distribution of the test statistic. Psychometrika. Dec. 2017;82: 1052-1077.
Millner et al., "Lipid players of cellular senescence". Metabolites Aug. 21, 2020;10(9): 399 in 17 pages.
Monjan et al., Incidence of chronic insomnia associated with medical and psychosocial factors: an epidemiologic study among older persons. Sleep Res. Jun. 1996;25: 108.
Moskalev et al., "Targeting aging mechanisms: pharmacological perspectives". Trends Endocrinol Metab. Apr. 1, 2022;33:266-280.
Murphy et al., The origin of human chromosome 1 and its homologs in placental mammals. Genome Res. Aug. 1, 2003;13(8): 1880-1888.
Nadon et al., "NIA interventions testing program: investigating putative aging intervention agents in a genetically heterogeneous mouse model". EBioMedicine Jul. 1, 2017;21: 3-4.
Niedernhofer et al., Molecular pathology endpoints useful for aging studies. Age Res Rev. May 1, 2017;35: 241-249.
Novelle et al., Metformin: A hopeful promise in aging research. CSH Persp Med. Mar. 1, 2016;6(3): a025932 in 13 pages.
Pamplona et al., Increased oxidation, glycoxidation, and lipoxidation of brain proteins in prion disease. Free Radical Biol Med. Oct. 15, 2008;45(8): 1159-1166.
Paolisso et al., Low insulin resistance and preserved B-cell function contribute to human longevity but are not associated with TH-INS genes. Exp Gerontol. Dec. 1, 2001; 37(1):147-156.
Patel et al., Prevalence and impact of pain among older adults in the United States: Findings from the 2011 National Health and Aging Trends Study. Pain Dec. 1, 2013;154(12): 2649-2657.
Perreault et al., PPARδ agonism for the treatment of obesity and associated disorders: Challenges and opportunities. PPAR Res. 2008;2008: Article ID125387; in 9 pages.
Perrone et al., Selective COX01 inhibition: A therapeutic target to be reconsidered. Curr Med Chem. Nov. 1, 2010;17(32): 3769-3805.
Qi et al., "High-resolution metabolomic biomarkers for lung cancer diagnosis and prognosis". Sci Rep. Jun. 3, 2021;11(1): 11805 in 10 pages.

(56) References Cited

OTHER PUBLICATIONS

Ricciardelli et al., Pentadecanal and pentadecanoic acid coatings reduce biofilm formation of *Staphylococcus epidermidis* on PDMS. Patho Dis. Apr. 2020;78(3): ftaa012 in 8 pages.
Roh et al., A clinical study of pentadecanoic glyceride (LHOP) on male pattern alopecia. J Korean Soc Clin Pharma Thera. Dec. 1, 1998;6(2): 199-206.
Salive et al., "Anemia and hemoglobin levels in older persons: relationship with age, gender, and health status". J Am Geriat Soc. May 1992:40(5): 489-496.
Salvatore et al., "Metformin: an old drug against old age and associated morbidities". Diab Res Clin Prac. Feb. 1, 2020;160: 108025 in 11 pages.
Santaren et al., "Serum pentadecanoic acid (15:0), a short-term marker of dairy food intake, is inversely associated with incident type 2 diabetes and its underlying disorders". Am J Clin Nutr. Dec. 1, 2014;100(6): 1532-1540.
Sawh et al., Dairy fat intake, plasma pentadecanoic acid, and plasma iso-heptadecanoic acid are inversely associated with liver fat in children. J Ped Gastroent Nutr. Apr. 4, 2021;72(4): e90 in 18 pages.
Schork et al., "Does modulation of an epigenetic clock define a geroprotector?" Adv Geriatr Med Res. Mar. 29, 2022;4(1): e220002 in 11 pages.
Sgnoc et al., Age-related aspects of cutaneous wound healing: a mini review. Gerontol. 2013;59(2): 159-164.
Shamburek et al., Disorders of the digestive system in the elderly. New Engl J Med. Feb. 15, 1990;322(7): 438-443.
Singh et al., MCP-1: Function, regulation and involvement in disease. Int Immunopharm. Dec. 1, 2021;101: 107598 in 9 pages.
Smedman et al., "Pentadecanoic acid in serum as a marker of intake of milk fat: relations between intake of milk fat and metabolic risk factors". Am J Clin Nutr. Jan. 1, 1999;69(1): 22-29.
Smith et al., "Changes in the gut microbiome and fermentation products concurrent with enhanced longevity in acarbose-treated mice". BMC Microbiol. Dec. 2019;19(1): 1-6.
Soboleva et al., "Fatty acids of the lipid fraction of erythrocyte membranes and intensity of lipid peroxidation in iron deficiency". Bull Exp Biol Med. Jun. 1994;117: 600-603.
Sorrenti et al., "Immunomodulatory and antiaging mechanisms of resveratrol, rapamycin, and metformin: focus on mTOR and AMPK signaling networks". Pharmaceuticals Jul. 23, 2022;15(8): 912 in 20 pages.
Soukas et al., "Metformin as anti-aging therapy: is it for everyone?" Trends Endocrinol Metab. Oct. 1, 2019;30(10): 745-755.
To et al., "Pentadecanoic acid, an odd-chain fatty acid, suppresses the stemness of MCF-7/SC humanbreast cancer stem-like cells through JAK2/STAT3 signaling". Nutrients Jun. 3, 2020;12(6): 1663 in 20 pages.
To et al., "Effects of combined pentadecanoic acid and tamoxifen treatment on tamoxifen resistance in MCF-7/SC breast cancer cell". Int J Mol Sci. Sep. 26, 2022;23(19): 11340 in 20 pages.
Tsoukalas et al., Application of metabolomics Part II: Focus on fatty acids and their metabolites in healthy adults. Int J Mol Med. Jan. 1, 2019;43(1): 233-242.
Vaarhorst et al., Lipid metabolism in long-lived families: the Leiden Longevity Study. Age. Jun. 2011;33(2): 219-227.
Venn-Watson et al., "Modified fish diet shifted serum metabolome and alleviated chronic anemia in bottlenose dolphins (*Tursiops truncatus*): Potential role of odd-chain saturated fatty acids". PLoS One Apr. 7, 2020;15(4): e0230769 (2020).
Venn-Watson et al., Efficacy of dietary odd-chain saturated fatty acid pentadecanoic acid parallels broad associated health benefits in humans: could it be essential?. Scientific Rep. May 18, 2020;10(1): 1-4.
Venn-Watson et al., A 25-y longitudinal dolphin cohort supports that long-lived individuals in same environment exhibit variation in aging rates. PNAS Aug. 25, 2020;117(34): 20950-20958.
Venn-Watson et al., "Broader and safer clinically-relevant activities of pentadecanoic acid compared to omega-3: evaluation of an emerging essential fatty acid across twelve primary human cell-based disease systems". PLoS ONE May 26, 2022;17(5): e0268778 in 17 pages.
Venn-Watson et al., Pentadecanoylcarnitine is a newly discovered endocannabinoid with pleiotropicactivities relevant to supporting physical and mental health. Sci Rep. Aug. 23, 2022;12(1): 13717 in 11 pages.
Vézina et al., "Rapamycin (AY-22, 989), a new antifungal antibiotic"—Part I. J Antibio. 1975;28(10): 721-726.
Vitiello M.V., Sleep disorders and aging: understanding the causes. J Gerontol. 1997 Jul. 1, 1997;52(4): M189-M191.
Wagner et al., Combined treatment with exercise training and acarbose improves metabolic control and cardiovascular risk factor profile in subjects with mild type 2 diabetes. Diabetes Care Jul. 1, 2006;29(7): 1471-1477.
Wang et al., Peroxisome-proliferator-activated receptor δ activates fat metabolism to prevent obesity. Cell. Apr. 18, 2003;113(2): 159-170.
Warensjö et al., "Estimated intake of milk fat is negatively associated with cardiovascular risk factors and does not increase the risk of a first myocardial infarction. A prospective case-control study". Br J Nutr. Apr. 2004;91(4): 635-642.
Webster et al., "Target of rapamycin inhibitors (sirolimus and everolimus) for primaryimmunosuppression of kidney transplant recipients: a systemic review and meta-analysis of randomized trials". Transplantation May 15, 2006;81(9): 1234-1248.
Wolf et al., "The MalR type regulator AcrC is a transcriptional repressor of acarbose biosynthetic genes in *Actinoplanes* sp. SE50/110". BMC Genomics Dec. 2017;18(1): 1-4.
Wu et al., "Extension of life span by acarbose: is it mediated by the gut microbiota"? Aging Dis. Jul. 7, 2022;13(4): 1005-1014.
Xu et al., "Rapamycin for lymphangioleiomyomatosis: optimal timing and optimal dosage". Thorax Apr. 1, 2018;73(4): 308-310.
Xu et al., Cross-sectional associations of adipokines and abdominal fat distribution with aging in men. The Aging Male. Dec. 4, 2020;23(5): 1576-1582.
Vasto et al., Inflammatory networks in ageing, age-related diseases, and longevity. Mech Ageing and Dev. Jan. 1, 2007;128(1): 83-91.
Ye et al., A pharmacological network for lifespan extension in Caenorhabditis elegans. Aging cell. Apr. 2014;13(2): 206-215.
Yoo et al., "An overview of rapamycin: from discovery to future perspectives". J Indus Microbiol Biotech. May 1, 2017;44(4-5): 537-553.
Yoo et al., Fatty acids in non-alcoholic steatohepatitis: : Focus on pentadecanoic acid. PloS One. Dec. 15, 2017;12(12): e0189965 in 15 pages.
Yousefzadeh et al., Circulating levels of monocyte chemoattractant protein-1 as a potential measure of biological age in mice and frailty in humans. Aging cell. Apr. 2018;17(2): e12706 in 7 pages.
Zapala et al., Multivariate regression analysis of distance matrices for testing associations between gene expression patterns and related variables. Proc Nat Acad Scie. Dec. 19, 2006;103(51): 19430-19435.
Zapala et al., Statistical properties of multivariate distance matrix regression for high-dimensional data analysis. Front Genetics. Sep. 27, 2012;3: 190 in 10 pages.
Zhai et al., Anemia status and its relevant factors among elderly people aged above 80 years old in longevity areas in China. Chinese J of Prev Med. Feb. 1, 2010;44(2):115-118.
Zheng et al., Association between plasma phospholipid saturated fatty acids and metabolic markers of lipid, hepatic, inflammation and glycaemic pathways in eight European countries: a cross-sectional analysis in the EPIC—Interact study. BMC Med. Dec. 2017;15(1): 203 in 13 pages.
Zheng et al., Changes in plasma phospholipid fatty acid profiles over 13 years and correlates of change: European Prospective Investigation into Cancer and Nutrition-Norfolk Study. Am J Clin Nutr. Jun. 1, 2019;109(6): 1527-1534.
Zhu et al., Synthesis and inhibitory activities against colon cancer cell growth and proteasome of alkylresorcinols. J Agric Food Chem. Sep. 5, 2012;60(35): 8624-8631.

(56) References Cited

OTHER PUBLICATIONS

Zhu et al., A prospective study and longitudinal study of plasma phospholipid saturated fatty acid profile in relation to cardiometabolic markers and the risk of gestational diabetes. Am J Clin Nutr. Jun. 1, 2018;107(6): 1017-1026.
Zhuang et al., Saturated fatty acid intake is associated with total mortality in a nationwide cohort study. J Nutr. Jan. 1, 2019;149(1): 68-77.
Greenberg et al., "Omega-3 fatty acid supplementation during pregnancy". Rev Obstet Gynecol. 2008;1(4): 162-169.
Mihalik et al., "Increased levels of plasma acylcarnitines in obesity and type 2 diabetes and identification of a marker of glucolipotoxicity". Obesity Sep. 2010;18(9): 1695-1700.
Venn-Watson et al., Physiology of aging among healthy, older bottlenose dolphins (*Tursiops truncatus*): comparisons with aging humans. J Comp Phys B. 2011, 181(15):667-680.
Venn-Watson et al., "Hemochromatosis and fatty liver disease: building evidence for insulin resistance in bottlenose dolphins (*Tursiops truncatus*)." J Zoo Wildl Med. 2012, 43(3 Suppl):S35-S47.
Venn-Watson et al., "Blood-Based Indicators of Insulin Resistance and Metabolic Syndrome in Bottlenose Dolphins (*Tursiops truncatus*)", Front Endocrinol (Lausanne) 2013, 4:136 in 8 pages.
Venn-Watson et al., "Increased Dietary Intake of Saturated Fatty Acid Heptadecanoic Acid (C17:0) Associated with Decreasing Ferritin and Alleviated Metabolic Syndrome in Dolphins", PLoS ONE, 2016, 10(7):e0132117 in 17 pages.
International Search Report and Written Opinion dated Nov. 17, 2022 for PCT/US2022/039166.
Abdullah et al., "Recommended dairy product intake modulates circulating fatty acid profile in healthy adults: a multi-centre crossover study", Br J Nutr. 113(3):435-444.
Adams et al., "Hemochronatosis and iron-overload screening in a racially diverse population." New Engl J Med. 2005, 352(17):1769-1778.
Adams et al., "A diagnostic approach to hyperferritinemia with a non-elevated transferrin saturation", J Hepatol. 2011, 55(2):453-458.
Ahmad et al., "Interaction of Osteopontin with IL-18 in Obese Individuals: Implications for Insulin Resistance". PLoS ONE 2013, 8(5):e63944 in 9 pages.
Akbar et al., Alterations in Hepatic FGF21, Co-Regulated Genes, and Upstream Metabolic Genes in Response to Nutrition, Ketosis and Inflammation in Peripartal Holstein Cows, PLoS One 2015, 10(10):e0139963 in 16 pages.
Akhter, J. MD; Asthma-cure, 2017, https://www.scientificamerican.com/article/can-asthma-be-cured-what/ in 7 pages.
Aksenov et al., "Metabolite Content Profiling of Bottlenose Dolphin Exhaled Breath", Anal Chem 2014, 86(21):10616-10624.
Aleshin et al. Peroxisome proliferator-activated receptor (PPAR)β/δ, a possible nexus of PPARα- and PPARγ-dependent molecular pathways in neurodegenerative diseases: review and novel hypotheses. Neurochem Int. (2013) 63:322-330.
Altamura et al., "Iron toxicity in diseases of aging: Alzheimer's disease, Parkinson's disease and atherosclerosis." J Alzheimer's Dis. 2009, 16(4):879-895.
Anderson et al., "Cholesterol and mortality: 30 years of follow-up from the Framingham Study." JAMA (1987) 257(16):2176-2180.
Angulo et al., "Liver Fibrosis, but no Other Histologic Features, Associates with Long-term Outcomes of Patients With Nonalcoholic Fatty Liver Disease". Gastroenterology. 2015, 149(2):389-397.
Ballatore et al., "Carboxylic Acid (Bio) Isosteres in Drug Design". ChemMedChem. 2013, 8(3):385-395.
Barba et al., Alzheimer's disease beyond the genomic era: nuclear magnetic resonance (NMR) spectroscopy-based metabolomics. J Cell Mol Med. 2008. 12(5a): 1477-1485.
Barcellini et al., "Clinical Applications of Hemolytic Markers in the Differential Diagnosis and Management of Hemolytic Anemia". Disease Markers (2015) Article ID 635670 in 7 pages.

Barish et al., "PPARδ: a dagger in the heart of the metabolic syndrome", J Clin Invest. (2006) 116(3): 590-597.
Barros et al., "Prey and feeding patterns of resident bottlenose dolphins (*Tursiops truncatus*) in Sarasota Bay, Florida", J Mammal. 1998, 79:1045-1059.
Bartke et al., "Bioactive sphingolipids: metabolism and function". J Lipid Res. (2009) 50(Suppl): S91-S96.
Batista et al., "Structural Insights into Human Peroxisome Proliferator Activated Receptor Delta (PPAR-Delta) Selective Ligand Binding", PLoS ONE. 2012, 7(5):e33643 in 7 pages.
Beaton et al., "Treatment of Hyperferritinemia", Ann Hepatol. 2012, 11(3):294-300.
Benatar et al., "The effects of changing dairy intake on trans and saturated fatty acid levels—results from a randomized controlled study". Nutr J. 2014, 13:32 in 10 pages.
Berens-Mccabe et al., "Prey selection in a resident common bottlenose dolphin (*Tursiops truncatus*) community in Sarasota Bay, Florida", Marine Biol. 2010, 157:931-942.
Bettcher et al., "MCP-1 and eotaxin-1 selectively and negatively associate with memory in MCI and Alzheimer's disease dementia phenotypes", Alzheimers Dement (Amst). 2016, 3:91-97.
Bhargava et al., "Metabolic alterations in multiple sclerosis and the impact of vitamin D supplementation", JCI Insight. 2017, 2(19): 1-13.
Bialek et al., "Fatty acid composition and oxidative characteristics of novel edible oils in Poland". CyTA—Journal of Food. Jan. 2, 2017;15(1): 1-8; (published online Jul. 13, 2016).
Bogdanov et al., "Metabolomic profiling to develop blood biomarkers for Parkinson's disease", Brain 2008. 131(2): 389-396.
Bonomo et al., "Iron overload potentiates diet-induced hypercholesterolemia and reduces liver PPAR-α expression in hamsters". J Biochem Mol Toxicol. (2012) 26(6): 224-229.
Borodina et al., "The biology of ergothioneine, an antioxidant nutraceutical". Nutri Res Reviews (2020) 33: 190-217.
Bossù et al., "Interleukin-18 produced by peripheral blood cells is increased in Alzheimer's disease and correlates with cognitive impairment". Brain Behav Immun. 2008, 22(4):487-492.
Calder et al., "n-3 polyunsaturated fatty acids, inflammation, and inflammatory diseases." Am J Clin Nutr. 2006, 83(6 suppl):1505S-1519S.
Calder P.C., "Long-chain polyunsaturated fatty acids and inflammation", Scandinavian J Food Nutr. 2006, 50(S2):54-61.
Camaschella C., "Iron-Deficiency Anemia", New Engl J Med. (2015) 372(19):1832-1843.
CAS Database Accession No. 1989:205056; "Relationship between structure and anticonvulsant activities of 2-substituted 3-pyrazolidinones". Du et al., Jun. 10, 1989; 2 pages.
Cater et al., "Behenic acid is a cholesterol-raising saturated fatty acid in humans." Am J Clin Nutr. 2001, 73(1):41-44.
Chebib et al., "Guanidino acids act as ρ1 GABAC receptor antagonists". Neurochem Res. Apr. 23, 2009; 34(10): 1704-1711.
Cheng et al., "Distinct Metabolomic Signatures are Associated with Longevity in Humans.", Nat Commun. 2015, 6:6791 in 22 pages.
Chiba et al., Topical application of PPARα (but not β/δ or γ) suppresses atopic dermatitis in NC/Nga mice. Allergy (2012) 67: 936-942.
Choi et al., "Dairy consumption and risk of type 2 diabetes mellitus in men: a prospective study". Arch Intern Med. 2005, 165(9):997-1003.
Choi et al., The nuclear receptor PPARs as important regulators of T-cell functions and autoimmune diseases. Mol Cell. (2012) 33(3): 217-222.
Colegrove K., Histomorphology of the bottlenose dolphin (*Tursiops truncatus*) pancreas and association of increasing islet ß-cell size with chronic hypercholesterolemia. Gen Comp Endocrinol. 2015, 214:17-23.
Collino et al., "Metabolic Signatures of Extreme Longevity in Northern Italian Centenarians Reveal a Complex Remodeling of Lipids, Amino Acids, and Gut Microbiota Metabolism". PLoS ONE. 2013, 8(3):e56564.
Cordaro et al., "2-Pentadecyl-2-Oxazoline reduces neuroinflammatory environment in the MPTP Model of Parkinson Disease". Mol Neurobiol. Dec. 2018;55(12): 9251-9266.

(56) References Cited

OTHER PUBLICATIONS

Corso et al., Corso et al., "Serum Amino Acid Profiles in Normal Subjects and in Patients with or at Risk of Alzheimer Dementia", Dement Geriatr Cogn Disord Extra. 2017, 7(1):143-159.
Craik J., GLUT-1 mediation of rapid glucose transport in dolphin (*Tursiops truncatus*) red blood cells. Am J Physiol. 1998, 274(1 Pt 2):R112-R119.
Croes et al., Formation of a 2-methyl-branched fatty aldehyde during peroxisomal alpha-oxidation. FEBS Lett. 1997, 412(3):643. 645.
Cronet et al., "Structure of the PPARα and -γ Ligand Binding Domain in Complex with AZ 242; Ligand Selectivity and Agonist Activation in the PPAR Family", Structure. 2001, 9(8):699-706.
Crossno et al., "Rosiglitazone Attenuates Hypoxia-induced Pulmonary Arterial Remodeling". Am J Physiol Lung Cell Mol Physiol. Apr. 2007;292(4): L885-L897.
Cusi et al., "Long-Term Pioglitazone Treatment for Patients With Nonalcoholic Steatohepatitis and Prediabetes or Type 2 Diabetes Mellitus: A Randomized Trial". Ann Intern Med. 2016, 165(5):305-315.
Daak et al., "Effect of omega-3 (n-3) fatty acid supplementation in patients with sickle cell anemia: randomized, double-blind, placebo-controlled trial". Am J Clin Nutr. 2013, 97(1):37-44.
Das Undurti N., "Arachidonic acid in health and disease with focus on hypertension and diabetes mellitus: A review", J Adv Res. 2018, 11:43-55.
Database WPI, "Pentadecanoic acid compound", Clarivate Analytics, AN: 2017-637713, Clarivate Analytics, dated: Jul. 2017; 2 pages.
Database WPI, "Immunosuppressive agent . . . ", AN: 1994-238645, Clarivate Analytics, dated: 1994; 2 pages.
Database WPI, "An effective Saururus chinensisrhizome part . . . ", AN: 2012-B90946, Clarivate Analytics, dated: 2012; 2 pages.
Database WPI, "An anti-aging composition . . . ", AN: 2004-310751, Clarivate Analytics, dated: 2004; 2 pages.
Diehl et al., "Cause, Pathogenesis, and Treatment of Nonalcoholic Steatohepatitis". N Engl J Med. 2017, 377(21):2063-2072.
Di Paolo et al., "Linking Lipids to Alzheimer's Disease: Cholesterol and Beyond", Nat Rev Neurosci. 2011, 12(5):284-296.
Dongiovanni et al., "Iron in fatty liver and in the metabolic syndrome: a promising therapeutic target". J Hepatol. 2011, 55:920-932.
Dursun et al., 2015, The interleukin 1 alpha, interleukin 1 beta, interleukin 6 and alpha-2-macroglobulin serum levels in patients with early or late onset Alzheimer's disease, mild cognitive impairment or Parkinson's disease. J Neuroinflammunol. 2015, 283: 50-57.
Durzan D.J., Arginine, scurvy and Cartier's "tree of life". J Ethnobio Ethnomed. 2009. 5(1): 1-16.
Ekstedt et al., "Fibrosis stage is the strongest predictor for disease-specific mortality in NAFLD after up to 33 years of follow-up." Hepatology. 2015; 61(5): 1547-1554.
Ellervik et al., "Prevalence of hereditary haemochromatosis in late-onset type 1 diabetes mellitus: a retrospective study", Lancet 2001, 358(9291):1405-1409.
Evans et al., "NAD+ metabolite levels as a function of vitamins and calorie restriction: evidence for different mechanisms of longevity." BMC Chem Biol. 2010, 10:2 in 10 pages.
Fargion et al., "Hyperferritinemia, iron overload, and multiple metabolic alterations identify patients at risk for nonalcoholic steatohepatitis". Am J Gastroenterol. 2001, 96(8):2448-2455.
Favé et al., "Physicochemical properties of lipids: new strategies to manage fatty acid bioavailability". Cell Mol Biol. 2004, 50(7):815-831.
FDA Guidance for Industry. "Estimating the maximum safe starting dose in initial clinical trials for therapeutics in adult healthy volunteers." U.S. Food and Drug Administration, Jul. 2005 in 30 pages.
FDA (2017) FDA drug safety communication: FDA warns about serious liver injury with Ocaliva (obeticholic acid) for rare chronic liver disease. Accessed Dec. 5, 2017 https://www.fda.gov/Drugs/DrugSafety/ucm576656.htm in 4 pages.
Fernandes et al., "Relationship between Acute Phase Proteins and Serum Fatty Acid Composition in Morbidly Obese Patients", Dis Markers 2013, 35(2):104-112.
Forman et al., "Hypolipidemic drugs, polyunsaturated fatty acids, and eicosanoids are ligands for peroxisome proliferator-activated receptors α and δ", Proc Natl Acad Sci U.S.A., 1997, 94(9):4312-4317.
Forouhi et al., "Differences in the Prospective Association Between Individual Plasma PhospholipidSaturated Fatty Acids and Incident Type 2 Diabetes: The EPIC-InterAct Case-Cohort Study", Lancet Diabetes Endocrinal, 2014, 2:810-818.
Fujiwara et al., "Biology of Heme in mammalian Erythroid Cells and Related Disorders". BioMed Res Int'l. (2015) Article ID 278536 in 9 pages.
Gabrielsen et al., "Adipocyte iron regulates adiponectin and insulin sensitivity". J Clin Invest. 2012, 122(10):3529-3540.
Gao et al., "In vitro evaluation of dual agonists for PPARΓ/β from the flower of Edgeworthia gardneri (wall.) Meisn". J Ethnopharma . . . Mar. 13, 2015;162: 14-19.
Ghannadi et al., "An Investigation of the Analgesic and Anti-Inflammatory Effects of Nigella sativa Seed Polyphenols", J Med Food. 2005, 8(4): 488-493.
Gibson RA., "Australian fish—An excellent source of both arachidonic acid and ω-3 polyunsaturated fatty acids", Lipids 1983, 18(11):743-752.
Giunta et al., "Inflammaging as a prodrome to Alzheimer's disease", J Neuroinflammation 2008, 5:51; 15 pages.
Glauber et al., "Adverse metabolic effect of omega-3 fatty acids in non-insulin-dependent diabetes mellitus", Ann Intern Med. 1988, 108(5):663-668.
Goncalves et al., "Fenofibrate prevents skeletal muscle loss in mice with lung cancer". PNAS. Jan. 23, 2018;115(4): E743-E752.
Gonzalez-Covarrubias et al., "Lipidomics of familial longevity". Aging Cell. 2013, 12(3):426-434.
Gonzalez-Covarrubias V., "Lipidomics in longevity and healthy aging". Biogerontology. 2013, 14(6):663-672.
Ghosh et al., "PAI-1 in tissue fibrosis." J Cell Physiol. (2011) 227(2):493-507.
Grundy et al., "Definition of metabolic syndrome: Report of the National Heart, Lung, and Blood Institute/American Heart Association conference on scientific issues related to definition", Circulation. 2004, 109(3):433-438.
Gunstone et al. [Eds.], "A review of even-chain fatty acid metabolism and the role of arachidic acid (C20:0) and lignoceric acid (C24:0) in health and disease", The Lipid Handbook, Gunstone et al. [Eds.] 3rd Edition, 2008, 604-635.
Hallgren et al., "Lymphocyte phytohemagllutinin responsiveness, immunoglobulins and autoantibodies in aging humans." J Immunol. (1973) 111:1101-1107.
Hall et al., "Annual, seasonal and individual variation in hematology and clinical blood chemistry profiles in bottlenose dolphins (*Tursiops truncatus*) from Sarasota Bay, Florida", Comp Biochem Physiol A Mol Integr Physiol. 2007, 148(2):266-277.
Hannun et al., "Principles of bioactive lipid signalling: lessons from sphingolipids", Nat Rev Mol Cell Biol. 2008, 9(2):139-150.
Hassanali et al., "Dietary supplementation of n-3 PUFA reduces weight gain and improves postprandial lipaemia and the associated inflammatory response in the obese JCR:LA-cp rat", Diabetes Obes Metab. 2010, 12(2):139-147.
Hebbel et al., A Systems Biology Consideration of the Vasculopathy of Sickle Cell Anemia: The Need for Multi-Modality Chemo-Prophylaxis, Cardiovsc Hematol Disord Drug Targets (200() 9(4):271-291.
Heneka et al., "Neuroinflammation in Alzheimer's Disease", Lancet Neurol. 2015, 14(4):388-405.
Hodge et al., "Plasma phospholipid and dietary fatty acids as predictors of type 2 diabetes: Interpreting the role of linoleic acid." Am J Clin Nutrition (2007) 86(1): 189-197.
Hodson et al., "Fatty acid composition of adipose tissue and blood in humans and its use as a biomarker of dietary intake", Prog Lipid Res. 2008, 47:348-380.

(56) References Cited

OTHER PUBLICATIONS

Holmes et al., "Systemic inflammation and disease progression in Alzheimer disease". Neurology 2009, 73(10):768-774.
Hosokawa et al., Fucoxanthin induces apoptosis and enhances the antiproliferative effect of the PPARγ ligand, troglitazone, on colon cancer cells. BBA Gen Subj. (2004) 675: 113-119.
Hwang et al., "Inhibitory Effects of 4-Guanidinobutyric Acid against Gastric Lesions", Biomol Ther. 2012, 20(2): 239-244.
International Diabetes Federation (2006) The IDF consensus worldwide definition of the Metabolic Syndrome. Brussels, Belgium., in 24 pages.
Janani et al., PPARγ gene—a review. Diab Metab Synd Clin Res Rev. (2015) 9: 46-50.
Jaruvongvanich et al., "Outcome of phlebotomy for treating nonalcoholic fatty liver disease: a systematic review and meta-analysis". Sauid J Gastroenterol. 2016, 22(6):407-414.
Jenkins et al., "A Review of Odd-Chain Fatty Acid Metabolism and the Role of Pentadecanoic Acid (C15:0) and Heptadecanoic Acid (C17:0) in Health and Disease", Molecules (2015) 20(2):2425-2444.
Jeon et al., "S-adenosylhomocysteine treatment of adult female fibroblasts alters X-chromosome inactivation and improves in vitro embryo development after somatic cell nuclear transfer", Reproduction, (2008) 135: 815-828.
Johnson et al., "Use of phlebotomy treatment in Atlantic bottlenose dolphins with iron overload". J Am Vet Med Assoc. 2009, 235(2):194-200.
Jové et al. Metabolomics of human brain aging and age-related neurodegenerative diseases. J Neuropathol Exp Neurol. 2014, 73(7): 640-657.
Jubie et al., "Design, synthesis and antidepressant activities of some novel fatty acid analogues". Med Chem Res. Apr. 2015;24(4): 1605-1616.
Kaddurah-Daouk, et al., Metabolomics: A global biochemical approach to the study of central nervous system diseases. Neuropsychopharmacol 2009. 34(1): 173-186.
Kanda et al., "MCP-1 contributes to macrophage infiltration into adipose tissue, insulin resistance, and hepatic steatosis in obesity", J Clin Invest. 2006, 116(6):1494-1505.
Kersten et al., "Roles of PPARs in health and disease", Nature. 2000, 405(6785):421-424.
Kiyota et al., "CCL2 Accelerates Microglia-Mediated Aβ Oligomer Formation and Progression of Neurocognitive Dysfunction". PLoS ONE. 2009, 4:e6197 in 12 pages.
Klock et al., "Sodium ascorbyl phosphate shows in vitro and in vivo efficacy in the prevention and treatment of acne vulgaris", International Journal of Cosmetic Science, 2005, 27(3):171-176.
Kohnken et al., "Overview of the use of murine models in leukemia and lymphoma research", Front Oncol. Feb. 20, 2017;7:22 in 11 pages.
Krachler et al., "Fatty Acid Profile of the Erythrocyte Membrane Preceding Development of Type 2 Diabetes Mellitus", Nutri Metabol Cardiovasc Diseases, (2008) 18(7):503-510.
Kratz et al., The relationship between high-fat dairy consumption and obesity, cardiovascular, and metabolic disease. Eur J Nutr. (2013) 52: 1-24.
Kratz et al., "Dairy fat intake is associated with glucose tolerance, hepatic and systemic insulin sensitivity, and liver fat but not β-cell function in humans", Am J Clin Nutr. 2014, 99(6):1385-1396.
Kriesberg et al., Cholesterol metabolism and aging, Am J Med. (1987) 82: 54-60.
Kristal et al., "Metabolomics: Opening Another Window into Aging". Sci Aging Knowledge Environ. 2005, 26:pe19 in 2 Pages.
Kühn et al., 2012, "Effect of Multipeak Spectral Modeling of Fat for Liver Iron and Fat Quantification:Correlation of Biopsy with MR Imaging Results". Radiology. 2012, 265(1):133-142.
LaBrecque et al., "World Gastroenterology Organisation global guidelines: Nonalcoholic fatty liver disease and nonalcoholic steatohepatitis". J Clin Gastroenterol. 2014, 48(6):467-473.

Lagerstedt et al., "Quantitative determination of plasma c8-c26 total fatty acids for the biochemical diagnosis of nutritional and metabolic disorders", Mol Genet Metab. 2001, 73(1):38-45.
Lai et al., "The protective effects and genetic pathways of thorn grape seeds oil against high glucose-induced apoptosis in pancreatic beta-cells", BMC Complement Altern Med. 2014, 14:10 (7 pages).
Larsen et al., "Sulfur-substituted and α-methylated fatty acids as peroxisome proliferator-activated receptor activators". Lipids. Jan. 2005;40(1): 49-57.
Lee et al., "PPARα and glucocorticoid receptor synergize to promote erythroid progenitor self-renewal", Nature (2005) 522: 474-477.
Lefebvre et al., "Antifibrotic Effects of the Dual CCR2/CCR5 Antagonist Cenicriviroc in Animal Models of Liver and Kidney Fibrosis". PLoS ONE. 2016. 11(6):e0158156 in 19 pages.
Leibovitz et al., PPAR activation: a new target for the treatment of hypertension. J Cardio Pharmacol. (2007) 50: 120-125.
Leyton et al., "Differential oxidation of saturated and unsaturated fatty acids in vivo in the rat". Br J Nutr. 1987, 57(3):383-393.
Liao et al., "Pioglitazone and cardiovascular outcomes in patients with insulin resistance, pre-diabetes and type 2 diabetes: a systematic review and meta-analysis". BMJ Open. 2017, 7(1):e013927 in 13 pages.
Liu et al., "Serum biomarkers for nonalcoholic fatty liver disease: Are we there yet?", Hepatology. 2017, 65(1):8-11.
Livrea et al., "Oxidative stress and antioxidant status in ß-thalassemia major: iron overload and depletion of lipid-soluble antioxidants." Blood. 1996, 88(9):3608-3614.
Loomba et al., "The ASK1 inhibitor selonsertib in patients with nonalcoholic steatohepatitis: A randomized, phase 2 trial". Hepatology. 2018, 67(2):549-559; avail online Dec. 2017; in 11 pages.
López-Ótin et al., "The Hallmarks of Aging", Cell Jun. 6, 2013;153(6):1194-1217.
Luquet et al., "Roles of PPAR δ in lipid absorption and metabolism: a new target for the treatment of type 2 diabetes", Biochim Biophys Acta. 2005, 1740:313-317.
Luzia et al., "The influence of season on the lipid profiles of five commercially important species of Brazilian fish", Food Chem. 2003, 83(1):93-97.
Ma et al., "Organization of the mammalian metabolome according to organ function, lineage specialization, and longevity". Cell Metab. 2015, 22(2):332-343.
Madrazo et al., The PPAR trio: Regulators of myocardial energy metabolism in health and disease. J Mol Cell Cariol. (2008) 44: 968-975.
Madsen et al., "Tetradecylthioacetic acid prevents high fat diet induced adposity and insulin resistance", J Lipid Res. 2002, 43:742-750.
Maeda T., Current topics on basic research for methamphetamine dependence and psychosis. J Wakayama Med. Soc., 2010, vol. 61, pp. 36-41.
Magnusdottir et al., "Plasma alkylresorcinols C17:0/C21:0 ratio, a biomarker of relative whole-grain rye intake, is associated to insulin sensitivity: a randomized study", Eur J Clin Nutr. 2014, 68(4):453-458.
Månsson H.L., "Fatty acids in bovine milk fat". Food Nutr Res. 2008, 52:4 in 3 pages.
Martin-Jiménez et al., Relationship between obesity, Alzheimer's disease, and Parkinson's disease: an astrocentric view. Publ. online Oct. 28, 2016; Mol Neurobiol. 2017, 54(9):7096-7115.
Maruyama et al., "Differences in Serum Phospholipid Fatty Acid Compositions and Estimated Desaturase Activities Between Japanese Men With and Without Metabolic Syndrome", J Atheroscler Thromb. 2008, 15(6):306-313.
Mayneris-Perxachs et al., "Plasma fatty acid composition, estimated desaturase activities, and their relation with the metabolic syndrome in a population at high risk of cardiovascular disease". Clinical Nutrition. 2013, HTTP://dx.doi.org/10.1016/j.clnu.2013.03.001.
Mayo Clinic, Asthma, 2017, https://www.mayoclinic.org/diseases-conditions/asthma/basics/treatment/con-20026992 in 6 pages.
Mayo Clinic, Cholesterolgallstones, 2017, https://www.mayoclinic.org/diseases-conditions/gallstones/diagnosis-treatment/drc-20354220 in 3 pages.

(56) References Cited

OTHER PUBLICATIONS

Mazzaro et al., "Iron indices among bottlenose dolphins (*Tursiops truncatus*)". Comp Med. 2012, 62(6):508-515.
McGeer et al., "Inflammation, Antiinflammatory Agents, and Alzheimer's Disease: The Last 22 Years". J Alzheimers Dis. 2016, 54(3):853-857.
McGowen M., "Dolphin genome provides evidence for adaptive evolution of nervous system genes and a molecular rate slowdown", Proc Biol Sci. 2012, 279(1743):3643-3651.
McMurchie E.J., "Dietary lipids and the regulation of membrane fluidity and function". Publisher: Alan R. Liss, Inc.; Physiol Reg Memb Fuid. 1988, 189-237.
Meglasson et al., Antihyperglycemic action of guanidinoalkanoic acids: 3-Guanidinopropionic Acid Ameliorates Hyperglycemia in Diabetic KKA/\ y and C57BL6J ob/ob Mice and Increases Glucose Disappearance in Rhesus Monkeys. J Pharm Exp Thera. Sep. 1, 1993;266(3): 1454-1462.
Meikle et al., "Plasma Lipid Profiling Shows Similar Associations with Prediabetes and Type 2 Diabetes". PloS one, 2013, 8(9), e74341; 43 pages.
Mennen et al., "Possible protective effect of bread and dairy products on the risk of the metabolic syndrome", Nutrition Res. 2000, 20(3):335-347.
Mi, "Myocardial Infarction", 2017, MedlinePlus Medical Encyclopedia; URL: <https://medlineplus.gov/ency/article/000195.htm> in 7 pages.
Milam et al., PPAR-γ agonists inhibit profibrotic phenotypes in human lung fibroblasts and bleomycin-induced pulmonary fibrosis. Am J Physiol Lung Cell Mol Physiol. (2008) 94: L891-L901.
Miyake et al., "Maternal consumption of dairy products, calcium, and vitamin D during pregnancy and infantile allergic disorders." Ann Allergy Asthma Immunol. (2014) 113(1): 82-87. (Abstract p. S224).
Montoliu et al., Serum profiling of healthy aging identifies phosphor- and sphingolipid species as markers of human longevity. Aging (Albany NY). 2014, 6(1):9-25.
Morsy et al., "Can eicosapentaenoic acid maintain the original ribavirin dose or affect the response during the treatment course of chronic hepatitis C virus (HCV) patients?", Turk J Gastroenterol. 2016, 27:55-61.
Nanji et al., "Dietary saturated fatty acids reverse inflammatory and fibrotic changes in rat liver despite continued ethanol administration." J Pharmacol Exp Ther. 2001, 299(2):638-644.
Nelson et al., "Relationship between the pattern of hepatic iron deposition and histologic severity in nonalcoholic fatty liver disease". Hepatology. 2011, 53(2):448-457.
Nestel et al., Specific plasma lipid classes and phospholipid fatty acids indicative of dairy food consumption associate with insulin sensitivity. Am J Clin Nutr., 2014, 99(1):46-53.
Nestel P., "Trans fatty acids: are its cardiovascular risks fully appreciated?". Clin Ther. 2014, 36(3):315-321.
Neuschwander-Tetri et al., "Farnesoid X nuclear receptor ligand obeticholic acid for non-cirrhotic, non-alcoholic steatohepatitis (FLINT): a multicentre, randomised, placebo-controlled trial". Lancet. 2015, 385(9972):956-965. 956-965.
Nilsson S., "Long-term treatment with methenamine hippurate in recurrent urinary tract infection", Acta Med Scand. (1975) 198(1-2): 81-85.
Novgorodtseva et al., "Composition of fatty acids in plasma and erythrocytes and eicosanoids level in patients with metabolic syndrome". Lipids Health Dis. 2011, 10:82 in 5 pages.
Novgorodtseva et al., "Modification of fatty acids composition in erythrocytes lipids in arterial hypertension associated with dyslipidemia". Lipids Health Dis. 2011, 10:18 in 5 pages.
Oberley et al., "Laboratory testing for cobalamin deficiency in megaloblastic anemia". Am J Hematol. (2013) 88(6):522-524.
Ojala et al., "Expression of interleukin-18 is increased in the brains of Alzheimer's disease patients". Neurobiol Aging. 2009, 30(2):198-209.
Otogawa et al., "Erythrophagocytosis by Liver Macrophages (Kupffer Cells) Promotes Oxidative Stress, Inflammation, and Fibrosis in a Rabbit Model of Steatohepatitis: Implications for the Pathogenesis of Human Nonalcoholic Steatohepatitis". Am J Pathol. 2007, 170(3):967-980.
Özogul et al., Fatty acid profiles and fat contents of commercially important seawater and freshwater fish species of Turkey: A comparative study. Food Chem. 2007, 103:217-223.
Panee J., "Monocyte Chemoattractant Protein 1 (MCP-1) in Obesity and Diabetes", Cytokine. (2012) 60(1):1-12.
Patel et al., "Fatty acids measured in plasma and erythrocyte-membrane phospholipids and derived by food-frequency questionnaire and the risk of new-onset type 2 diabetes: a pilot study in the European Prospective Investigation into Cancer and Nutrition (EPIC)—Norfolk cohort". Am J Clin Nutri. 2010, 92(5):1214-1222.
Penckofer et al., "Oxidative stress and cardiovascular disease in type 2 diabetes: the role of antioxidants and prooxidants". J Cardiovasc Nurs. 2002, 16(2):68-85.
Pereira et al., "Dairy consumption, obesity, and the insulin resistance syndrome in young adults: the Cardia study", JAMA. 2002, 287(16):2081-2089.
Perry VH., "Contribution of systemic inflammation to chronic neurodegeneration". Acta Neuropathol. 2010, 120(3):277-286.
Perry et al., "Microglia and macrophages of the central nervous system: the contribution of microglia priming and systemic inflammation to chronic neurodegeneration". Semin Immunopathol. (2013) 35:601-612.
Pfeuffer et al., "Milk and the metabolic syndrome", Obes Rev. 2007, 8(2):109-118.
Pfeuffer et al., "Pentadecanoic and Heptadecanoic Acids: Multifaceted Odd-Chain Fatty Acids", Adv Nutr. 2016, 7:730-734.
Pietrangelo A. "Iron in NASH, chronic liver diseases and HCC: how much iron is too much?", J Hepatol. 2009, 50(2):249-251.
Popp-Snijders et al., "Dietary supplementation of omega-3 polyunsaturated fatty acids improves insulin sensitivity in non-insulin-dependent diabetes", Diabetes Res 1987, 4(3):141-147.
Profenno et al., "Meta-analysis of Alzheimer's disease risk with obesity, diabetes, and related disorders", Biol Psychiatry. 2010, 67(6):505-512.
Pubchem. CID 325395, Mar. 26, 2005; pp. 1-13; retrieved from the Internet <URL: https://pubchem.ncbi.nlm.nih.gov//compound/325395>.
Qin et al., "Peroxisome proliferator-activated receptor-δ induces insulin-induced gene-1 and suppresses hepatic lipogenesis in obese diabetic mice", Hepatology, 2008, 48(2):432-441.
Quintanilla et al., "Role of PPARγ in the Differentiation and Function of Neurons", Hindawi Publ. Corp. 2014; Article ID 768594 in 10 pages.
Ramírez et al., "Absorption and distribution of dietary fatty acids from different sources". Early Hum Develop. 2001, 65(Suppl):S95-S101.
Ratziu V., "Novel pharmacotherapy options for NASH". Dig Dis Sci. 2016, 61(5):1398-1405.
Ratziu et al., "Elafibranor, an agonist of the peroxisome proliferator-activated receptor-α and -δ, induces resolution of nonalcoholic steatohepatitis without fibrosis worsening". Gastroenterology. 2016, 150(5):1147-1159.
Robinson et al., "N-3 polyunsaturated fatty acids: relationship to inflammation in healthy adults and adults exhibiting features of metabolic syndrome." Lipids. 2013, 48(4):319-332.
Ross et al., "CHF5074 reduces biomarkers of neuroinflammation in patients with mild cognitiveImpairment: a 12-week, double-blind, placebo-controlled study". Curr Alzheimer Res. 2013, 10(7):742-753.
Ruidavets et al., "High consumptions of grain, fish, dairy products and combinations of these are associated with a low prevalence of metabolic syndrome", J Epidemiol Community Health, 2007, 61(9):810-817.
Safadi et al., "The fatty acid-bile acid conjugate Aramchol reduces liver fat content in patients with nonalcoholic fatty liver disease". Clin Gastroenterol Hepatol. 2014, 12(12):2085-2091.

(56) References Cited

OTHER PUBLICATIONS

Salameh et al., "Insulin resistance, dyslipidemia, and apolipoprotein E interactions as mechanisms in cognitive impairment and Alzheimer's disease", Exp Biol Med (Maywood). 2016, 241(15):1676-1683.
Salek et al., A metabolomic study of the CRND8 transgenic mouse model of Alzheimer's disease. Neurochem Int. 2010. 56(8): 937-947.
Sanches et al., "Nonalcoholic Steatohepatitis: A Search for Factual Animal Models". Biomed Res Int. 2015, doi: [10.1155/2015/574832] in 13 pages.
Sandrou et al., "Low-fat/calorie foods: current state and perspectives", Crit Rev Food Sci Nutr. 2000, 40(5):427-447.
Sarikurkcu et al., "Screening of Possible In Vitro Neuroprotective, Skin Care, Antihyperglycemic,and Antioxidative Effects of *Anchusa undulata* L. subsp. hybrida (Ten.) Coutinho from Turkey and Its Fatty Acid Profile", International J Food Proper. 2015, 18(7):1491-1504.
Sarikurkcu et al., Publication date, 2019, email dated Jun. 18, 2019 in 19 pages.
Schmeda-Hirschmann et al., Anti-inflammatory activity of animal oils from the Peruvian Amazon. J Ethnopharmacol. 2014, 156:9-15.
Seki et al., "Eicosapentaenoic Acid (EPA) Attenuates the Anemia Due to Ribavirin/Interferon a Treatment in Patients with Chronic Hapatitis C", 2004, 3199 in 4 pages.
Sertznig et al., Peroxisome proliferator-activated receptors (PPARs) and the human skin. Am J Clin Dermatol. (2008) 9: 15-31.
Shaw C., "Possible Modulation by Glutathione of Glutamatergic", in Glutathione in the Nervous System, CRC Press, 1998. Chapter 7, pp. 140-142.
Sindhu et al., "Obesity Is a Positive Modulator of IL-6R and IL-6 Expression in the Subcutaneous Adipose Tissue: Significance for Metabolic Inflammation". PLoS ONE. 2015, 10(7):e0133494 in 17 pages.
Slifka KA. , Comparative diet analysis of fish species commonly consumed by managed and free-ranging bottlenose dolphins (*Tursiops truncatus*). Int J Vet Med. (2013) 10:1.
Sokolowska et al., Peroxisome proliferator-activated receptor gamma (PPAR-gamma) and their role in immunoregulation and inflammation control. Postepy Higieny (2005) 59: 472-484; Abstract in 2 pages.
Sobolesky et al., "Feeding a Modified Fish Diet to Bottlenose Dolphins Leads to an Increase in Serum Adiponectin and Sphingolipids", Front Endocrinol. 2016, 7:33 in 11 pages.
Song et al., Hippocampal PPARα is a novel therapeutic target for depression and mediates the antidepressant actions of fluoxetine in mice, Br J Pharmacol. Jul. 2018;175(14): 2968-2987.
Sorrentino et al., "Liver iron excess in patients with hepatocellular carcinoma developed on non-alcoholic steato-hepatitis". J Hepatol. 2009, 50(2):351-357.
Sotgia et al., "Hercynine content in widely consumed commercial beverages". LWT Food Science Tech. Dec. 1, 2018;98: 465-469.
Spyridaki et al., (2016) Obesity, inflammation and cognition. Curr Opin Behav Sci. 2016, 9: 169-175.
Stenmark et al., "Animal models of pulmonary arterial hypertension: the hope for etiological discovery and pharmacological cure". Am J Physiol Lung Cell Mol Physiol. Dec. 2009;297(6): L1013-L1032.
Stephenson et al., "Building a Roadmap for Developing Combination Therapies for Alzheimer's Disease", Expert Rev Neurother. 2015, 15(3):327-333.
Suresh et al., "Protective action of arachidonic acid against alloxan-induced cytotoxicity and diabetes mellitus". Prostaglandins Leukot Essent Fatty Acids, 2001, 64(1):37-52.
Swaminathan et al., "The role of iron in diabetes and its complications", Diabetes Care. 2007, 30(7):1926-1933.
Targher et al., "Elevated levels of interleukin-6 in young adults with type 1 diabetes without clinical evidence of microvascular and macrovascular complications". Diabetes Care (2001) 24(5):956-957.

Targher et al., "Risk of Cardiovascular Disease in Patients with Nonalcoholic Fatty Liver Disease", N Engl J Med., 2010, 363:1341-1350.
Trifilieff et al., PPAR-α and -γbut not -δ agonists inhibit airway inflammation in a murine model of asthma: in vitro evidence for an NF-kβ-independent effect. Br J Pharmacol. (2003) 139: 163-171.
Trushina et al., Identification of altered metabolic pathways in plasma and CSF in mild cognitive impairment and Alzheimer's disease using metabolomics. PLoS ONE 2013. 8(5): e63644 in 13 pages.
Trushina et al., Recent advances in the application of metabolomics to Alzheimer's disease. Bioch Biophy Acta. 2014.1842(8): 1232-1239.
Tucsek et al., "Obesity in Aging Exacerbates Blood-Brain Barrier Disruption, Neuroinflammation, and Oxidative Stress in the Mouse Hippocampus: Effects on Expression of Genes Involved in Beta-Amyloid Generation and Alzheimer's Disease", J Gerontol A Biol Sci Med Sci. 2014, 69(10):1212-1226; publ. online Nov. 11, 2013.
Unnikrishnan et al., "Antiinflammatory activity of methionine, methionine sulfoxide and methionine sulfone". Agents Actions. 1990, 31(1-2):110-112.
Valenti et al., "Iron depletion by phlebotomy improves insulin resistance in patients with nonalcoholic fatty liver disease and hyperferritinemia: evidence from a case-control study". Am J Gastroenterol. 2007, 102(6):1251-1258.
Valenti et al., "[769] Iron Depletion by phlebotomy improves insulin resistance in patients with nonalcoholic fatty liver disease and hyperferritinemia: evidence from a case-control study", J Hepatol. (Apr. 2007) 46:S288-S289.
Valenti et al., "A randomized trial of iron depletion in patients with nonalcoholic fatty liver disease and hyperferritinemia". World J Gastroenterol. 2014, 20(11):3002-3010.
Van Eldik et al., The roles of inflammation and immune mechanisms in Alzheimer's disease. Alzheimers Dement (N.Y.), 2016, 2(2):99-109.
Venn-Watson et al., "Big brains and blood glucose: common ground for diabetes mellitus in humans and healthy dolphins", Comp Med., 2007, 57(4):390-395.
Venn-Watson et al., "Assessment of increased serum aminotransferases in a managed Atlantic bottlenose dolphin (*Tursiops truncatus*) population", J Wildlf Dis. 2008, 44(2):318-330.
Venn-Watson et al., "Dolphins as animal models for type 2 diabetes: sustained, post-prandial hyperglycemia and hyperinsulinemia", Gen Comp Endocrinol. 2011, 170(1):193-199.
Venn-Watson et al., Associations of ceruloplasmin and haptoglobin with inflammation and glucose in bottlenose dolphins (*Tursiops truncatus*) J Comp Clin Path. 2014, 23(4):1031-1036.
Venn-Watson S., "Dolphins and Diabetes: Applying One Health for breakthrough discoveries". Front Endocrinol (Lausanne); 2014, 5:227 in 2 pages.
Venn-Watson et al., "Investigation of Fish-Based Nutrients to Protect Against Metabolic Syndrome In Bottlenose Dolphins (*Tursiops Truncatus*)", presentation at International Association for Aquatic Animal Medicine (IAAAM), Gold Coast, Australia, May 2014.
Venn-Watson et al., "Adrenal Gland and Lung Lesions in Gulf of Mexico Common Bottlenose Dolphins (*Tursiops truncatus*) Found Dead following the Deepwater Horizon Oil Spill". PLoS ONE 2015 10(5):e0126538 in 23 pages.
Venn-Watson et al., "Evaluation of annual survival and mortality rates and longevity of bottlenose dolphins (*Tursiops truncatus*) at the United States Navy Marine Mammal Program from 2004 through 2013", J Am Vet Med. 2015, 246(8):893-898.
Wang et al., "Obesity modifies the relations between serum markers of dairy fats and inflammation and oxidative stress among adolescents." Obesity (Silver Spring), 2011, 19(12):2404-2410.
Warensjö et al., "Biomarkers of milk fat and the risk of myocardial infarction in men and women: a prospective, matched case-control study." Am J Clin Nutr. (2010) 92(1):194-202.
Wei et al., Peroxisome proliferator-activated receptor γ: innate protection from excessive fibrinogenesis and potential therapeutic target in systemic sclerosis. Curr Opin Rheumatol. (2010) 22(6): 671-676.

(56) References Cited

OTHER PUBLICATIONS

Weiss et al., "Anemia of chronic disease." New Engl J Med. 2005, 352:1011-1023.
Wells et al., "Bottlenose dolphins as marine ecosystem sentinels: developing a health monitoring system", EcoHealth 2004, 1:246-254.
Wells et al., "Evaluation of Potential Protective Factors Against Metabolic Syndrome in Bottlenose Dolphins: Feeding and Activity Patterns of Dolphins in Sarasota Bay, Florida", Front Endocrinol (Lausanne), 2013, 4:139 in 16 pages.
Wlazlo et al., Iron metabolism is associated with adipocyte insulin resistance and plasma adiponectin. Diabetes Care, 2012, 36(2):309-315.
Wu et al., "Alterations of the Neuroinflammatory Markers IL-6 and TRAIL in Alzheimer's Disease", Dement Geriatr Cogn Dis Extra. 2015, 5(3):424-434.
Xu et al., "Molecular Recognition of Fatty Acids by Peroxisome Proliferator-Activated Receptors", Mol Cell. 1999, 3:397-403.
Yamano et al., "A long-term high-fat diet changes iron distribution in the body, increasing iron accumulation specifically in the mouse spleen.". J Nutr Sci Vitaminol. (Tokyo) 2015, 61(1):20-27.
Yin et al., "Concurrent Epstein-Barr virus associated NK/T cell lymphoma after immunosuppressive therapy for aplastic anemia: report of a case and review of literature". Int'l J Clin Exper Pathol. (2015) 8(6):7588 in 6 pages.
Zandman-Goddard et al., "Hyperferritinemia in autoimmunity". IMAJ, 2008, 10: 83-84.
Zandman-Goddard et al., "Ferritin in autoimmune diseases". Autoimmunity Rev. 2007, 6:457-463.
Zhao et al., Body iron stores and heme-iron intake in relation to type 2 diabetes: a systematic review and meta-analysis. PLoS ONE 2012, 7:e41641.
Cusi et al., Metformin: A review of its metabolic effects. Diab Rev. Jan. 1, 1998;6(2): 89-131.
Szente et al., Fatty acid-cyclodexrin complexes: properties and applications, J Inclusion Phenomena & Molecular Recognition in Chemistry Dec. 1993;16: 339-354.
Ardura-Fabregat et al., "Targeting Neuroinflammation to Treat Alzheimer Disease". CNS Drugs. Dec. 2017;31: 1057-1082.
Cole et al., "Omega-3 fatty acids and dementia". Prostaglandins Leukot Essent Fatty Acids. Aug. 1, 2009;81(2-3): 213-221.
Contreras et al., "Myristic acid prodces anxiolytic-like effects in Wistar Rats in th elevated plus maze". Biomed Res Int. 2014;492141; 8 pages.
DiSabato et al., "Neuroinflammation: The devil is in the details". J Neurochem. Oct. 2016; 139(suppl. 2): 136-153.
Haast et al., "Impact of fatty acids on brain circulation, structure and function". Prostaglandins, Leukotrienes and Essential Fatty Acids. Jan. 1, 2015;92: 3-14.
Harbige et al., "Polyunsaturated fatty acids in the pathogenesis and treatment of multiple sclerosis". Br J Nutrition. Oct. 2007;98(S1): S46-53.
Hörig et al., From bench to clinic and back: Perspective on the 1 st IQPC Translational Research conference. J TranslMed. Dec. 2004;2: 1-8.
Ikwuobe O.J., The role of odd chain fatty acids on hepatocyte and monocyte function. Aston University Doctoral Thesis, Apr. 2018; 273 pages.
Irmisch et al., "Fatty acids and sleep in depressed inpatients." Prostaglandins, leukotrienes and essential fatty acids. Jan. 1, 2007;76(1): 1-7.
Moon et al., "The saturated fatty acid, palmitic acid, induces anxiety-like behavior in mice". Metabolism. Sep. 1, 2014;63(9):1131-40.
Palacios et al., "Circulating Plasma Metabolites and Cognitive Function in a Puerto Rican Cohort". J Alzheimers Dis. Jan. 1, 2020;76(4): 1267-1280.
Platten et al., "Treatment of Autoimmune Neuroinflammation with a Synthetic Tryptophan Metabolite". Science. Nov. 4, 2005;310(5749): 850-855.
Priebe et al., "Clinical Roundup: Selected treatment options for opioid addition—Part 2". Alternative & Complimentary Therapies. Feb. 2019;25(1): 56-58.
Schäfer et al. "Failure is an option: Learning from unsuccessful proof-of-concept trials". Drug Discovery Today Nov. 2008;13(21-22): 913-916.
Serhan C.N., "Treating Inflammation and Infection in the 21st Century: New Hints from Decoding Resolution Mediators and Mechanisms". The FASEB J. Apr. 2017;31(4): 1273 in 17 pages.
Silva et al., "Long-chain omega-3 fatty acids supplementation accelerates nerve regeneration and prevents neuropathic pain behavior in mice". Front Pharmacol. Oct. 17, 2017;8: 723; 12 pages.
Venigalla et al., "Novel Promising Therapeutics Against Chronic Neuroinflammation and Neurodegeneration in Alzheimer's Disease". Neurochem International. May 1, 2016;95: 63-74.
Zhang et al., "Inflammatory Microenvironment in Gastric Premalignant Lesions: Implication and Application". Front Immunol. Nov. 15, 2023;14: 1297101 in 13 pages.
Ogita et al., "Possible Modulation by Glutathione of Glutamatergic Neurotransmission". In Glutathione in the Nervous System by Shaw C.A. [Ed.]; Feb. 27, 1998; Chapter 7, pp. 137-161.

\* cited by examiner

PENTADECANOYLCARNITINE FOR TREATMENT OF CONDITIONS RELATED TO THE QUALITY OF AGING AND LONGEVITY

STATEMENT REGARDING FEDERALLY SPONSORED R&D

The United States Government has certain rights in this invention, under ONR SBIR Agreement No. N00014-21-9-0002.

FIELD OF THE INVENTION

Administration of pentadecanoylcarnitine or pentadecanoic acid is provided for prevention, management or treatment of aggression, allergies, allergic rhinitis, Alzheimer's disease, anxiety and anxiety disorders, amyotrophic lateral sclerosis, arthritis, asthma, atherosclerosis, attention-deficit hyperactivity disorder, bipolar disorder, brain damage, cancer, cardiovascular disease, cholestatic pruritis, depression, chronic obstructive pulmonary disease (COPD), cocaine abuse, cough, dermatitis, depression, drug-seeking behavior, gastrointestinal disorders, facial erythema associated with rosacea, glaucoma, hepatic diseases, hyperactive bladder, hypersensitivity disorders, hypertension, impulsivity, inflammation, mental disorders and conditions, metabolic disorders, migraines, nasal and sinus congestion, nausea, neuropathic pain with and symptoms of multiple sclerosis, neurological and neuropsychiatric disorders, obesity, obsessive-compulsive disorders, opioid-induced respiratory depression, osteoarthritis, pain, Parkinson disease, pathological gambling, peptic ulcers, schizophrenia, sleep disorders, spinal cord injury, tardive dyskinesia, tics and behavioral problems with Tourette's syndrome; as well as for supporting appetite, cardiovascular health, hematologic health, memory, metabolic health, mood, prolonged REM sleep, renal health, sexuality, sociability and metabolic, hematological, renal, and weight loss.

BACKGROUND OF THE INVENTION

Carnitine is an amino acid present in food, primarily in animal sources, but it can also be made endogenously. L-carnitine is the bioavailable and biologically active isomer. Carnitines are almost entirely found within cells, where they can shuttle long-chain fatty acids into mitochondria as long-chain acylcarnitines to enable β-oxidation-generated energy for cellular activities.

SUMMARY OF THE INVENTION

Compositions and methods are provided for prevention, management or treatment of aggression, allergies, allergic rhinitis, Alzheimer's disease, anxiety and anxiety disorders, amyotrophic lateral sclerosis, arthritis, asthma, atherosclerosis, attention-deficit hyperactivity disorder, bipolar disorder, brain damage, cancer, cardiovascular disease, cholestatic pruritis, depression, chronic obstructive pulmonary disease (COPD), cocaine abuse, cough, dermatitis, depression, drug-seeking behavior, gastrointestinal disorders, facial erythema associated with rosacea, glaucoma, hepatic diseases, hyperactive bladder, hypersensitivity disorders, hypertension, impulsivity, inflammation, mental disorders and conditions, metabolic disorders, migraines, nasal and sinus congestion, nausea, neuropathic pain with and symptoms of multiple sclerosis, neurological and neuropsychiatric disorders, obesity, obsessive-compulsive disorders, opioid-induced respiratory depression, osteoarthritis, pain, Parkinson disease, pathological gambling, peptic ulcers, schizophrenia, sleep disorders, spinal cord injury, tardive dyskinesia, tics and behavioral problems with Tourette's syndrome; as well as for supporting appetite, cardiovascular health, hematologic health, memory, metabolic health, mood, prolonged REM sleep, renal health, sexuality, sociability and metabolic, hematological, renal, and weight loss. These compositions comprise pentadecanoylcarnitine or pentadecanoic acid, or salts thereof, which may be administered in combination with other medicaments or as part of various treatment regimens as described herein. The provided compositions are effective for modulating markers as described herein. Methods are provided for administering the compositions.

Accordingly, in a generally applicable first aspect (i.e., independently combinable with any of the aspects or embodiments identified herein), a pharmaceutical composition is provided comprising: pentadecanoylcarnitine or pentadecanoic acid; and a pharmaceutically acceptable carrier.

In an embodiment of the first aspect (i.e., independently combinable with any of the aspects or embodiments identified herein), the composition is in a unit dosage form.

In an embodiment of the first aspect (i.e., independently combinable with any of the aspects or embodiments identified herein), the pharmaceutical composition is configured for administration of from 2.5 mg to 50 mg, per 1 kg of body weight, of the pentadecanoylcarnitine or pentadecanoic acid, or pharmaceutically acceptable salts thereof to a patient.

In an embodiment of the first aspect (i.e., independently combinable with any of the aspects or embodiments identified herein), the pharmaceutical composition is configured for administration once per day.

In an embodiment of the first aspect (i.e., independently combinable with any of the aspects or embodiments identified herein), the pharmaceutical composition comprises from 0.01 mg to 10000 mg of pentadecanoylcarnitine or pentadecanoic acid or pharmaceutically acceptable salts thereof.

In a generally applicable second aspect (i.e., independently combinable with any of the aspects or embodiments identified herein), use is provided of a pharmaceutical composition of the first aspect or any embodiment thereof, in the manufacture of a medicament for treatment or prophylaxis of conditions as described herein.

In an embodiment of the second aspect (i.e., independently combinable with any of the aspects or embodiments identified herein), the use is in the manufacture of a medicament for treatment or prophylaxis of conditions as described herein.

In an embodiment of the second aspect (i.e., independently combinable with any of the aspects or embodiments identified herein), the pharmaceutical composition is configured to modulate a marker of aging-associated conditions described herein or a symptom of conditions described herein.

In an embodiment of the second aspect (i.e., independently combinable with any of the aspects or embodiments identified herein), the marker of conditions related to an indication herein is selected from the group consisting of serum or plasma pentadecanoylcarnitine concentration, red blood cell indices (i.e. hemoglobin, red blood cells), serum or plasma cholesterol, triglycerides, insulin, glucose, gamma-glutamyl transpeptidase, ferritin, or iron.

In a generally applicable third aspect (i.e., independently combinable with any of the aspects or embodiments identified herein), the pharmaceutical composition is configured to increase a serum, red blood cell, or tissue concentration of pentadecanoylcarnitine to between 0.2 µM and 20 µM.

In an embodiment of the third aspect (i.e., independently combinable with any of the aspects or embodiments identified herein), the pentadecanoylcarnitine or pharmaceutically acceptable salts thereof is provided as a pharmaceutical composition in a unit dosage form.

In an embodiment of the third aspect (i.e., independently combinable with any of the aspects or embodiments identified herein), the unit dosage form comprises from 0.01 mg to 10000 mg of the pentadecanoylcarnitine.

In an embodiment of the third aspect (i.e., independently combinable with any of the aspects or embodiments identified herein), the pharmaceutical composition further comprises a plurality of different small molecule metabolites described herein.

In an embodiment of the third aspect (i.e., independently combinable with any of the aspects or embodiments identified herein), from 2.5 mg to 50 mg of pentadecanoylcarnitine or pharmaceutically acceptable salts thereof is administered to the patient, per 1 kg of body weight, per day.

In an embodiment of the third aspect (i.e., independently combinable with any of the aspects or embodiments identified herein), the pentadecanoylcarnitine or pharmaceutically acceptable salts thereof is administered to the patient once per day.

In an embodiment of the third aspect (i.e., independently combinable with any of the aspects or embodiments identified herein), a serum, tissue, or a red blood cell membrane concentration of pentadecanoylcarnitine is increased 1.25 to 6 times above the patient's baseline levels to achieve concentrations between 0.5 µM and 20 µM.

In a generally applicable fourth aspect (i.e., independently combinable with any of the aspects or embodiments identified herein), use is provided of pentadecanoylcarnitine or pentadecanoic acid to achieve body concentrations of pentadecanoylcarnitine of from 1 µM and 20 µM to prevent, manage or treat aggression, allergies, allergic rhinitis, Alzheimer's disease, anxiety and anxiety disorders, amyotrophic lateral sclerosis, arthritis, asthma, atherosclerosis, attention-deficit hyperactivity disorder, bipolar disorder, brain damage, cancer, cardiovascular disease, cholestatic pruritis, depression, chronic obstructive pulmonary disease (COPD), cocaine abuse, cough, dermatitis, depression, drug-seeking behavior, gastrointestinal disorders, facial erythema associated with rosacea, glaucoma, hepatic diseases, hyperactive bladder, hypersensitivity disorders, hypertension, impulsivity, inflammation, mental disorders and conditions, metabolic disorders, migraines, nasal and sinus congestion, nausea, neuropathic pain with and symptoms of multiple sclerosis, neurological and neuropsychiatric disorders, obesity, obsessive-compulsive disorders, opioid-induced respiratory depression, osteoarthritis, pain, Parkinson disease, pathological gambling, peptic ulcers, schizophrenia, sleep disorders, spinal cord injury, tardive dyskinesia, tics and behavioral problems with Tourette's syndrome; as well as supporting appetite, cardiovascular health, hematologic health, memory, metabolic health, mood, prolonged REM sleep, renal health, sexuality, sociability and metabolic, hematological, renal, and weight loss.

In a generally applicable fifth aspect (i.e., independently combinable with any of the aspects or embodiments identified herein), a composition substantially as described herein is provided.

In a generally applicable sixth aspect (i.e., independently combinable with any of the aspects or embodiments identified herein), a composition substantially as described herein is provided.

In a generally applicable seventh aspect (i.e., independently combinable with any of the aspects or embodiments identified herein), a use substantially as described herein is provided.

DETAILED DESCRIPTION

Figure 1A:
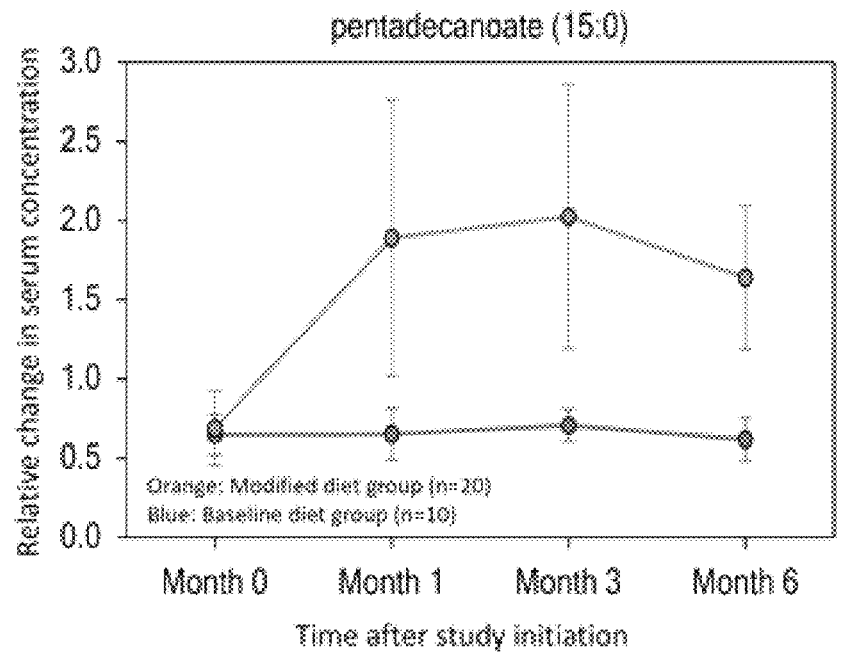
FIG. 1A shows increased serum pentadecanoic acid (C15:0) concentrations within 1 month on the modified fish diet that was sustained through 6 months.

Compositions including pentadecanoylcarnitine or pentadecanoic acid, and associated methods for treatment of conditions including aggression, allergies, allergic rhinitis, Alzheimer's disease, anxiety and anxiety disorders, amyotrophic lateral sclerosis, arthritis, asthma, atherosclerosis, attention-deficit hyperactivity disorder, bipolar disorder, brain damage, cancer, cardiovascular disease, cholestatic pruritis, depression, chronic obstructive pulmonary disease (COPD), cocaine abuse, cough, dermatitis, depression, drug-seeking behavior, gastrointestinal disorders, facial erythema associated with rosacea, glaucoma, hepatic diseases, hyperactive bladder, hypersensitivity disorders, hypertension, impulsivity, inflammation, mental disorders and conditions, metabolic disorders, migraines, nasal and sinus congestion, nausea, neuropathic pain with and symptoms of multiple sclerosis, neurological and neuropsychiatric disorders, obesity, obsessive-compulsive disorders, opioid-induced respiratory depression, osteoarthritis, pain, Parkinson disease, pathological gambling, peptic ulcers, schizophrenia, sleep disorders, spinal cord injury, tardive dyskinesia, tics and behavioral problems with Tourette's syndrome; as well as supporting appetite, cardiovascular health, hematologic health, memory, metabolic health, mood, prolonged REM sleep, renal health, sexuality, sociability and metabolic, hematological, renal, and weight loss are provided.

Aging is associated with chronic, low-grade inflammation characterized by increased circulating levels of proinflammatory cytokines, neutrophils, and progressively activated macrophages. This pro-inflammatory state is a significant risk factor for both morbidity and mortality in the elderly people (Franceschi C, Campisi J (2014) Chronic inflammation (inflammaging) and its potential contribution to age-associated diseases. J Gerontol Ser A 69: S4-S9). People who live at least 100 years are less likely to have developed a proinflammatory state with age, further supporting that chronic, low-grade inflammation impairs quality and duration of life (Vasto S, Candore G, Balistreri M, Colonna-Romano G, Grimaldi M P, Listi F et al. (2007) Inflammatory networks in ageing, age-related diseases, and longevity. Mech Ageing and Dev 128:83-91). As such, interventions to reduce inflammation of aging have been proposed to concurrently treat multiple aging-associated diseases, resulting in improved quality of life and expanded longevity.

As people age, the prevalence of anemia can increase dramatically. Comparisons of populations aged 40, 60, 80, 90 and 100 (total n=1,980) had the following prevalence of anemia: 16.1%, 19.1%, 41.1%, 46.2%, and 57.1% (Zhai Y, Yin Z X, Xu J W, Liu Y Z, Shi X M (2010) Anemia status and its relevant factors among elderly people aged above 80 years old in longevity areas in China. Chinese J of Prev Med 44:115-118). The presence of anemia and low hemoglobin concentration increased the 3-year mortality risk by 25% and decreased longevity among older people (Lyu Y, Yin Z, Luo J, Shi X, Zeng Y (2015) Zhonghua Liuxingbingxue Zazhi 36:682-686). Means to prevent and treat anemia of aging are expected to improve quality of life and expand longevity.

Elevated cholesterol with aging can negatively impact quality of life or longevity. (Kriesberg R A and Kasim S (1987) Cholesterol metabolism and aging, Am J Med 82:54-60). Elevated cholesterol, especially elevated low-density lipoprotein (LDL) cholesterol, have been identified as underlying causes of or contributors to cardiovascular disease, including atherosclerosis, which also increase in prevalence with age. Lower cholesterol levels, especially for people under 50 years old, have been associated with improved longevity (Anderson K M, Castelli W P, Levy D (1987) Cholesterol and mortality: 30 years of follow-up from the Framingham Study JAMA 257:2176-2180). Similarly, triglyceride levels can be major predicting factors for human longevity, with lower triglyceride levels present in long-lived families compared to controls (Vaarhorst A A M, Beekman M, Suchiman E H D, van Heemst D V, Houwing-Duistermaat J J, Westerndorp R G et al (2010) Lipid metabolism in long-lived families: the Leiden Longevity Study. AGE 33:219-227). Preventing and treating dyslipidemia have been highlighted as important to improve quality of life and expand longevity.

Prediabetic and diabetic conditions, including hyperglycemia and insulin resistance, result in impaired quality of life and longevity. From 1999 to 2011, the average number of years lost from diabetes has increased by 46% in men and 44% in women (Gregg E W, Zhuo X, Cheng Y J, Albright A L, Narayan K M V, Thompson T J (2014) Trends in lifetime risk and years of life lost due to diabetes in the USA, 1985-2011: A modelling study. Lancet Diab Endocrinol 2:867-874). Insulin resistance increases with advanced age, and people who live over one hundred years have lower insulin resistance compared to those who were younger (Paolisso G, Barbieri M, Rizzo M R, Carella C, Rotondi M, Bonafe M et al (2001) Low insulin resistance and preserved β-cell function contribute to human longevity but are not associated with TH-INS genes. Exp Gerontol 37:147-156). Treatments long used to treat type 2 diabetes, including metformin, have been demonstrated to expand longevity (Novelle M G, Ali A, Dieguez C, Bernier M, de Cabo R (2016) Metformin: A hopeful promise in aging research. CSH Perspectives 6:a025932), and there is an active effort to discover other compounds that may help treat hyperglycemia and insulin resistance and expand longevity.

The prevalence of chronic liver disease and accompanying cirrhosis and hepatocellular carcinoma have been increasing at an alarming rate, especially in developed countries. This increase is due primarily to nonalcoholic fatty liver disease (NAFLD) associated with the global rise in obesity and metabolic syndrome (including elevated glucose, dyslipidemia, and insulin resistance). Chronic liver disease contributes to morbidity and mortality, and by aiming to decrease liver failure, transplants, and cancer, therapeutics for liver disease can improve quality of life and expand longevity (Lim Y S, Kim W R (2008) The global impact of hepatic fibrosis and end-stage liver disease. Clinics in Liver Dis 12:733-746).

Iron overload and hyperferritinemia with aging can negatively impact quality of life or longevity. Iron accumulates with age in tissues, including the brain (Hirose W, Ikematsu K, and Tsuda R (2003) Age-associated increases in heme oxygenase-1 and ferritin immunoreactivity in the autopsied brain. Legal Med 5:S360-366). Because iron induces oxidative damage to tissues, resulting in age-related diseases, such as Alzheimer's disease, compounds that reduce iron overload and hyperferritinemia have been proposed as therapeutic targets for aging-associated diseases (Bartzokis G, Tishler T A, Lu P H, Villablanca P, Altshuler L L, Carter M et al. (2007) Brain ferritin iron may influence age- and gender-related risks of neurodegeneration. Neurobiol Aging 28:414-423).

Aging skin and poor wound healing can negatively impact quality of life. Aging skin has changes to structure and function that impairs its integrity and ability to heal (Farage M A, Miller K W, Elsner P, Maibach H I (2013) Characteristics of the aging skin. Adv Wound Care 2: doi: 10.1089). Compounds that prevent or correct intrinsic changes with age that influence skin integrity and repair can aid in improving the quality of life.

With respect to aging and pain, over half of people over 65 years old report to have bothersome pain, most of which have pain in multiple sites and have at least two chronic medical conditions such as arthritis, cardiometabolic diseases, and obesity (Patel K V et al. (2013) Prevalence and impact of pain among older adults in the United States: Findings from the 2011 National Health and Aging Trends Study. Pain 154:2649-2657). As such, anti-inflammatory agents, analgesics, and compounds that attenuate cardiometabolic diseases may aid in alleviating pain, including pain associated with aging. As an example, compounds that reduce prostaglandin E2 (PGE2) can aid in reducing inflammation, pain, and fever, including pain caused by osteoarthritis (Lee A S et al. (2013) A current review of molecular mechanisms regarding osteoarthritis and pain. Gene 527: 440-447). Other compounds that reduce inflammation associated with autoimmune diseases, such as rheumatoid arthritis, can attenuate joint inflammation and pain. As an example, interleukin-17A (IL-17a) is an important contributor to autoimmune diseases, including multiple sclerosis and rheumatoid arthritis, and a compound that lowers IL-17A may help to alleviate pain from rheumatoid arthritis (Iwakura Y et al. (2008) The roles of IL-17A inflammatory immune responses and host defense against pathogens. Immunol Rev 226). Further, compounds that reduce chronic systemic inflammation associated with aging and cardio-metabolic diseases may attenuate these diseases and their associated pain.

With respect to aging and allergies, allergies are one of the fastest growing health problems in people aged over 15 years, and 5% to 10% of allergies are affecting elderly people (Martinis M D et al. (2017) Allergy and aging: an old/new emerging health issue. Aging and Dis 8:162-175). Elderly can be at higher risk of allergies due to physiological changes with aging, concurrent diseases, polydrug therapy, and compromised systems, including the dermal, gastrointestinal, and respiratory systems. Interleukin-17A (IL-17a) is an important contributor to allergic responses, including systemic and dermal hypersensitivities and allergic airway inflammation (Iwakura Y et al. (2008) The roles of IL-17A inflammatory immune responses and host defense against pathogens. Immunol Rev 226). As such, compounds that reduce allergy responses, including reduction of IL-17A, can improve the quality of life for people, including the elderly.

With respect to aging and sleep disorders, sleep problems have been reported to affect up to 40% of the elderly population (Vitiello M V (1997) Sleep disorders and aging: understanding the causes. J Gerontol 52A:M189-M191). This high prevalence is attributed, in part, to physiological changes with aging, as well as the presence of chronic disease. Control of chronic conditions, such as pain, have been demonstrated to improve the quality of sleep and resolve insomnia (Monjan A and Foley D (1996) Incidence of chronic insomnia associated with medical and psychosocial factors: an epidemiologic study among older persons. Sleep Res 25:108). Despite growing concern over the use of benzodiazapines and other sedatives, especially among the elderly, people over 60 years old are more likely to receive sedative prescriptions compare to people aged 40 to 59 (Baum C et al. (1986) Drug utilization in the U.S.—1985: Seventh annual review. Rockville, MD: Food and Drug Administration, Center for Drugs and Biologies). As such, use of natural compounds that may help alleviate underlying medical conditions impacting sleep can be used as a first line means of improving the quality of sleep and life. As a potential alternative to sedatives, PGE2 inhibitors, which can be used to reduce inflammation, pain and fevers, may also aid in stemming PGE2's role in stimulating the wake centers near the posterior hypothalamus (Hayaishi O (1991) Molecular mechanisms of sleep-wake regulation: roles of prostaglandins D2 and E2. FASEB J 5:2575-2581).

With respect to aging and gastrointestinal and/or digestive disorders, aging impacts normal digestion, resulting in disorders associated with sensation, inflammation, poor swallowing, imbalanced microbiota, malabsorption, and malnutrition (Shamburek R D and Farrar J T (1990) Disorders of the digestive system in the elderly. New Engl J Med 322: 438-443). People older than 65 years represent 25% of all inflammatory bowel disease hospitalizations, and older age was a significant risk factor for increased mortality and more severe gastrointestinal disease compared to younger patients (Ananthakrishnan A N et al. (2009) Inflammatory bowel disease in the elderly is associated with worse outcomes: a national study of hospitalizations. Inflamm Bowel Dis 15: 182-289). Compounds that lower gastrointestinal inflammation, restore a balanced microbiota and/or improve proper absorption of nutrients may aid in alleviating digestive disorders. Interleukin-17A (IL-17A) is a contributor to chronic intestinal inflammation, and lowering IL-17A secretion may aid in alleviating digestive disorders (Coccia M et al. (2012) IL-1β mediates chronic intestinal inflammation by promoting the accumulation of IL-17A secreting innate lymphoid cells and CD4+Th17 cells. J Exp Med 209:1595).

With respect to aging and skin conditions and/or wound healing, advanced age can impair wound healing (Sgnoc R and Gruber J (2013) Age-related aspects of cutaneous wound healing: a mini review. Gerontol 59:159-164). This impairment can be due to chronic inflammatory conditions present with age, including increases in cytokines, such as IL-6, and chemokines, such as CXCL8 (also called interleukin 8 (IL-8)), which is elevated in psoriasis. There are some differences present in fetal and elderly wound healing, however, that may be beneficial. As an example, fetal and elderly wounds heal with no to little scarring, respectively. This scarless repair may be due to lower levels of decorin and IL-8, an extracellular matrix proteoglycan and chemokine, respectively, observed in fetal tissue (Beanes S R et al. (2001) Down-regulation of decorin, a transforming growth factor-beta modulator, is associated with scarless fetal wound healing. J Pediatr Surg 36:1666-71; Liechty K W (1997) Diminished interleukin-8 (IL-8) production in the fetal wound healing response. J Surg Res 77:80-84). As such, lower levels of IL-6, IL-8, and decorin may help stem inflammation associated with chronic, non-healing wounds and enable this healing to occur with minimal scarring.

Carnitine is an amino acid present in food, primarily in animal sources, but it can also be made endogenously (Kendler B S. Carnitine: an overview of its role in preventive medicine. Prev Med 15:373-390 (1986)). L-carnitine is the bioavailable and biologically active isomer (Rebouche C J. Kinetics, pharmacokinetics, and regulation of L-carnitine and acetyl-L-carnitine metabolism. Ann NY Acad Sci 1033: 30-41 (2004)), and supplementation with L-carnitine has proposed health benefits related to neurological disorders, cardiovascular disease, and obesity (Flanagan, J. L., Simmons, P. A., Vehige, J. Wilcox, M. D. P., Garrett, Q. Role of carnitine in disease. Nutr Metabol 7:30 (2010), Indiveri, C., Iacobazzi, V. Tonazzi, A., Giangregorio, N., Infantino, V. Convertini, P. et al. The mitochondrial carnitine/acylcarnitine carrier: function, structure and physiopathology. Mol Asp Med 32:223-233 (2011)).

Carnitines are almost entirely found within cells, where they can shuttle long-chain fatty acids into mitochondria as long-chain acylcarnitines to enable β-oxidation-generated energy for cellular activities (Flanagan, J. L., Simmons, P. A., Vehige, J. Wilcox, M. D. P., Garrett, Q. Role of carnitine in disease. Nutr Metabol 7:30 (2010)). Higher circulating concentrations of long-chain acylcarnitines have been associated with higher risks of age-related diseases, including inflammation, mitochondrial dysfunction, cardiovascular disease, type 2 diabetes, and osteoarthritis (Jarrell, Z. R., Smith, M. R., Hu, X., Orr, M., Liu, K. H., Quyyumi, A. A. et al. Plasma acylcarnitine levels increase with healthy aging. Aging 12:13555-13570 (2020), Kalim, S., Clish, C. B., Wenger, J., Elmariah, S., Yeh, R. W., et al. A plasma long-chain acylcarnitine predicts cardiovascular morality in incident dialysis patients. J Am Heart Assoc 2:e000542 (2013), Koh, A. S., Gao, F., Liu, J., Fridianto, K. T., Ching, J., Tan, R. S. et al. Metabolomic profile of arterial stiffness in aged adults. Diab Vasc Dis Res 15:74-80 (2018), Kendler B S. Carnitine: an overview of its role in preventive medicine. Prev Med 15:373-390 (1986), Bouchouirab et al. Plasma Palmitoyl-Carnitine (AC16:0) Is a Marker of Increased Postprandial Nonesterified Incomplete Fatty Acid Oxidation Rate in Adults With Type 2 Diabetes, Can J Diabetes 2018 August; 42(4):382-388.e1. doi: 10.1016/j.jcjd.2017.09.002. Epub 2017 Nov. 9, Tootsi, K., Kals, J., Zilmer, M., Paapstel, K., Ottas, A., Martson, A. Medium- and long-chain acylcarnitines are associated with osteoarthritis severity and arterial stiffness in end-stage osteoarthritis patients: a case-control study. Int J Rheum Dis 21:1211-1218 (2018)).

While long-chain acylcarnitines have been shown to increase with age, short and medium odd-chain acylcarnitines, specifically containing C5:0, C7:0 and C9:0, decrease with age; this decrease with age was not noted with long odd-chain acylcarnitines, such as C15:0 and C17:0 (Jarrell et al. Plasma acylcarnitine levels increase with healthy aging, Aging (Albany NY). 2020 Jul. 15; 12(13): 13555-13570).

Pentadecanoic acid (C15:0) is a long, odd-chain saturated fatty acid present in trace levels in dairy fat, as well as some types of plants and fish (Jenkins, B. et al. A review of odd-chain fatty acid metabolism and the role of pentadecanoic acid (C15:0) and heptadecanoic acid (C17:0) in health and disease. Molecules 20:2425-2444 (2015)). Large, prospective cohort studies have repeatedly shown that higher blood concentrations of pentadecanoic acid are associated with lower risks of developing chronic diseases, including type 2 diabetes, cardiovascular disease, and heart failure (Forouhi, N. G. et al. Differences in the prospective association between individual plasma phospholipid saturated fatty acids and incident type 2 diabetes: the EPIC-InterAct case-cohort study. Lancet Diab Endocrinol 14:70146-9 (2014), Trieu, K. et al. Biomarkers of dairy fat intake, incident cardiovascular disease, and all-cause mortality: A cohort study, systematic review, and meta-analysis. PLoS Med 18:e1003763 (2021), Djousse, L. et al. Serum individual nonesterified fatty acids and risk of heart failure in older adults. Cardiology 146:351-358 (2021)). Higher dietary intake and circulating concentrations of pentadecanoic acid have also been associated with lower mortality and greater longevity (Zhuang, P., Cheng, L., Wang, J. & Zhang Y. Saturated fatty acid intake is associated with total mortality in a nationwide cohort study. J Nutrition 149:68-77 (2019), Trieu et al. 2021 Biomarkers of dairy fat intake, incident cardiovascular disease, and all-cause mortality: A cohort study, systematic review, and meta-analysis, PLOS Medicine, Published: Sep. 21, 2021 https://doi.org/10.1371/journal.pmed.1003763, Manca, C., Carta, G, Murru, E., Abolghasemi A, et al. Circulating fatty acids and endocannabiniodome-related mediator profiles associated to human longevity. GeroSci https://doi.org/10.1007/s11357-021-00342-0 (2021)).

Pentadecanoic acid is a dual, partial peroxisome proliferator-activated receptor (PPAR) α/δ agonist and AMP-activated protein kinase (AMPK) activator with demonstrated ability to repair mitochondrial function, improve the stability of red blood cell membranes, and decrease proliferation of breast cancer cells (Venn-Watson, S., Lumpkin, R., Dennis, E. A. Efficacy of dietary odd-chain saturated fatty acid pentadecanoic acid parallels broad associated health benefits in humans: could it be essential? Sci Rep 10:8161 (2020), Fu, W. C. et al. Pentadecanoic acid promotes basal and insulin-stimulated glucose uptake in C2C12 myotubes. Food Nutr Res 65:10.29219/fnr.v65.4527 (2021), To, N. B., Nguyen, Y. T., Moon, J. Y., Ediriweera, M. K., Cho, S. K. Pentadecanoic acid, an odd-chain fatty acid, suppresses the stemness of MCF-7/SC human breast cancer stem-like cells through JAK2/STAT3 signaling. Nutrients 12:1663 (2020)). In human cell systems mimicking various disease states, pentadecanoic acid has both anti-inflammatory and antifibrotic properties (Venn-Watson, S., Lumpkin, R., Dennis, E. A. Efficacy of dietary odd-chain saturated fatty acid pentadecanoic acid parallels broad associated health benefits in humans: could it be essential? Sci Rep 10:8161 (2020)). Further, diet-induced obese mice modeling type 2 diabetes were supplemented daily with oral pentadecanoic acid for approximately 12 weeks and demonstrated lower glucose, cholesterol, body weight gain, and pro-inflammatory cytokines compared to non-supplemented controls (Venn-Watson, S., Lumpkin, R., Dennis, E. A. Efficacy of dietary odd-chain saturated fatty acid pentadecanoic acid parallels broad associated health benefits in humans: could it be essential? Sci Rep 10:8161 (2020)).

Daily pentadecanoic acid supplementation over 11 weeks also lowered inflammation, cholesterol, and triglycerides and attenuated anemia and liver fibrosis in an in vivo model of nonalcoholic fatty liver disease (Venn-Watson, S., Lumpkin, R., Dennis, E. A. Efficacy of dietary odd-chain saturated fatty acid pentadecanoic acid parallels broad associated health benefits in humans: could it be essential? Sci Rep 10:8161 (2020)). Because pentadecanoic acid 1) is an established dietary active fatty acid not readily made by the body, 2) has lower body levels repeatedly associated with poorer cardiometabolic and liver health, and 3) has demonstrated beneficial and pleiotropic activities directly related to cardiometabolic and liver health, pentadecanoic acid has been proposed as an essential fatty acid (Venn-Watson, S., Lumpkin, R., Dennis, E. A. Efficacy of dietary odd-chain saturated fatty acid pentadecanoic acid parallels broad associated health benefits in humans: could it be essential? Sci Rep 10:8161 (2020)).

Bottlenose dolphins (*Tursiops truncatus*) are long-lived, large-brained mammals that develop chronic aging-associated conditions similar to humans, including metabolic syndrome, chronic inflammation, nonalcoholic fatty liver disease, and Alzheimer's disease (Gunn-Moore, D., Kaidanovich-Beilin, O., Iradi, M. C. G., Gunn-Moore, F., Lovestone, S. Alzheimer's disease in humans and other animals: A consequence of post reproductive life span and longevity rather than aging. Alz Dementia 14: 195-204 (2018), Venn-Watson, S., Smith, C. R., Gomez, F., Jensen, E. D. Physiology of aging among healthy, older bottlenose dolphins (*Tursiops truncatus*): comparisons with aging humans. J Comp Physiol 181:667-680 (2011), Venn-Watson, S., Benham, C., Carlin, K., DeRienzo, D., St. Leger, J. Hemochromatosis and fatty liver disease: building evidence for insulin resistance in bottlenose dolphins (*Tursiops truncatus*). J Zoo Wildlf Med 43:10.1638 (2012), Venn-Watson, S., Smith, C. R., Stevenson, S., Parry, C., Daniels, R. Jensen, E., et al. Blood-based indicators of insulin resistance and metabolic syndrome in bottlenose dolphins (*Tursiops truncatus*). Front Endocrinol:10.3389 (2013)). Similar to humans, dolphins with higher circulating odd-chain saturated fatty acid concentrations have a lower risk of metabolic syndrome and liver disease; feeding dolphins a modified diet with fish containing higher odd-chain saturated fatty levels, including C15:0 and C17:0, resulted in a shifted serum metabolome, lower insulin and cholesterol, as well as attenuated anemia (Venn-Watson, S., Baird, M., Novick, B., Parry, C., Jensen, E. D. Modified fish diet shifted serum metabolome and alleviated chronic anemia in bottlenose dolphins (*Tursiops truncatus*): Potential role of odd-chain saturated fatty acids. PLoS ONE doi10.1371/journal.pone.0230769 (2020)).

It is an object of certain of the embodiments to provide a composition comprising pentadecanoylcarnitine or pentadecanoic acid for use in achieving a body concentration of pentadecanoylcarnitine in the subject from about 1 µM to 20 µM. Body concentration can include but is not limited to any in vivo concentration, including blood concentration, plasma concentration, or other bodily fluid concentration. It is an object of certain of the embodiments to provide a composition comprising pentadecanoylcarnitine or pentadecanoic acid for use in treatment of one or more conditions selected from aggression, allergies, allergic rhinitis, Alzheimer's disease, anxiety and anxiety disorders, amyotrophic lateral sclerosis, arthritis, asthma, atherosclerosis, attention-deficit hyperactivity disorder, bipolar disorder, brain damage, cancer, cardiovascular disease, cholestatic pruritis, depression, chronic obstructive pulmonary disease (COPD), cocaine abuse, cough, dermatitis, depression, drug-seeking behavior, gastrointestinal disorders, facial erythema associated with rosacea, glaucoma, hepatic diseases, hyperactive bladder, hypersensitivity disorders, hypertension, impulsivity, inflammation, mental disorders and conditions, metabolic disorders, migraines, nasal and sinus congestion, nausea, neuropathic pain with and symptoms of multiple sclerosis, neurological and neuropsychiatric disorders, obesity, obsessive-compulsive disorders, opioid-induced respiratory depression, osteoarthritis, pain, Parkinson disease, pathological gambling, peptic ulcers, schizophrenia, sleep disorders, spinal cord injury, tardive dyskinesia, tics and behavioral problems with Tourette's syndrome; as well as supporting appetite, cardiovascular health, hematologic health, memory, metabolic health, mood, prolonged REM sleep, renal health, sexuality, sociability and metabolic, hematological, renal, and weight loss.

It is an object of certain of the embodiments to provide a method for detecting protective factors for and risk factors against conditions provided herein, including but not limited to inflammation, anemia, hyperglycemia, dyslipidemia, hyperinsulinemia, liver disease, iron overload, impaired skin integrity, wound healing, scarring, pain, allergies, sleep disorders and problems, and gastrointestinal disorders and problems, and other related conditions in mammal subjects, such as companion animals and humans. An object of certain of the embodiments is to provide a method for treating conditions including but not limited to aging-associated conditions that impact quality of life or longevity in mammal subjects, such as companion animals and humans. An object of certain of the embodiments is to provide a method for detecting conditions including but not limited to aging-associated conditions that impact quality of life or longevity in mammal subjects, such as companion animals and humans. It is an object of certain of the embodiments to provide a method for increasing the serum, plasma, or erythrocyte membrane level of pentadecanoylcarnitine in mammal subjects, such as companion animals and humans. An object of certain of the embodiments is to provide a pentadecanoylcarnitine or pentadecanoic acid supplement or prescription therapeutic for treating or preventing conditions including but not limited to those disclosed herein. An object of certain of the embodiments is to provide a method for detecting and/or treating conditions as disclosed herein in mammal subjects, such as companion animals and humans, which is easy to accomplish in a cost-effective manner.

An object of certain of the embodiments is to provide a method for modulating markers of conditions as disclosed herein in mammal subjects, such as companion animals and humans. An object of certain of the embodiments is to provide a method for detecting conditions as disclosed herein in mammal subjects, such as companion animals and humans. An object of certain of the embodiments is to provide a method for treatment of conditions as disclosed herein in mammal subjects, such as companion animals and humans. An object of certain of the embodiments is to provide a method for prophylaxis of conditions as disclosed herein in mammal subjects, such as companion animals and humans. An object of certain of the embodiments is to provide a method for prophylaxis of a condition provided herein in mammal subjects, such as companion animals and humans.

An object of certain of the embodiments is to provide a method for increasing pentadecanoylcarnitine in the sera, plasma, or erythrocyte membranes of mammal subjects, such as companion animals and humans. An object of certain of the embodiments is to provide a method for detecting or treating conditions as disclosed herein in mammal subjects, such as companion animals and humans. An object of certain of the embodiments is to provide a pentadecanoylcarnitine supplement substantially free from other small molecule metabolites in mammal subjects, such as companion animals and humans.

It is an object of certain of the embodiments to provide a method for detecting and treating conditions as disclosed herein in mammal subjects, such as companion animals and humans. An object of certain of the embodiments is to provide pentadecanoylcarnitine or pentadecanoic acid for treating conditions as disclosed herein in mammal subjects, such as companion animals and humans. An object of certain of the embodiments is to provide a method for prophylaxis of conditions as disclosed herein in mammal subjects, such as companion animals and humans. An object of certain of the embodiments is to provide a method for detecting or treating conditions as disclosed herein in mammal subjects, such as companion animals and humans. An object of certain of the embodiments is to provide pentadecanoylcarnitine as a supplement for treating conditions as disclosed herein, such as in companion animals and humans.

An object of certain of the embodiments is to provide a bioavailable form of pentadecanoylcarnitine or pentadecanoic acid to mammal subjects, such as companion animals and humans. An object of certain of the embodiments is to provide pentadecanoylcarnitine or pentadecanoic acid with one or more other small molecule biochemicals described herein to mammal subjects, such as companion animals and humans. An object of certain embodiments is to provide a method for increasing small pentadecanoylcarnitine or pentadecanoic acid in the sera of mammal subjects, such as companion animals and humans. An object of certain of the embodiments is to provide a method for altering concentrations of pentadecanoylcarnitine or pentadecanoic acid as described herein in the sera, plasma, or erythrocyte membranes of mammal subjects, such as companion animals and humans.

One or more than one of the aforementioned objects is provided by or achieved by the various compositions, methods, and uses as described herein.

Definitions

The term "alcohol" as used herein is a broad term, and is to be given its ordinary and customary meaning to a person of ordinary skill in the art (and is not to be limited to a special or customized meaning), and refers without limitation to any compound as described herein incorporating one or more hydroxy groups, or being substituted by or functionalized to include one or more hydroxy groups.

The term "short-chain fatty acid" as used herein is a broad term, and is to be given its ordinary and customary meaning to a person of ordinary skill in the art (and is not to be limited to a special or customized meaning), and refers without limitation to a fatty acid with 2-6 carbon atoms The term "medium-chain fatty acid" as used herein is a broad term, and is to be given its ordinary and customary meaning to a person of ordinary skill in the art (and is not to be limited to a special or customized meaning), and refers without limitation to a fatty acid with 7-12 carbon atoms.

The term "long-chain fatty acid" as used herein is a broad term, and is to be given its ordinary and customary meaning to a person of ordinary skill in the art (and is not to be limited to a special or customized meaning), and refers without limitation to a fatty acid with 13-22 carbon atoms.

The term "very long chain fatty acid" as used herein is a broad term, and is to be given its ordinary and customary meaning to a person of ordinary skill in the art (and is not to be limited to a special or customized meaning), and refers without limitation to a fatty acid with 23 or more carbon atoms.

The term "derivative" as used herein is a broad term, and is to be given its ordinary and customary meaning to a person of ordinary skill in the art (and is not to be limited to a special or customized meaning), and refers without limitation to any compound as described herein incorporating one or more derivative groups, or being substituted by or functionalized to include one or more derivative groups.

Derivatives include but are not limited to esters, amides, anhydrides, acid halides, thioesters, phosphates, triphosphates, and β-sulfenyl derivatives.

The term "hydrocarbon" as used herein is a broad term, and is to be given its ordinary and customary meaning to a person of ordinary skill in the art (and is not to be limited to a special or customized meaning), and refers without limitation to any moiety comprising only carbon and hydrogen atoms. A functionalized or substituted hydrocarbon moiety has one or more substituents as described elsewhere herein.

The term "lipid" as used herein is a broad term, and is to be given its ordinary and customary meaning to a person of ordinary skill in the art (and is not to be limited to a special or customized meaning), and refers without limitation to saturated and unsaturated oils and waxes, derivatives, amides, glycerides, small molecule metabolites, fatty alcohols, sterol and sterol derivatives, phospholipids, ceramides, sphingolipids, tocopherols, and carotenoids, among others.

The terms "pharmaceutically acceptable" as used herein is a broad term, and is to be given its ordinary and customary meaning to a person of ordinary skill in the art (and is not to be limited to a special or customized meaning), and refers without limitation to those compounds, materials, compositions, and/or dosage forms which are, within the scope of sound medical judgment, suitable for contact with the tissues of and/or for consumption by human beings and animals without excessive toxicity, irritation, allergic response, or other problem complications commensurate with a reasonable risk/benefit ratio.

The terms "pharmaceutically acceptable salts" and "a pharmaceutically acceptable salt thereof" as used herein are broad terms, and are to be given their ordinary and customary meaning to a person of ordinary skill in the art (and is not to be limited to a special or customized meaning), and refer without limitation to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as, for example, The Merck Index. Any suitable constituent can be selected to make a salt of the therapeutic agents discussed herein, provided that it is non-toxic and does not substantially interfere with the desired activity. In addition to salts, pharmaceutically acceptable precursors and derivatives of the compounds can be employed. Pharmaceutically acceptable amides, lower alkyl derivatives, and protected derivatives can also be suitable for use in compositions and methods of preferred embodiments. While it may be possible to administer the compounds of the preferred embodiments in the form of pharmaceutically acceptable salts, it is generally preferred to administer the compounds in neutral form.

The term "pharmaceutical composition" as used herein is a broad term, and is to be given its ordinary and customary meaning to a person of ordinary skill in the art (and is not to be limited to a special or customized meaning), and refers without limitation to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids or bases. Pharmaceutical compositions will generally be tailored to the specific intended route of administration.

The term "carrier" as used herein is a broad term, and is to be given its ordinary and customary meaning to a person of ordinary skill in the art (and is not to be limited to a special or customized meaning), and refers without limitation to a compound that facilitates the incorporation of a compound into cells or tissues. For example, without limitation, dimethyl sulfoxide (DMSO) is a commonly utilized carrier that facilitates the uptake of many organic compounds into cells or tissues of a subject. Water, saline solution, ethanol, and mineral oil are also carriers employed in certain pharmaceutical compositions.

The term "diluent" as used herein is a broad term, and is to be given its ordinary and customary meaning to a person of ordinary skill in the art (and is not to be limited to a special or customized meaning), and refers without limitation to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

The term "excipient" as used herein is a broad term, and is to be given its ordinary and customary meaning to a person of ordinary skill in the art (and is not to be limited to a special or customized meaning), and refers without limitation to a substance that is added to a pharmaceutical composition to provide, without limitation, bulk, consistency, stability, binding ability, lubrication, disintegrating ability etc., to the composition. A "diluent" is a type of excipient.

The term "subject" as used herein is a broad term, and is to be given its ordinary and customary meaning to a person of ordinary skill in the art (and is not to be limited to a special or customized meaning), and refers without limitation to an animal that is the object of treatment, observation or experiment. "Animal" includes cold- and warm-blooded vertebrates and invertebrates such as fish, shellfish, reptiles and, in particular, mammals. "Mammal" includes, without limitation, dolphins, mice, rats, rabbits, guinea pigs, dogs, cats, sheep, goats, cows, horses, primates, such as monkeys, chimpanzees, and apes, and, in particular, humans. In some embodiments, the subject is human.

The terms "treating," "treatment," "therapeutic," or "therapy" as used herein are broad terms, and are to be given their ordinary and customary meaning (and are not to be limited to a special or customized meaning) and, without limitation, do not necessarily mean total cure or abolition of the disease or condition. Any prophylaxis of any undesired markers of a disease or condition, undesired signs of a disease or condition, or undesired symptoms of a disease or condition, to any extent, can be considered treatment and/or therapy. Any alleviation, lessening, lowering, or mitigation of any undesired markers of a disease or condition, undesired signs of a disease or condition, or undesired symptoms of a disease or condition, to any extent, can be considered treatment and/or therapy. Any promoting, supporting, enhancement, boosting, elevating, or improvement of any desired markers, desired physical states, desired physical conditions, desired mental states, desired mental conditions, health states, or health conditions, either in itself, or in association with a disease or condition, to any extent, can be considered treatment and/or therapy. Any modulation of any markers of a disease or condition, a sign of a disease or condition, a symptom of a disease or condition, a physical state, a physical condition, a mental state, a mental condition, a health condition, a health state, an aging condition, or an aging state, either in itself, or in association with a disease or condition, to any extent, can be considered treatment and/or therapy. Modulation can include, but is not limited to, shifting a marker, value, level, or other indicator of a physical, mental, health, or aging state or condition from one indicative of a relatively less healthy state or condition to one indicative of a relatively more healthy state or condition; or shifting a marker, value, level, or other indicator of a physical, mental, or health condition from one associated with a certain risk of a disease or condition to one indicative of a relatively lower risk of a disease or condition; or producing a desired reduction in variability of a marker, value, level, or other indicator of a physical, mental, health, or aging state or condition. Furthermore, treatment may include acts that may worsen the patient's overall feeling of well-being or appearance.

The terms "therapeutically effective amount" and "effective amount" as used herein are broad terms, and are to be given its ordinary and customary meaning to a person of ordinary skill in the art (and are not to be limited to a special or customized meaning), and are used without limitation to indicate an amount of an active compound, or pharmaceutical agent, that elicits the biological or medicinal response indicated. For example, a therapeutically effective amount of compound can be the amount needed to prevent, alleviate or ameliorate markers or symptoms of a condition or prolong the survival of the subject being treated. This response may occur in a tissue, system, animal or human and includes alleviation of the signs or symptoms of the disease being treated. Determination of a therapeutically effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

The term "solvents" as used herein is a broad term, and is to be given its ordinary and customary meaning to a person of ordinary skill in the art (and is not to be limited to a special or customized meaning), and refers without limitation to compounds with some characteristics of solvency for other compounds or means, that can be polar or nonpolar, linear or branched, cyclic or aliphatic, aromatic, naphthenic and that includes but is not limited to: alcohols, derivatives, diesters, ketones, acetates, terpenes, sulfoxides, glycols, paraffins, hydrocarbons, anhydrides, heterocyclics, among others.

Any percentages, ratios or other quantities referred to herein are on a weight basis, unless otherwise indicated.

Small Molecule Metabolites

In addition to pentadecanoylcarnitine or pentadecanoic acid, other small molecule metabolites may be present in compositions or administered to subjects. Small molecule metabolites are low molecular weight (typically less than 900 daltons, but sometimes higher) and can include but are not limited to amino acids, peptides, carbohydrates, cofactors and vitamins, xenobiotics, or lipids (including monohydroxy fatty acids, medium chain fatty acids, long chain fatty acids, very long chain fatty acids, dicarboxylic fatty acids, phosphatidylcholines, phosphatidylethanolamines, lysophospholipids, plasmalogens, lysoplasmalogens, monoacylglycerols, diacylglycerols, sphingomyelins, or ceramides) that can be identified and measured in the body and as provided herein. Small molecule metabolites can originate from ingestion of food or other oral products or produced endogenously. Small molecule metabolites are referred to and described using conventional nomenclature as is employed by one of skill in the art.

When specific compounds or classes of compounds are referred to herein, these compounds or classes of compounds may be produced by metabolic processes (e.g., by administration of a prodrug, or by endogenous production), or may be provided to a patient in a form of a pharmaceutical composition. It is not intended that the term "metabolite" of necessity requires production of a compound by a metabolic process in a patient to be treated. Instead, the compound, identified as a "metabolite" may be administered directly to the patient in a pharmaceutical composition rather than in a prodrug form that yields the compound as a metabolite in vivo. The term "metabolite" is employed as a broad term that is not intended to limit compounds to be administered to a patient to compounds produced by a particular method of synthesis (in vivo from a prodrug versus ex vivo).

A small molecule metabolite may be referred to by various names, for example, 2-methylserine may be referred to as 2-amino-3-hydroxy-2-methylpropanoic acid.

In some embodiments, the small molecule metabolite can be an amino acid, peptide, carbohydrate, cofactor and vitamin, xenobiotic, or lipid as provided herein. In further embodiments, one or more small molecule metabolites can include at least one amino acid, peptide, carbohydrate, cofactor and vitamin, xenobiotic, or lipid as provided herein.

Small molecule metabolites that are ideal candidates as both biomarkers and therapeutics are metabolites that are successfully detected in serum at high nanomolar or micromolar levels that have a low molecular weight (<900 daltons) and meet Lipinski's rule of five. All metabolites provided herein meet these criteria.

In some embodiments, a small molecule metabolite can be an amino acid, including but not limited to 2-methylserine, 4-hydroxyglutamate, N-acetyl-aspartyl-glutamate, 2-pyrrolidinone, trans-urocanate, imidazole proprionate, 1-ribosyl-imidazoleacetate, 5-imidazoleacetate, N-acetyl-histamine, hydantoin 5-prorionic acid, 5-hydroxylysine, 5-aminovalerate, 2-oxoadipate, xanthurenate, methionine sulfone, homocitrulline, trans hydroxyproline, prolyl-hydroxyproline, or guanidinosuccinate. Derivatives can be synthesized by published methods.

In some embodiments, a small molecule metabolite can be a peptide, including but not limited to gamma-glutamyl-glutamine, or gamma-glutamylglycine; a carbohydrate, including but not limited to N6-carboxymethyllysine; a cofactor or vitamin, including N1-methyl-2-pyridone-5-carboxamide, N1-methyl-4-pyridone-3-carboxamide; or a xenobiotic, including but not limited to 2,3-dihydroxyisovalerate. Derivatives can be synthesized by published methods.

In some embodiments, a small molecule metabolite can be a monohyroxy fatty acid, including but not limited to 2-hydroxyocatnoate, 2-hydroxydecanoate, 8-hydroxyoctanoate, 2-hydroxymyristate, or 16-hydroxypalmitate. Derivatives can be synthesized by published methods.

In some embodiments, a small molecule metabolite can be a medium chain fatty acid, e.g., a fatty acid including but not limited to one containing a group such as heptanoate (C7:0, e.g., heptanoic acid), caprylate (C8:0, e.g., caprylic acid), pelargonate (C9:0, e.g., pelargonic acid), undecanoate (C11:0, e.g., undecanoic acid), or 10-undecanoate (C11:1n1, e.g., 10-undecanoic acid); a long chain fatty acid, including but not limited to pentadecanoate (C15:0, e.g., pentadecanoic acid), margarate (C17:0, e.g., margaric acid), 10-heptadecanoate (C17:1n7, e.g., 10-heptadecanoic acid), 10-nonadecanoate (19:1n9, e.g., 10-nonadecanoic acid), C20:0 fatty acid, or C20:2 fatty acid; a very long chain fatty acid, including but not limited to C24:0 fatty acid or C24:1 fatty acid; a branched chain fatty acid, including but not limited to 15-methylpalmitate (i17:0, e.g., methylpalmitic acid), 17-methylstearate (i19:0, e.g., 17-methylstearic acid), or 2-hydroxyphytanate (e.g., 2-hydroxyphytanic acid); or a dicarboxylate fatty acid, including but not limited to dodecadienoate (C12:2, e.g., dodecandioic acid) or docosadioate (C22-DC, e.g., docosadioic acid). Derivatives can be synthesized by published methods.

In some embodiments, a small molecule metabolite can be a part or product of fatty acid metabolism, including but not limited to propionylglycine, lignoceroylcarnitine (C24), cerotoylcarnitine (C26), N-palmitoylglycine, cis-4-decenoylcarnitine (C10:1), behenoylcarnitine (C22), pentadecanoylcarnitine (C15), or arachidonoylcholine. Derivatives can be synthesized by published methods.

In some embodiments, a small molecule metabolite can be a phosphatidylcholine, including but not limited to 1-stearoyl-2-arachidonoyl-GPC (18:0/20:4), 1-palmitoyl-2-arachidonoyl-GPC (16:0/20:4n6), PC (18:2/22:4), PC (20:0/14:1), PC (20:0/20:3), or PC (20:0/22:4); a phosphatidylethanolamine, including but not limited 1-palmitoyl arachidonoyl-GPE (16:0/20:4), 1-stearoyl-2-arachidonoyl-GPE (18:0/20:4), or PE (16:0/16:0); a phosphatidylserine, including but not limited to 1-stearoyl-2-oleoyl-GPS (18:0/18:1); a lysophospholipid, including but not limited 1-arachidonoyl-GPC (20:4n6), 1-lignoceroyl-GPC (24:0), or 1-arachidonoyl-GPE (20:4n6). Derivatives can be synthesized by published methods.

In some embodiments, a small molecule metabolite can be a plasmalogen, including but not limited to 1-(1-enyl-palmitoyl)-2-arachidonoyl-GPE (P-16:0/20:4), 1-(1-enyl-palmitoyl)-2-oleoyl-GPC (P-16:0/18:1), 1-(1-enyl-palmitoyl)-2-arachidonoyl-GPC (P-16:0/20:4), or 1-(1-enyl-stearoyl)-2-arachidonoyl-GPE (P-18:0/20:4); or a lysoplasmalogen, including but not limited to 1-(1-enyl-palmitoyl)-GPC (P-16:0). Derivatives can be synthesized by published methods.

In some embodiments, a small molecule metabolite can be a monoacylglycerol (MAG), including but not limited to MAG (12:0), MAG (17:0), MAG (20:0), MAG (20:2), 1-arachidonylglycerol (20:4) or 1-heptadecenoylglycerol (17:1); or a diacylglycerol (DAG), including but not limited to DAG (14:1/18:1), stearoyl-arachidonoyl-glycerol (18:0/20:4) [2], oleoyl-arachidonoyl-glycerol (18:1/20:4) [1], or oleoyl-arachidonoyl-glycerol (18:1/20:4) [2]. Derivatives can be synthesized by published methods.

In some embodiments, a small molecule metabolite can be a sphingomyelin, including but not limited to stearoyl sphingomyelin (d18:1/18:0), behenoyl sphingomyelin (d18:1/22:0), tricosanoyl sphingomyelin (d18:1/23:0), lignoceroyl sphingomyelin (d18:1/24:0), sphingomyelin (di 8:2/23:1), sphingomyelin (di 8:2/24:2), sphingomyelin (di 7:1/14:0, d16:1/15:0), sphingomyelin (d17:1/16:0, d18:1/15:0, d16:1/17:0), sphingomyelin (d17:2/16:0, d18:2/15:0), sphingomyelin (d18:1/17:0, d17:1/18:0, d19:1/16:0), sphingomyelin (d18:1/19:0, d19:1/18:0), sphingomyelin (d18:1/21:0, d17:1/22:0, d16:1/23:0), sphingomyelin (d18:2/21:0, d16:2/23:0), or sphingomyelin (d18:2/23:0, d18:1/23:1, d17:1/24:1). Derivatives can be synthesized by published methods.

In some embodiments, a small molecule metabolite can be a ceramide, including but not limited to CER (14:0), HCER (26:1), or LCER (26:0). Derivatives can be synthesized by published methods.

In some embodiments, a derivative of a small molecule metabolite can be a (3-sulfenyl derivative. It is thought that β-sulfenyl derivatives, such as an acid or ester, can be resistant to β-oxidation in the body. Derivatives can be synthesized by published methods.

In some embodiments, a small molecule metabolite is provided in a bioavailable form. The term "bioavailability" refers to the fraction of an administered dose of unchanged drug that reaches the systemic circulation, one of the principal pharmacokinetic properties of drugs. By definition, when a medication is administered intravenously, its bioavailability is 100%. As employed herein, the term "bioavailable" refers to a form of the small molecule metabolite that is successfully absorbed by the body when using methods of administration other than intravenous, for example, an oral therapeutic). In some embodiments, small molecule metabolite-based compositions may include adaptions that optimize absorption.

A pure or purified small molecule metabolite may exist in various physical states. For example, 4-hydroxyglutamate exists as a white powder that is stable at room temperature; this compound can be purchased in forms suitable for research purposes in small amounts from some commercial suppliers (for example, from Sigma-Aldrich Corp., of St. Louis, MO). Other small molecule metabolites, or stereoisomers, or solvates, or esters, or salts or other derivatives thereof, may exist as oils, solids, crystalline solids, or gases.

A pentadecanoylcarnitine, pentadecanoic acid, or other small molecule metabolites or the pharmaceutically acceptable salts or derivatives thereof, may be provided in a purity (e.g., a percentage of the compound, or its pharmaceutically acceptable salts, in a bulk form) of at least about 10%, at least about 20%, at least about 30%, at least about 40%, at least about 50%, at least about 60%, at least about 70%, at least about 80%, at least about 90%, at least about 95%, at least about 98%, at least about 99%, at least about 99.9%, at least about 99.99%, or substantially pure, wherein substantially pure may include, but not be limited to, a product with impurities at a level such that no physiological effect from the presence of the impurities is detectable. A mixture of small molecule metabolites, such as, for example, an amino acid and/or lipid, or pharmaceutically acceptable salts or derivatives thereof, may be present in a purity of at least about 10%, at least about 20%, at least about 30%, at least about 40%, at least about 50%, at least about 60%, at least about 70%, at least about 80%, at least about 90%, at least about 95%, at least about 98%, at least about 99%, at least about 99.9%, at least about 99.99%, or substantially pure, or ranges including and/or spanning the aforementioned values. The pentadecanoylcarnitine, pentadecanoic acid, or a mixture thereof, or a pharmaceutically acceptable salt thereof, may be free from other small molecule metabolites, singly or taken as a group. In some embodiments, pentadecanoylcarnitine, pentadecanoic acid, or a mixture thereof as provided herein may be substantially free from other species of lipids not included herein.

A pentadecanoylcarnitine, pentadecanoic acid, or small molecule metabolite, such as an amino acid, peptide, carbohydrate, cofactor, vitamins, xenobiotic, or lipid, or a pharmaceutically acceptable salt or derivative thereof, may be from any source. In some embodiments, pentadecanoylcarnitine, pentadecanoic acid, or salts thereof, may be present in natural sources, may be isolated from natural sources, may be semi-synthetic, may be synthetic, or may be a mixture of one or more of these. The pentadecanoylcarnitine, pentadecanoic acid, or salts thereof, may be produced in a laboratory, may be produced in nature, may be produced by enzymatic processes, may be produced by wild microbes, may be produced by genetically modified microbes, may be isolated from animal tissues, may be produced by chemical synthesis, or may be produced by a plurality of these processes.

The pentadecanoylcarnitine, pentadecanoic acid, or small molecule metabolite may be derived from natural sources, e.g., fish oils, or can be synthesized by methods as are known in the art. In some embodiments, the pentadecanoylcarnitine, pentadecanoic acid, or small molecule metabolite may be contaminated with undesired components present in unrefined or unpurified natural products. In such situations, it can be desirable to remove undesired components, or to increase the concentration of desired components using known separation or purification techniques.

In any compound described, all tautomeric forms are also intended to be included. Without limitation, all tautomers of carboxylic groups are intended to be included.

In any compound described herein having one or more double bond(s) generating geometrical isomers that can be defined as E or Z, each double bond may independently be E or Z, or a mixture thereof.

Where compounds disclosed herein have unfilled valencies, then the valencies are to be filled with hydrogens or isotopes thereof, e.g., hydrogen-1 (protium) and hydrogen-2 (deuterium).

The pentadecanoylcarnitine, pentadecanoic acid, or small molecule metabolite, such as an amino acid, peptide, carbohydrate, cofactors and vitamin, xenobiotics, or lipid, as described herein, includes crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

The compounds described herein can be labeled isotopically. In some circumstances, substitution with isotopes such as deuterium may afford certain therapeutic advantages resulting from greater metabolic stability, such as, for example, increased in vivo half-life or reduced dosage requirements. Isotopic substitution may be beneficial in monitoring subject response to administration of a compound, for example, by providing opportunity for monitoring of the fate of an atom in a compound. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Compositions Including Pentadecanoylcarnitine or Pentadecanoic Acid

Formulations including pentadecanoylcarnitine or pentadecanoic acid are provided. It is generally preferred to administer the compounds of the embodiments in oral formulations; however, other routes of administration are also contemplated, such as topical. The formulations are suitable for use as consumer health and wellness products, including over the counter (OTC) products, as well as supplements and foodstuffs.

The compositions of the embodiments may be used in cosmetic, cosmeceutical and general skincare compositions or provided in pharmaceutical compositions.

The compositions of the embodiments can also be employed in the connection with mucous membranes, e.g., the lips and the vaginal mucosa. When applied to the vaginal mucosa, a vaginal applicator can be employed as are commercially available. Suitable applicators can be in a form of a pre-filled syringe, a tube attached to a prefilled squeezable reservoir, a prepackaged wand including a preselected amount of composition, or a universal vaginal applicator including perforations along its length for dispensing the composition through the perforations.

Certain of the compositions can contain further therapeutic agents, e.g., locally acting drugs such as antibacterial drugs, antiprotozoal drugs, antifungal drugs, antiviral drugs, spermicidal agents, prostaglandins, and steroids. Drugs suitable for delivery include bromocriptine, sildenafil, oxytocin, calcitonin, luteinizing hormone-releasing hormone and analogues, insulin, human growth hormone, oxybutynin, and steroids used in hormone replacement therapy or for contraception. Antifungal drugs include clotrimazole, econazole, miconazole, terbinafine, fluconazole, ketoconazole, and amphotericin. Antibiotics include amoxicillin, doxycycline, cephalexin, ciprofloxacin, clindamycin, metronidazole, azithromycin, sulfamethoxazole/trimethoprim, amoxicillin/clavulanate, and levofloxacin. Classes of antibiotics include penicillins, tetracyclines, cephalosporins, quinolones, lincomycins, macrolides, sulfonamides, glycopeptides, aminoglycosides, and carbapenems. Types of hormones include 5-alpha-reductase inhibitors, adrenal cortical steroids, corticotropin, glucocorticoids, mineralocorticoids, adrenal corticosteroid inhibitors, antiandrogens, antidiuretic hormones, antigonadotropic agents, antithyroid agents, inhibitors, calcitonin, estrogen receptor antagonists, gonadotropin-releasing hormone antagonists, growth hormone receptor blockers, growth hormones, insulin-like growth factor, parathyroid hormone and analogs, progesterone receptor modulators, prolactin inhibitors, selective estrogen receptor modulators, sex hormones, androgens and anabolic steroids, contraceptives, estrogens, gonadotropin releasing hormones, gonadotropins, progestins, sex hormone combinations, somatostatin and somatostatin analogs, synthetic ovulation stimulants, and thyroid drugs. Antiviral agents include adamantane antivirals, antiviral boosters, antiviral combinations, antiviral interferons, chemokine receptor antagonist, integrase strand transfer inhibitor, miscellaneous antivirals, neuraminidase inhibitors, NNRTIs, NS5A inhibitors, nucleoside reverse transcriptase inhibitors (NRTIs), protease inhibitors, and purine nucleosides. Drugs for treating skin conditions include acne drugs (isotretinoin), atopic dermatitis drugs (topical steroids), herpes zoster drugs (antivirals such as valacyclovir), hives (antihistamines like loratadine or fexofenadine, omalizumab), sunburn (lidocaine), contact dermatitis (antihistamines, topical steroids), diaper rash (zinc oxide), rosacea (metronidazole, doxycycline, azelaic acid, isotretinoin, beta blockers, estrogen), athlete's foot (antifungals), and basal cell carcinoma (imiquimod, fluorouracil, vismodegib).

The compositions of the embodiments include topical formulations containing at least one excipient. Excipients can include a nonaqueous or aqueous carrier, and one or more agents selected from moisturizing agents, pH adjusting agents, deodorants, fragrances, chelating agents, preservatives, emulsifiers, thickeners, solubilizing agents, penetration enhancers, anti-irritants, colorants, surfactants, beneficial agents, pharmaceutical agents, and other components as known in the art for use in connection with topical formulations for treatment of the skin. The composition can be formulated such that preservatives need not be employed.

To facilitate application, the composition may be provided as an ointment, an oil, a lotion, a paste, a powder, a gel, or a cream. The composition may also include additional ingredients such as a protective agent, an emollient, an astringent, a humectant, a sun screening agent, a sun tanning agent, a UV absorbing agent, an antibiotic agent, an antifungal agent, an antiviral agent, an antiprotozoal agent, an anti-acne agent, an anesthetic agent, a steroidal anti-inflammatory agent, a non-steroidal anti-inflammatory agent, an antipruritic agent, an additional antioxidant agent, a chemotherapeutic agent, an anti-histamine agent, a vitamin or vitamin complex, a hormone, an anti-dandruff agent, an anti-wrinkle agent, an anti-skin atrophy agent, a skin whitening agent, a cleansing agent, and combinations thereof. In a further embodiment, the composition may avoid animal or cellular-based materials to avoid skin irritation. The composition can be applied to the dermis, or to mucous membranes.

Some embodiments include administering the pentadecanoylcarnitine or pentadecanoic acid in topical formulations; however, other routes of administration are also contemplated (e.g., mucosal, subdermal, oral, or the like) in addition to oral administration. Contemplated routes of administration include but are not limited to topical, mucosal, and subcutaneous. Suitable liquid forms include suspensions, emulsions, solutions, and the like. Unit dosage forms can also be provided, e.g., individual packets with a premeasured amount of the formulation, configured for administration to a body part on a predetermined schedule pre-procedure and post-procedure. Unit dosage forms configured for administration twice or three times a day are particularly preferred; however, in certain embodiments it can be desirable to configure the unit dosage form for administration once a day, four times a day, or more.

In some embodiments, the topical and other formulations typically comprise from about 0.001 wt. % or less to about 50 wt. % or more of active ingredient, such as the pentadecanoylcarnitine or pentadecanoic acid or salt thereof, from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, or 45 wt. %, or ranges including and/or spanning the aforementioned values.

Compositions and formulations for topical administration can include transdermal patches, ointments, lotions, creams, gels, drops, sprays, liquids, aerosols, and powders. Conventional pharmaceutical carriers, aqueous, powder or oily bases, thickeners and the like may be employed. In certain applications, an ointment, lotion, cream, gel or similar formulation can be provided that can be applied to the skin using the fingers. Such formulations are typically provided in a squeeze tube or bottle or a pot, or in a roll-on, wherein a ball is secured in the top of a container of the formulation, wherein the ball is permitted to roll. By rolling the ball over the skin surface, liquid in the container is transferred to the skin in a controlled manner. An alternative delivery mechanism includes a container with a perforated lid with a mechanism for advancing an extrudable formulation through the lid. In another form, a gel formulation with sufficient structural integrity to maintain its shape is provided, which is advanced up a tube and applied to the skin (e.g., in a stick form). An advantage of the stick form is that only the formulation contacts the skin in the application process, not the fingers or a portion of a container. A liquid or gel can also be placed using an applicator, e.g., a wand, a sponge, a syringe, or other suitable method.

In some embodiments, the pentadecanoylcarnitine or pentadecanoic acid or salt thereof, can be in combination therapy, or in admixture with a suitable carrier, diluent, or excipient, and can contain auxiliary substances such as wetting or emulsifying agents, pH buffering agents, gelling or viscosity enhancing additives, preservatives, scenting agents, colors, and the like, depending upon the route of administration and the preparation desired. Techniques for formulation and administration of the compounds described herein are known to those skilled in the art. See, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulations include, without limitation, monoglycerides, diglycerides, sulfatides, lysolecithin, phospholipids, saponin, bile acids, and the like. The presence of such additional components can influence the physical state, solubility, stability, rate of release, rate of clearance, and penetration of active ingredients.

The compositions for topical administration comprise the pentadecanoylcarnitine or pentadecanoic acid or salt thereof and a dermatologically acceptable vehicle. The vehicle may be aqueous or nonaqueous. The dermatologically acceptable vehicle used in the topical composition may be in the form of a lotion, a gel, an ointment, a liquid, a cream, or an emulsion. If the vehicle is an emulsion, the emulsion may have a continuous aqueous phase and a discontinuous nonaqueous or oil phase (oil-in-water emulsion), or a continuous nonaqueous or oil phase and a discontinuous aqueous phase (water-in-oil emulsion). When administered topically in liquid or gel form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain coloring and scenting agents.

In certain embodiments, a silicone elastomer (e.g., dimethicone crosspolymer) is employed to increase delivery and penetration of the pentadecanoylcarnitine or pentadecanoic acid or salt thereof, into the skin. The pharmaceutical excipients used in the topical preparations of the compositions may be selected from the group consisting of solvents, emollients and/or emulsifiers, oil bases, preservatives, antioxidants, tonicity adjusters, penetration enhancers and solubilizers, chelating agents, buffering agents, surfactants, one or more polymers, and combinations thereof.

Suitable solvents for an aqueous or hydrophilic topical formulation include water; ethyl alcohol; isopropyl alcohol; mixtures of water and ethyl and/or isopropyl alcohols; glycerin; ethylene, propylene or butylene glycols; DMSO; and mixtures thereof. Suitable solvents for hydrophobic topical formulations include mineral oils, vegetable oils, and silicone oils. If desired, the compositions as described herein may be dissolved or dispersed in a hydrophobic oil phase, and the oil phase may then be emulsified in an aqueous phase comprising water, alone or in combination with lower alcohols, glycerin, and/or glycols. Anhydrous formulations may also be employed; however, in certain embodiments it may be acceptable to provide water based compositions, or to permit a limited amount of water to be present.

Viscosity of the compositions can be maintained at the selected level using a pharmaceutically acceptable thickening agent. Suitable viscosity enhancers or thickeners which may be used to prepare a viscous gel or cream with an aqueous base include sodium polyacrylate, xanthan gum, polyvinyl pyrrolidone, acrylic acid polymer, carragenans, hydroxyethyl cellulose, hydroxypropyl cellulose, methyl cellulose, ethyl cellulose, propyl cellulose, hydroxypropyl methyl cellulose, polyethoxylated polyacrylamides, polyethoxylated acrylates, and polyethoxylated alkane thiols. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the thickening agent selected. An amount is preferably used that will achieve the selected viscosity. Viscous compositions are normally prepared from solutions by the addition of such thickening agents, or by employing a base that has an acceptable level of viscosity.

Suitable emollients include hydrocarbon oils and waxes such as mineral oil, petrolatum, paraffin, ceresin, ozokerite, microcrystalline wax, polyethylene, squalene, perhydrosqualene, silicone oils, triglyceride esters, acetoglyceride esters, such as acetylated monoglycerides; ethoxylated glycerides, such as ethoxylated glyceryl monostearate; alkyl esters of fatty acids or dicarboxylic acids.

Suitable silicone oils for use as emollients include dimethyl polysiloxanes, methyl(phenyl) polysiloxanes, and water-soluble and alcohol-soluble silicone glycol copolymers. Suitable triglyceride esters for use as emollients include vegetable and animal fats and oils including castor oil, safflower oil, cotton seed oil, corn oil, olive oil, cod liver oil, almond oil, avocado oil, palm oil, sesame oil, and soybean oil.

Suitable esters of carboxylic acids or diacids for use as emollients include methyl, isopropyl, and butyl esters of fatty acids. Specific examples of alkyl esters including hexyl laurate, isohexyl laurate, iso-hexyl palmitate, isopropyl palmitate, decyl oleate, isodecyl oleate, hexadecyl stearate, decyl stearate, isopropyl isostearate, dilauryl lactate, myristyl lactate, and cetyl lactate; and alkenyl esters of fatty acids such as oleyl myristate, oleyl stearate, and oleyl oleate. Specific examples of alkyl esters of diacids include diisopropyl adipate, diisohexyl adipate, bis(hexyldecyl) adipate, and diisopropyl sebacate.

Other suitable classes of emollients or emulsifiers which may be used in the topical formulations include fatty acids, fatty alcohols, fatty alcohol ethers, ethoxylated fatty alcohols, fatty acid esters of ethoxylated fatty alcohols, and waxes.

Specific examples of fatty acids for use as emollients include pelargonic, lauric, myristic, palmitic, stearic, isostearic, hydroxystearic, oleic, linoleic, ricinoleic, arachidic, behenic, and erucic acids. Specific examples of fatty alcohols for use as emollients include lauryl, myristyl, cetyl, hexadecyl, stearyl, isostearyl, hydroxystearyl, oleyl, ricinoleyl, behenyl, and erucyl alcohols, as well as 2-octyl dodecanol.

Specific examples of waxes suitable for use as emollients include lanolin and derivatives thereof including lanolin oil, lanolin wax, lanolin alcohols, lanolin fatty acids, isopropyl lanolate, ethoxylated lanolin, ethoxylated lanolin alcohols, ethoxolated cholesterol, propoxylated lanolin alcohols, acetylated lanolin, acetylated lanolin alcohols, lanolin alcohols linoleate, lanolin alcohols recinoleate, acetate of lanolin alcohols recinoleate, acetate of lanolin alcohols recinoleate, acetate of ethoxylated alcohols esters, hydrogenolysates of lanolin, hydrogenated lanolin, ethoxylated hydrogenated lanolin, ethoxylated sorbitol lanolin, and liquid and semi-solid lanolin. Also usable as waxes include hydrocarbon waxes, ester waxes, and amide waxes. Useful waxes include wax esters such as beeswax, spermaceti, myristyl myristate and stearyl stearate; beeswax derivatives, e.g., polyoxyethylene sorbitol beeswax; and vegetable waxes including carnauba and candelilla waxes.

Polyhydric alcohols and polyether derivatives may be used as solvents and/or surfactants in the topical formulations. Suitable polyhydric alcohols and polyethers include propylene glycol, dipropylene glycol, polypropylene glycols 2000 and 4000, poly(oxyethylene-co-oxypropylene) glycols, glycerol, sorbitol, ethoxylated sorbitol, hydroxypropylsorbitol, polyethylene glycols 200-6000, methoxy polyethylene glycols 350, 550, 750, 2000 and 5000, poly[ethylene oxide] homopolymers (100,000-5,000,000), polyalkylene glycols and derivatives, hexylene glycol, 2-methyl-2,4-pentanediol, 1,3-butylene glycol, 1,2,6-hexanetriol, 2-ethyl-1, 3-hexanediol, vicinal glycols having 15 to 18 carbon atoms, and polyoxypropylene derivatives of trimethylolpropane.

Polyhydric alcohol esters may be used as emulsifiers or emollients. Suitable polyhydric alcohol esters include ethylene glycol mono- and di-fatty acid esters, diethylene glycol mono- and di-fatty acid esters, polyethylene glycol (200-6000) mono- and di-fatty acid esters, propylene glycol mono- and di-fatty esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Suitable emulsifiers for use in topical formulations include anionic, cationic, nonionic, and zwitterionic surfactants. Preferred ionic emulsifiers include phospholipids, such as lecithin and derivatives.

The pentadecanoylcarnitine or pentadecanoic acid or salt thereof can be formulated as a liposome. The small molecule metabolite can be a component of the lipid portion of the liposome or can be encapsulated in the aqueous portion of the liposome. The pentadecanoylcarnitine or pentadecanoic acid or salt thereof can also be coformulated with a cyclodextrin. The cyclodextrin can be, for example, hydroxypropyl-β-cyclodextrin or a sulfobutylether cyclodextrin. Lecithin and other phospholipids may be used to prepare liposomes containing active ingredients as described herein. Formation of lipid vesicles occurs when phospholipids such as lecithin are placed in water and consequently form one bilayer or a series of bilayers, each separated by water molecules, once enough energy is supplied. Liposomes can be created by sonicating phospholipids in water. Low shear rates create multilamellar liposomes. Continued high-shear sonication tends to form smaller unilamellar liposomes. Hydrophobic chemicals can be dissolved into the phospholipid bilayer membrane. The lipid bilayers of the liposomes deliver the compositions as described herein.

The topical formulations may contain micelles, or an aggregate of surfactant molecules dispersed in an aqueous solution. Micelles may be prepared by dispersing an oil solvent in an aqueous solution comprising a surfactant, where the surfactant concentration exceeds the critical micelle concentration. The resulting formulation contains micelles, i.e., spherical oil droplets surrounded by a membrane of polar surfactant molecules, dispersed in the aqueous solvent.

Sterols including, for example, cholesterol and cholesterol fatty acid esters; amides such as fatty acid amides, ethoxylated fatty acid amides, and fatty acid alkanolamides may also be used as emollients and/or penetration enhancers.

A pharmaceutically acceptable preservative can be employed to increase the shelf life of the composition. Other suitable preservatives and/or antioxidants for use in topical formulations include benzalkonium chloride, benzyl alcohol, phenol, urea, parabens, butylated hydroxytoluene (BHT), butylated hydroxyanisole (BHA), tocopherol, thimerosal, chlorobutanol, or the like, and mixtures thereof, can be employed. If a preservative, such as an antioxidant, is employed, the concentration is typically from about 0.02% to about 2% based on the total weight of the composition, although larger or smaller amounts can be desirable depending upon the agent selected. Reducing agents, as described herein, can be advantageously used to maintain good shelf life of the formulation. It is generally observed that the anhydrous formulations of the embodiments exhibit satisfactory stability, such that a preservative can be omitted from the formulation.

Suitable chelating agents for use in topical formulations include ethylene diamine tetraacetic acid, alkali metal salts thereof alkaline earth metal salts thereof, ammonium salts thereof, and tetraalkyl ammonium salts thereof.

In some embodiments, the carrier may have a pH of between about 4.0 and 10.0. In some embodiments, the carrier may have a pH of between about 6.8 and about 7.8. The pH may be controlled using buffer solutions or other pH modifying agents. Suitable pH modifying agents include phosphoric acid and/or phosphate salts, citric acid and/or citrate salts, hydroxide salts (i.e., calcium hydroxide, sodium hydroxide, potassium hydroxide) and amines, such as triethanolamine. Suitable buffer solutions include a buffer comprising a solution of monopotassium phosphate and dipotassium phosphate, maintaining a pH of between 5.8 and 8; and a buffer comprising a solution of monosodium phosphate and disodium phosphate, maintaining a pH of between 6 and 7.5. Other buffers include citric acid/sodium citrate, and dibasic sodium phosphate/citric acid. The compositions of the embodiments may be isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. It can be desirable to include a reducing agent in the formulation, such as vitamin C, vitamin E, or other reducing agents as are known in the pharmaceutical arts.

Surfactants can also be employed as excipients, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

When the formulations of the embodiments are administered by subcutaneous injection, it is preferably in the form of a pyrogen-free, parenterally acceptable aqueous solution or oleaginous suspension, emulsion or solution. Suspensions can be formulated according to methods well known in the art using suitable dispersing or wetting agents and suspending agents. The preparation of acceptable aqueous or non-aqueous solutions with suitable properties, e.g., pH, isotonicity, stability, and the like, is within the skill in the art. For example, an isotonic vehicle such as 1,3-butanediol, water, isotonic sodium chloride solution, Ringer's solution, dextrose solution, dextrose and sodium chloride solution, lactated Ringer's solution, or other vehicles as are known in the art can be employed, or a fixed oil can be employed conventionally as a solvent or suspending medium, e.g., synthetic mono or diglycerides, fatty acids, or the like. The formulations can also contain stabilizers, preservatives, buffers, antioxidants, or other additives known to those of skill in the art.

In certain embodiments, it can be advantageous to include additional agents having pharmacological activity. Anti-infective agents include, but are not limited to, anthelmintic (mebendazole), antibiotics including aminoglycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin, clindamycin, colistimethate sodium, polymyxin b sulfate, vancomycin, antivirals including acyclovir, amantadine, didanosine, efavirenz, foscarnet, ganciclovir, indinavir, lamivudine, nelfinavir, ritonavir, saquinavir, stavudine, valacyclovir, valganciclovir, zidovudine, quinolones (ciprofloxacin, levofloxacin), sulfonamides (sulfadiazine, sulfisoxazole), sulfones (dapsone), furazolidone, metronidazole, pentamidine, sulfanilamidum crystallinum, gatifloxacin, and sulfamethoxazole/trimethoprim. Anesthetics can include, but are not limited to, ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and phenazopyridine. Anti-inflammatory agents include but are not limited to, nonsteroidal anti-inflammatory drugs (NSAIDs) such as aspirin, celecoxib, choline magnesium trisalicylate, diclofenac potassium, diclofenac sodium, diflunisal, etodolac, fenoprofen, flurbiprofen, ibuprofen, indomethacin, ketoprofen, ketorolac, melenamic acid, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinonide, betamethasone dipropionate, betamethasone valerate, desonide, desoximetasone, fluocinolone, triamcinolone, clobetasol propionate, and dexamethasone.

In certain embodiments, the addition of emollients, emulsion stabilizers, moisturizers, excipients, and other compounds may be modified to enhance the sensory properties of the topical compositions, including but not limited to: skin feel (silkiness, lightness, creaminess, etc.), absorbency (required time at which product loses wet feel and is no longer perceived on skin), consistency, firmness, spreadability (e.g. viscosity, flow onset, shear rates), stickiness, integrity of shape, glossiness, hydrophilicity or hydrophobicity, and others.

In certain embodiments systemic administration of the pentadecanoylcarnitine or pentadecanoic acid can be desirable. In such embodiments, the pentadecanoylcarnitine or pentadecanoic acid or salt thereof are formulated into a composition suitable for oral administration, but other routes of administration are also contemplated.

The compositions described herein can be administered by themselves to a subject, or in compositions where they are mixed with other active agents, as in combination therapy, or with carriers, diluents, excipients or combinations thereof. Formulation is dependent upon the route of administration chosen. Techniques for formulation and administration of the compounds described herein are known to those skilled in the art (see, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively).

The compositions disclosed herein may be manufactured into administrable forms by a process that is itself known, e.g., by means of conventional mixing, dissolving, granulating, dragee-making, levigating, emulsifying, encapsulating, entrapping, tableting, or extracting processes. Many of the compounds used in the pharmaceutical combinations disclosed herein may be provided as salts with pharmaceutically acceptable counterions.

Multiple techniques of administering pentadecanoylcarnitine or pentadecanoic acid or salt thereof exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Contemplated herein is any combination of the forgoing, or other methods as would be known to one of ordinary skill in the art (see, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively).

In practice, the pentadecanoylcarnitine or pentadecanoic acid or salt thereof may be combined as the active ingredient in intimate admixture with a pharmaceutical carrier according to conventional pharmaceutical compounding techniques. The pentadecanoylcarnitine or pentadecanoic acid or salt thereof can be added directly to, e.g., a gelatin capsule or a softgel capsule for consumption by the patient. In other embodiments, carriers can be employed. The carrier can take a wide variety of forms depending on the form of preparation desired for administration. Thus, the compositions provided herein can be presented as discrete units suitable for oral administration such as capsules, cachets or tablets each containing a predetermined amount of the active ingredient. Further, the compositions can be presented as an oil, a powder, as granules, as a solution, as a suspension in an aqueous liquid, as a non-aqueous liquid, as an oil-in-water emulsion, or as a water-in-oil liquid emulsion, similar to the topical formulations described elsewhere herein, but using components suitable for human consumption. In addition to the common dosage forms set out above, the compositions provided herein can also be administered by controlled release and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredients with liquid carriers or finely divided solid carriers or both. The product can then be conveniently shaped into the desired presentation.

A formulation may also be administered in a local rather than systemic manner, for example, via injection of the composition directly into a target area, e.g., in a depot or sustained release formulation. Furthermore, a targeted drug delivery system for the composition may be used, for example, in a liposome coated with a tissue specific antibody.

The compositions may contain the pentadecanoylcarnitine or pentadecanoic acid or salt thereof in an amount effective for the desired therapeutic effect. In some embodiments, the compositions are in a unit dosage form and comprise from about 0.1 mg or less to about 5000 mg or more of pentadecanoylcarnitine or pentadecanoic acid or salt thereof per unit dosage form. In further embodiments, the compositions comprise from about 1 to about 500 mg per unit dosage form or from about 500 to 5000 mg per unit dosage form of pentadecanoylcarnitine or pentadecanoic acid or salt thereof. Such dosage forms may be solid, semisolid, liquid, an emulsion, or adapted for delivery via aerosol or the like for inhalation administration.

The carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, lower alcohols, and water. Examples of gaseous carriers include carbon dioxide and nitrogen.

The compositions provided herein can be prepared as solutions or suspensions of the pentadecanoylcarnitine or pentadecanoic acid or salt thereof in water or nonaqueous liquids. A suitable surfactant can be included such as, for example, hydroxypropylcellulose. Dispersions can also be prepared in glycerol, liquid polyethylene glycols, and mixtures thereof in oils. Further, a preservative can be included to, for example, prevent the detrimental growth of microorganisms.

Compositions provided herein suitable for injectable use include sterile aqueous solutions or dispersions. Furthermore, the compositions can be in the form of sterile powders for the extemporaneous preparation of such sterile injectable solutions or dispersions. The compositions may be stable under the conditions of manufacture and storage; thus, may be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

In addition to the aforementioned carrier ingredients, the formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood or other bodily fluids of the intended recipient. Compositions containing a compound provided herein, or pharmaceutically acceptable salt or derivative thereof, can also be prepared in powder or liquid concentrate form for dilution.

Contemplated herein are compositions including the pentadecanoylcarnitine or pentadecanoic acid or salt thereof as described herein in combination with at least one additional active agent. The pentadecanoylcarnitine or pentadecanoic acid or salt thereof and the at least one additional active agent(s) may be present in a single formulation or in multiple formulations provided together, or may be unformulated. In some embodiments, the pentadecanoylcarnitine or pentadecanoic acid or salt thereof can be administered with one or more additional agents together in a single composition. For example, the pentadecanoylcarnitine or pentadecanoic acid or salt thereof can be administered in one composition, and at least one of the additional agents can be administered in a second composition. In a further embodiment, the pentadecanoylcarnitine or pentadecanoic acid or salt thereof and the at least one additional active agent(s) are co-packaged in a kit. For example, a drug manufacturer, a drug reseller, a physician, a compounding shop, or a pharmacist can provide a kit comprising the pentadecanoylcarnitine or pentadecanoic acid or salt thereof in combination with another product or component for delivery to a patient. Such additional components can include anti-infective agents, anti-inflammatory agents, anesthetics, or the like.

Some embodiments described herein relate to oral compositions of pentadecanoylcarnitine or pentadecanoic acid or salt thereof which can include a therapeutically effective amount of the pentadecanoylcarnitine or pentadecanoic acid or salt thereof described herein and a pharmaceutically acceptable carrier, diluent, excipient or combination thereof. The compositions can include the pentadecanoylcarnitine or pentadecanoic acid or salt thereof in an amount for example, ≥1%, ≥2%, ≥3%, ≥4%, ≥5%, ≥6%, ≥7%, ≥8%, ≥9%, ≥10%, ≥20%, ≥30%, ≥40%, ≥50%, ≥60%, ≥70%, ≥80%, ≥90%, ≥95%, ≥98% of the composition or ranges including and/or spanning the aforementioned values. In some embodiments, the pharmaceutical composition can include pentadecanoylcarnitine or pentadecanoic acid or salt thereof and one or more other small molecule metabolites, such as one or more of an amino acid, peptide, carbohydrate, cofactor, vitamins, xenobiotic, and/or lipid described herein, or salts or derivatives thereof in, for example, ≥1%, ≥2%, ≥3%, ≥4%, ≥5%, ≥6%, ≥7%, ≥8%, ≥9%, ≥10%, ≥20%, ≥30%, ≥40%, ≥50%, ≥60%, ≥70%, ≥80%, ≥90%, ≥95%, ≥98% of the composition, or ranges including and/or spanning the aforementioned values.

Foodstuffs

Foodstuffs and other comestibles including pentadecanoylcarnitine or pentadecanoic acid, or a salt thereof, are provided, wherein an amount of the pentadecanoylcarnitine or pentadecanoic acid, or a salt thereof in the foodstuff has been fortified (e.g., enriched or concentrated). Pentadecanoylcarnitine or pentadecanoic acid, or a salt thereof may be added to foodstuffs for consumption by a subject. The pentadecanoylcarnitine or pentadecanoic acid, or a salt thereof may be integrated into one or more ingredients of a foodstuff. The pentadecanoylcarnitine or pentadecanoic acid, or a salt thereof may be prepared as an ingredient, or may be unprepared. The pentadecanoylcarnitine or pentadecanoic acid, or a salt thereof, or preparation including the pentadecanoylcarnitine or pentadecanoic acid, or a salt thereof, may be added prior to preparation, during preparation, or following preparation. Preparation may without limitation include cooking, mixing, flavoring, seasoning, blending, boiling, frying, baking, or other processes known in the art. Fortification is preferably at a level so as to provide a therapeutic daily dosage of pentadecanoylcarnitine or pentadecanoic acid, or a salt thereof as described elsewhere herein, or to achieve a body concentration of pentadecanoylcarnitine as described herein; however, beneficial effects may also be obtained at amounts below such dosages. Pentadecanoylcarnitine or pentadecanoic acid, or a salt thereof can be administered as a dietary supplement in a unit dosage form (a tablet, a capsule, an encapsulated pill, or gelcap pill), or in a dispensable form of an oral or injectable liquid suspension or solution, a spray, an aerosol, powder, or granules), or as a dietary supplement, additive, ingredient, or fortifier added to a comestible substance (food or beverage). In certain embodiments, pentadecanoylcarnitine or pentadecanoic acid, or a salt thereof as a dietary supplement or food/beverage ingredient or additive can be utilized to promote or support health, e.g., to promote or support metabolic health, to promote or support heart health, to promote or support liver health, to promote or support red blood cell, to promote or support immune health; and/or slow an aging rate. Accordingly, pentadecanoylcarnitine or pentadecanoic acid, or a salt thereof is suitable for administration in those forms and by those methods known in the pharmaceutical and nutraceutical arts, including but not limited to a dietary supplement, a medical food, a food additive, a food ingredient, a food fortifier, a beverage additive, a beverage ingredient, a beverage fortifier, a fortified food, a fortified beverage, an additized food, an additized beverage, as well as pharmaceutical drug in any form, including as a tablet, encapsulated pill, gelcap pill, liquid suspension, liquid solution, spray, or powder.

Pentadecanoylcarnitine or pentadecanoic acid or salt thereof as provided herein may be present as a constituency in foodstuffs by operation of processes known in nature, for example, by altering the metabolic processes of a plant, animal, bacteria, or fungus. Genetic alteration of a plant, animal, bacteria, or fungus to increase the concentration of pentadecanoylcarnitine or pentadecanoic acid or salt thereof, is contemplated. By way of example, the pentadecanoylcarnitine or pentadecanoic acid or salt thereof can be present in the foodstuff in a concentration of at least about 1%, at least about 2%, at least about 3%, at least about 4%, at least about 5%, at least about 6%, at least about 7%, at least about 8%, at least about 9%, at least about 10%, at least about 20%, at least about 30%, at least about 40%, at least about 50%, or higher, for example, 1% to 2% or 3% or 4% or 5% or 6% or 7% or 8% or 9% or 10% or 20% or 30% or 40%, 50%, or ranges including and/or spanning the aforementioned values. The pentadecanoylcarnitine or pentadecanoic acid or salt thereof, if naturally present in a foodstuff, can be present in an enriched amount above that which is naturally occurring for the foodstuff, e.g., a concentration of 10% or more above the average or highest naturally occurring observed concentration, e.g., 20% or 30% or 40% or 50% or 100% or 200% or 300% or 400% or 1000% or 2000% or 5000% or more above the average or highest naturally occurring observed concentration.

Indications

Provided are compositions and methods for treatment, management, amelioration, or prophylaxis of a condition selected from the group consisting of aggression, allergies, allergic rhinitis, Alzheimer's disease, anxiety, anxiety disorders, amyotrophic lateral sclerosis, arthritis, asthma, atherosclerosis, attention-deficit hyperactivity disorder, bipolar disorder, brain damage, cancer, cardiovascular disease, cholestatic pruritis, depression, chronic obstructive pulmonary disease (COPD), cocaine abuse, cough, dermatitis, depression, drug-seeking behavior, gastrointestinal disorders, facial erythema associated with rosacea, glaucoma, hepatic diseases, hyperactive bladder, hypersensitivity disorders, hypertension, impulsivity, inflammation, mental disorders, mental conditions, metabolic disorders, migraines, nasal congestion, sinus congestion, nausea, neuropathic pain with multiple sclerosis, symptoms of multiple sclerosis, neurological disorders, neuropsychiatric disorders, obesity, obsessive-compulsive disorders, opioid-induced respiratory depression, osteoarthritis, pain, Parkinson disease, pathological gambling, peptic ulcers, schizophrenia, sleep disorders, spinal cord injury, tardive dyskinesia, tics with Tourette's syndrome, behavioral problems with Tourette's syndrome.

Provided are compositions and methods for supporting appetite, cardiovascular health, hematologic health, memory, metabolic health, mood, prolonged REM sleep, renal health, sexuality, sociability, metabolic health, hematological health, renal health, and weight loss.

Provided are compositions and methods for achieving a body concentration of pentadecanoylcarnitine of from 1 µM to 20 µM is achieved in a subject.

In some embodiments, levels of serum, plasma, or erythrocyte membrane pentadecanoylcarnitine may increase following administration pentadecanoylcarnitine or pentadecanoic acid or salt thereof.

In some embodiments, the compositions and methods provided herein modulate a marker of aggression, allergies, allergic rhinitis, Alzheimer's disease, anxiety, anxiety disorders, amyotrophic lateral sclerosis, arthritis, asthma, atherosclerosis, attention-deficit hyperactivity disorder, bipolar disorder, brain damage, cancer, cardiovascular disease, cholestatic pruritis, depression, chronic obstructive pulmonary disease (COPD), cocaine abuse, cough, dermatitis, depression, drug-seeking behavior, gastrointestinal disorders, facial erythema associated with rosacea, glaucoma, hepatic diseases, hyperactive bladder, hypersensitivity disorders, hypertension, impulsivity, inflammation, mental disorders, mental conditions, metabolic disorders, migraines, nasal congestion, sinus congestion, nausea, neuropathic pain with multiple sclerosis, symptoms of multiple sclerosis, neurological disorders, neuropsychiatric disorders, obesity, obsessive-compulsive disorders, opioid-induced respiratory depression, osteoarthritis, pain, Parkinson disease, pathological gambling, peptic ulcers, schizophrenia, sleep disorders, spinal cord injury, tardive dyskinesia, tics with Tourette's syndrome, or behavioral problems with Tourette's syndrome, or a marker associated with appetite, cardiovascular health, hematologic health, memory, metabolic health, mood, prolonged REM sleep, renal health, sexuality, sociability, metabolic health, hematological health, renal health, or weight loss. In certain embodiments, the marker is serum, plasma, or red blood cell membrane pentadecanoylcarnitine percentage; serum, plasma, or red blood cell membrane concentration of pentadecanoylcarnitine contained herein; or serum plasma, or red blood cell membrane total pentadecanoylcarnitine. In some embodiments, the pentadecanoylcarnitine is measured as a constituent of glycolipids. In further embodiments, the pentadecanoylcarnitine is measured as a constituent of phospholipids. In still further embodiments, the marker is serum or red blood cell membrane pentadecanoylcarnitine percentage, serum concentration of pentadecanoylcarnitine, or serum total pentadecanoylcarnitine.

In some embodiments, the methods provided herein include the step of measuring the concentration of a marker. One of skill in the art will be able to perform suitable methods for such measurements, including but not limited to those described herein.

Provided herein are methods for treating including the step of administering a dose of pentadecanoylcarnitine or pentadecanoic acid or salt thereof, at a predetermined interval, or at an interval left to the discretion of the subject.

In some embodiments, the compounds and methods provided herein may provide a threshold serum, plasma, or red blood cell membrane percentage of pentadecanoylcarnitine relative to all serum, plasma, or red blood cell membrane small molecule metabolites. For example, the threshold value may be a value of about 0.05% or lower to 90% or higher, e.g., a value of at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1.0%, at least about 1.1%, at least about 1.2%, at least about 1.3%, at least about 1.4%, at least about 1.5%, at least about 1.6%, at least about 1.7%, at least about 1.8%, at least about 1.9%, at least about 2.1%, at least about 2.2%, at least about 2.3%, at least about 2.4%, at least about 2.5%, at least about 2.6%, at least about 2.7%, at least about 2.8%, at least about 2.9%, at least about 3.0%, at least about 3.5%, at least about 4.0%, at least about 4.5%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, more than 90%, or ranges including and/or spanning the aforementioned values.

In some embodiments, the compositions and methods provided herein may provide an increase above a baseline value (e.g., pretreatment value in a patient being treated, or general value observed in a particular patient population) in a serum or plasma concentration of pentadecanoylcarnitine, or red blood cell membrane concentration of pentadecanoylcarnitine. For example, a serum or plasma pentadecanoylcarnitine or red blood cell membrane concentration of pentadecanoylcarnitine may be increased by at least about 1 µg/ml, at least about 2 µg/ml, at least about 3 µg/ml, at least about 4 µg/ml, at least about 5 µg/ml, at least about 6 µg/ml, at least about 7 µg/ml, at least about 8 µg/ml, at least about 9 µg/ml, at least about 10 µg/ml, at least about 15 µg/ml, at least about 20 µg/ml, at least about 25 µg/ml, at least about 30 µg/ml, at least about 35 µg/ml, at least about 40 µg/ml, at least about 45 µg/ml, at least about 50 µg/ml, more than 50 µg/ml, or ranges including and/or spanning the aforementioned values. In some embodiments, the serum concentration of pentadecanoylcarnitine, or red blood cell membrane concentration of pentadecanoylcarnitine may increase above a baseline value (e.g., pretreatment value in a patient being treated, or general value observed in a particular patient population) by at least about $0.01\times10^{-4}$ M, at least about $0.05\times10^{-4}$ M, at least about $0.1\times10^{-4}$ M, at least about $0.2\times10^{-4}$ M, at least about $0.3\times10^{-4}$ M, at least about $0.4\times10^{-4}$ M, at least about $0.5\times10^{-4}$ M, at least about $0.6\times10^{-4}$ M, at least about $0.7\times10^{-4}$ M, at least about $0.8\times10^{-4}$ M, at least about $0.9\times10^{-4}$ M, at least about $1\times10^{-4}$ M, at least about $2\times10^{-4}$ M, at least about $3\times10^{-4}$ M, or ranges including and/or spanning the aforementioned values.

In some embodiments, the compounds and methods provided herein may provide an increase in serum or plasma total pentadecanoylcarnitine and pentadecanoic acid, or red blood cell membrane total pentadecanoylcarnitine and pentadecanoic acid. For example, serum total pentadecanoylcarnitine and pentadecanoic acid, or red blood cell membrane total pentadecanoylcarnitine and pentadecanoic acid, may be increased above a baseline value (e.g., pretreatment value in a patient being treated, or general value observed in a particular patient population) by at least about 5 µg/ml, at least about 6 µg/ml, at least about 7 µg/ml, at least about 8 µg/ml, at least about 9 µg/ml, at least about 10 µg/ml, at least about 15 µg/ml, at least about 20 µg/ml, at least about 25 µg/ml, at least about 30 µg/ml, at least about 35 µg/ml, at least about 40 µg/ml, at least about 45 µg/ml, at least about 50 µg/ml, at least about 60 µg/ml, at least about 70 µg/ml, at least about 80 µg/ml, at least about 90 µg/ml, at least about 100 µg/ml, at least about 150 µg/ml, at least about 200 µg/ml, at least about 250 µg/ml, at least about 300 µg/ml, at least about 350 µg/ml, at least about 400 µg/ml, at least about 450 µg/ml, at least about 500 µg/ml, or more than 500 µg/ml.

In some embodiments, the compounds and methods provided herein may provide an increase above a baseline value (e.g., pretreatment value in a patient being treated, or general value observed in a particular patient population) in a serum, plasma, or red blood cell membrane pentadecanoylcarnitine relative to all serum or red blood cell membrane small molecule metabolites, respectively. For example, a serum, plasma, or red blood cell membrane pentadecanoylcarnitine may be increased above a baseline value (e.g., pretreatment value in a patient being treated, or general value observed in a particular patient population) by at least about 0.01%, at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.1%, at least about 1.2%, at least about 1.3%, at least about 1.4%, at least about 1.5%, at least about 1.6%, at least about 1.7%, at least about 1.8%, at least about 1.9%, at least about 2%, at least about 2.1%, at least about 2.2%, at least about 2.3%, at least about 2.4%, at least about 2.5%, at least about 2.6%, at least about 2.7%, at least about 2.8%, at least about 2.9%, at least about 3%, at least about 3.5%, at least about 4%, at least about 4.5%, at least about 5%, more than 5%, or ranges including and/or spanning the aforementioned values.

In some embodiments, pentadecanoylcarnitine or pentadecanoic acid or salt thereof is administered to maintain serum or plasma total percent of pentadecanoylcarnitine above a predetermined threshold value. In further variations, the pentadecanoylcarnitine or pentadecanoic acid or salt thereof is administered to maintain serum phospholipid percent of the pentadecanoylcarnitine above about 0.1%, about 0.2%, about 0.3%, about 0.4%, about 0.5%, about 0.6%, about 0.7%, about 0.8%, about 0.9%, about 1%, about 1.2%, about 1.4%, about 1.6%, about 1.8%, about 2%, about 2.2%, about 2.4%, about 2.6%, or ranges including and/or spanning the aforementioned values.

In some embodiments, the compounds and methods provided herein may provide a threshold serum, plasma, or red blood cell membrane percentage of pentadecanoylcarnitine relative to all serum or red blood cell membrane small molecule metabolites, respectively. For example, the threshold value may be a value of about 0.05% or lower to 90% or higher, e.g., a value of at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1.0%, at least about 1.1%, at least about 1.2%, at least about 1.3%, at least about 1.4%, at least about 1.5%, at least about 1.6%, at least about 1.7%, at least about 1.8%, at least about 1.9%, at least about 2.1%, at least about 2.2%, at least about 2.3%, at least about 2.4%, at least about 2.5%, at least about 2.6%, at least about 2.7%, at least about 2.8%, at least about 2.9%, at least about 3.0%, at least about 3.5%, at least about 4.0%, at least about 4.5%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, more than 90%, or ranges including and/or spanning the aforementioned values.

In some embodiments, the compounds and methods provided herein may provide an increase above a baseline value (e.g., pretreatment value in a patient being treated, or general value observed in a particular patient population) in a serum or plasma concentration of pentadecanoylcarnitine, or red blood cell membrane concentration of a pentadecanoylcarnitine. For example, a serum pentadecanoylcarnitine or red blood cell membrane concentration of pentadecanoylcarnitine may be increased by at least about 0.01 µg/ml, at least about 0.05 µg/ml, at least about 0.1 µg/ml, at least about 0.4 µg/ml, 1 µg/ml, at least about 2 µg/ml, at least about 3 µg/ml, at least about 4 µg/ml, at least about 5 µg/ml, at least about 6 µg/ml, at least about 7 µg/ml, at least about 8 µg/ml, at least about 9 µg/ml, at least about 10 µg/ml, at least about 15 µg/ml, at least about 20 µg/ml, at least about 25 µg/ml, at least about 30 µg/ml, at least about 35 µg/ml, at least about 40 µg/ml, at least about 45 µg/ml, at least about 50 µg/ml, more than 50 µg/ml, or ranges including and/or spanning the aforementioned values. In some embodiments, the serum concentration of pentadecanoylcarnitine, or red blood cell membrane concentration of pentadecanoylcarnitine may increase above a baseline value (e.g., pretreatment value in a patient being treated, or general value observed in a particular patient population) by at least about $0.001\times10^{-4}$ M, at least about $0.005\times10^{-4}$ M, at least about $0.05\times10^{-4}$ M, at least about $0.01\times10^{-4}$ M, at least about $0.05\times10^{-4}$ M, at least about $0.1\times10^{-4}$ M, at least about $0.2\times10^{-4}$ M, at least about $0.3\times10^{-4}$ M, at least about $0.4\times10^{-4}$ M, at least about $0.5\times10^{-4}$ M, at least about $0.6\times10^{-4}$ M, at least about $0.7\times10^{-4}$ M, at least about $0.8\times10^{-4}$ M, at least about $0.9\times10^{-4}$ M, at least about $1\times10^{-4}$ M, at least about $2\times10^{-4}$ M, at least about $3\times10^{-4}$ M, or ranges including and/or spanning the aforementioned values.

In some embodiments, the compounds and methods provided herein may provide an increase in serum or plasma total pentadecanoylcarnitine and pentadecanoic acid or salt thereof, or red blood cell membrane total pentadecanoylcarnitine and pentadecanoic acid or salt thereof. For example, serum total pentadecanoylcarnitine and pentadecanoic acid or salt thereof, or red blood cell membrane total pentadecanoylcarnitine and pentadecanoic acid or salt thereof, may be increased above a baseline value (e.g., pretreatment value in a patient being treated, or general value observed in a particular patient population) by at least about 0.05 µg/ml, at least about 0.1 µg/ml, at least about 0.5 µg/ml, at least about 1 µg/ml, at least about 5 µg/ml, at least about 6 µg/ml, at least about 7 µg/ml, at least about 8 µg/ml, at least about 9 µg/ml, at least about 10 µg/ml, at least about 15 µg/ml, at least about 20 µg/ml, at least about 25 µg/ml, at least about 30 µg/ml, at least about 35 µg/ml, at least about 40 µg/ml, at least about 45 µg/ml, at least about 50 µg/ml, at least about 60 µg/ml, at least about 70 µg/ml, at least about 80 µg/ml, at least about 90 µg/ml, at least about 100 µg/ml, at least about 150 µg/ml, at least about 200 µg/ml, at least about 250 µg/ml, at least about 300 µg/ml, at least about 350 µg/ml, at least about 400 µg/ml, at least about 450 µg/ml, at least about 500 µg/ml, more than 500 µg/ml, or ranges including and/or spanning the aforementioned values.

Combination Therapies

In some embodiments, the pentadecanoylcarnitine or pentadecanoic acid or salt thereof may be used in combination with one or more additional active agents. Examples of additional active agents that can be used in combination include a small molecule metabolite, or a salt or derivative thereof, or a composition that includes a compound of a small molecule metabolite, or a salt or derivative thereof, include, but are not limited to, agents currently used for treating conditions provided herein, and as otherwise known to medical science.

In some embodiments, pentadecanoylcarnitine or pentadecanoic acid or salt thereof, can be used with one, two, three or more additional active agents described herein. Such agents include, but are not limited to, a small molecule metabolite, or a salt or derivative thereof.

In some embodiments, pentadecanoylcarnitine or pentadecanoic acid or salt thereof can be used (for example, administered or ingested) in combination with another agent or agents for treatment, prevention, maintenance, or prophylaxis of a condition provided herein.

Additionally, pentadecanoylcarnitine or pentadecanoic acid or salt thereof can be used in combination with one or more agents selected from Altoprev (lovastatin), Crestor (rosuvastatin), Lescol (fluvastatin), Lipitor (atorvastatin), Livalo (pitavastatin), Pravachol (pravastatin), Zocor (simvastatin), an anti-platelet medication, a beta blocker, an ACE inhibitor, a calcium channel blocker, a diuretic, anticoagulants, aspirin, bile acid sequestrants, Ezetimibe, Fibrates, Glycoprotein IIb/IIIa Receptor Inhibitors, Niacin (Nicotinic Acid), Nitrates, Platelet Inhibitors, Thrombolytics, lisinopril oral, atenolol oral, Bystolic oral, Diovan oral, hydrochlorothiazide oral, metoprolol succinate oral, amlodipine oral, Norvasc oral, Toprol XL oral, Benicar oral, metoprolol tartrate oral, losartan oral, lisinopril-hydrochlorothiazide oral, clonidine HCl oral, Diovan HCT oral, Cozaar oral, propranolol oral, spironolactone oral, Azor oral, carvedilol oral, Coreg oral, Benicar HCT oral, Exforge oral, Avapro oral, Lotrel oral, verapamil oral, furosemide oral, Lasix oral, Hyzaar oral, Tekturna oral, enalapril maleate oral, Micardis oral, losartan-hydrochlorothiazide oral, ramipril oral, Lopressor oral, Altace oral, Micardis HCT oral, Avalide oral, diltiazem oral, triamterene-hydrochlorothiazide oral, labetalol oral, terazosin oral, amlodipine-benazepril oral, hydralazine oral, Atacand oral, benazepril oral, Tribenzor oral, triamterene oral, doxazosin oral, nifedipine oral, Ziac oral, Aldactone oral, Maxzide oral, Cartia XT oral, prazosin oral, Cardizem CD oral, Zestril oral, Dyazide oral, bisoprolol fumarate oral, Tenex oral, Tenormin oral, Coreg CR oral, Prinivil oral, valsartan oral, atenolol-chlorthalidone oral, Edarbyclor oral, benazepril-hydrochlorothiazide oral, ferrous sulfate oral, Ferrlecit intravenous, Feraheme intravenous, Feosol oral, Infed injection, Integra oral, Ferrex 150 Forte oral, Tandem Dual Action oral, Ferrex 150 oral, ferrous gluconate oral, Corvite 150 oral, Integra F oral, NovaFerrum oral, Iron (ferrous sulfate) oral, Vitron-C oral, Folic acid, corticosteroids, rituximab, IVIG, prednisone, methylprednisolone oral, Kenalog injection, Medrol (Pak) oral, Medrol oral, dexamethasone oral, Depo-Medrol injection, prednisolone oral, DexPak 13 Day oral, Solu-Medrol intravenous, hydrocortisone oral, Cortef oral, Deltasone oral, triamcinolone acetonide injection, cortisone oral, cholinesterase inhibitors such as Donepezil (Aricept), Rivastigmine (Exelon), and Galantamine (Razadyne), Memantine, Aricept, Namenda, Namenda XR, Razadyne ER, Alpha E, vitamin E, Hydergine, Namzaric, Dopamine Agonists such as pramipexole (Mirapex), ropinirole (Requip), rotigotine (Neupro patch) and apomorphine (Apokyn), Anticholinergics such as benztropine (Cogentin) and trihexyphenidyl, MAO-B Inhibitors such as (Eldepryl, Zelapar) and rasagiline (Azilect), COMT Inhibitors such as Entacapone (Comtan), Carbidopa/Levodopa (Sinemet®), amantadine, Tetrabenazine (Xenazine), haloperidol (Haldol), chlorpromazine, risperidone (Risperdal), quetiapine (Seroquel), olanzapine (Zyprexa), indomethacin, sulindac, etodolac, mefenamic acid, meclofenamic acid, meclofenamate sodium, flufenamic acid, tolmetin, ketorolac, diclofenac, diclofenac sodium, ibuprofen, naproxen, naproxen sodium, fenoprofen, ketoprofen, flurbiprofen, oxaprozin piroxicam, meloxicam, ampiroxicam, droxicam, lornoxicam, cinnoxicam, sudoxicam, and tenoxicam.

Additionally, pentadecanoylcarnitine or pentadecanoic acid or salt thereof can be used in combination with one or more agents selected from iron dextran, iron sumalate, polysaccharide iron, ferrus fumarate, carbonyl iron, ferrous asparto glycinate, heme iron polypeptide can be sometimes indicated, ferrus bisglycinate as can be the administration of other medicaments such as androgen hormones, such as erythropoietin, folic acid, vitamin B12, vitamin C, succinic acid, niacin, pyridoxine, riboflavin, biotin, thiamine, calcium formate, Aminoxin, Anadrol-50, Chromagen Forte, Epoetin alfa, Epogen, Fe C Tab Plus, FeRiva, FeRivaFA, Ferocon, Ferotrin, Ferralet 90, Ferrex 28, Ferrogels Forte, FoliTab 500, Fumatinic, Hematogen Forte, Hemetab, Integra Plus, Irospan 42/6, Lenalidomide, Maxaron Forte, Myferon 150 Forte, MyKidz Iron, NovaFerrum, Oxymetholone, Procrit, Proferrin-Forte, Pyridoxine, Repliva 21/7, Revlimid, and Tricon.

Dosing

As will be readily apparent to one skilled in the art, the useful in vivo dosage to be administered and the particular mode of administration will vary depending upon the age, weight, the severity of the condition, and mammalian species treated, the particular forms of the compounds employed, and the specific use for which these compounds are employed. The determination of effective dosage levels (the dosage levels necessary to achieve the desired result) can be accomplished by one skilled in the art using routine methods, for example, in vivo studies. Reference may be made to, for example, "Estimating the Maximum Safe Starting Dose in Initial Clinical Trials for Therapeutics in Adult Healthy Volunteers," U.S. Food and Drug Administration, July 2005.

In some embodiments, a method provided herein may comprise administering a therapeutically effective amount of a composition provided herein. In some embodiments, a therapeutically effective amount may be determined by reference to the modulation of a marker of a condition provided herein. In some embodiments, a therapeutically effective amount may be determined by reference to the modulation of a symptom of a condition provided herein. In still other embodiments, reference may be made to established guidelines for the conditions described herein, including, but not limited to, guidelines for the treatment of a condition provided herein including inflammation.

The dosage may vary broadly, depending upon the desired effects and the therapeutic indication, such as marker values. Alternatively, dosages may be based and calculated upon the surface area or weight of the patient, as understood by those of skill in the art. The exact dosage will be determined on a case-by-case basis, or, in some cases, will be left to the informed discretion of the subject. The daily dosage regimen for an adult human patient may be, for example, an oral dose of pentadecanoylcarnitine or pentadecanoic acid, or a salt thereof, or a mixture of pentadecanoylcarnitine and pentadecanoic acid, or salts thereof, from about 0.01 mg to about 10000 mg, from about 1 mg to about 5000 mg, from about 5 mg to about 2000 mg, from about 10 mg to about 1000 mg, from about 50 mg to about 500 mg, or from about 100 mg to about 200 mg. A single dose, e.g., a minimum dose, may include pentadecanoylcarnitine or pentadecanoic acid, or a salt thereof, in about 0.01 mg, about 0.1 mg, about 1 mg, about 5 mg, about 10 mg, about 20 mg, about 50 mg, about 100 mg, about 200 mg, about 300 mg, about 400 mg, about 500 mg, about 600 mg, about 800 mg, about 900 mg, about 1000 mg, about 2000 mg, about 5000 mg, or more, or ranges including and/or spanning the aforementioned values. The dosage may be adjusted according to the body mass of the subject, for example, the dosage, e.g., a minimum dosage, may be about 0.001 mg/kg, about 0.01 mg/kg, about 0.1 mg/kg, 0.3 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 15 mg/kg, about 20 mg/kg, about 25 mg/kg, about 30 mg/kg, or higher or ranges including and/or spanning the aforementioned values. For example, the dosage may be from about 0.001 mg/kg to about 30 mg/kg, from about 0.01 mg/kg to about 10 mg/kg, from about 0.1 mg/kg to about 5 mg/kg, from about 0.3 mg/kg to about 3 mg/kg, or from about 1 mg/kg to about 3 mg/kg. The dosage may be a single one or a series of two or more given in the course of one or more days, as is appropriate for the individual subject. In some embodiments, the pentadecanoylcarnitine or pentadecanoic acid, or a salt thereof will be administered for a period of continuous therapy, for example for about a week or more (e.g., one week, two weeks, three weeks, four weeks, five weeks, six weeks, seven weeks, eight weeks, or more), for several weeks, for about a month or more (e.g., one month, two months, three months, four months, five months, six months, seven months, eight months, nine months, ten months, eleven months, twelve months, or more), for about a year or more, or for a plurality of years. In some embodiments, pentadecanoylcarnitine or pentadecanoic acid, or a salt thereof, can be administered or ingested one time per day, two times per day, three times per day, or more.

As will be understood by those of skill in the art, in certain situations it may be necessary to administer the compounds disclosed herein in amounts that exceed the above-stated, preferred dosage range in order to effectively treat a subject.

Unit dosage forms can also be provided, e.g., individual packages with a premeasured amount of the composition, configured for administration on a predetermined schedule. Unit dosage forms configured for administration one to three times a day are preferred; however, in certain embodiments it may be desirable to configure the unit dosage form for administration more than three times a day, or less than one time per day.

Dosage amount and interval may be adjusted to the individual subject to provide plasma levels of the active moiety which are sufficient to maintain predetermined parameters, indicators, or marker values, or minimal effective concentration (MEC). Dosages necessary to achieve the desired result will depend on individual characteristics and route of administration. However, assays, for example, HPLC assays or bioassays, may be used to determine serum concentrations.

In some embodiments, the compounds and methods provided herein may be used in conjunction with devices and methods of using devices, for example, as provided in U.S. Pat. Nos. 7,651,845; 8,251,904; 8,251,904; 4,985,015; 8,827,957; 4,252,159; 5,318,521; 4,718,430; 9,713,600, 9,707,199, 9,687,461, 9,662,306, 9,561,206, U.S. Publ. No. 2011/0190702; U.S. Publ. No. 2017/0266144, U.S. Publ. No. 2016/0324814, U.S. Publ. No. 2016/0195559, U.S. Publ. No. 2016/0195558, U.S. Publ. No. 2016/0193172, 2 U.S. Publ. No. 016/0193171, U.S. Publ. No. 2016/0193170, WO 2016/111843, DE 2615061; and in conjunction with diagnostic devices, for example, as provided in U.S. Publ. No. 2012/0072236. The contents of each of the foregoing patent documents is incorporated herein by reference in its entirety.

Diagnosis and Monitoring

Provided herein are methods for the diagnosis and monitoring of conditions provided herein.

In some embodiments, the method of diagnosis or monitoring may comprise the step of measuring a percentage of pentadecanoylcarnitine as described herein, in a bodily fluid. In some embodiments, the method of diagnosis or monitoring may comprise the step of measuring a marker of a condition provided herein in a subject. In some embodiments, a correlation between one marker and another may prove instructive. In some embodiments, a condition provided herein may be diagnosed by reference to a threshold level of a marker of the condition, for example, serum pentadecanoylcarnitine percentage, serum concentration of pentadecanoylcarnitine, serum total pentadecanoylcarnitine and pentadecanoic acid, or a ratio between pentadecanoylcarnitine and pentadecanoic acid. For example, the threshold may be determined by reference to a symptom or marker of a condition provided herein.

The percentage of pentadecanoylcarnitine, or a marker of a condition provided herein in a subject may be monitored by any means. Samples for analysis may be derived any fluid or tissue of the subject. For example, from serum, plasma, erythrocyte membranes, urine, and feces.

Example 1

A series of studies were conducted to identify additional serum-based compounds in dolphins, beyond pentadecanoic acid, which were associated with a lower risk of chronic disease indices. Promising compounds were then tested at a variety of concentrations for direct, clinically relevant activities that are known to prevent, manage, treat or cure chronic conditions.

Among bottlenose dolphins fed a modified fish diet containing higher concentrations of C15:0, it was hypothesized that downstream C15:0 metabolites may be contributing to the observed health benefits in this case-control study (Venn-Watson, S., Baird, M., Novick, B., Parry, C., Jensen, E. D. Modified fish diet shifted serum metabolome and alleviated chronic anemia in bottlenose dolphins (*Tursiops truncatus*): Potential role of odd-chain saturated fatty acids. PLoS ONE doi10.1371/journal.pone.0230769 (2020)). To test this hypothesis, changes in the dolphin serum metabolome during Months 0, 1, 3 and 6 were evaluated and compared between dolphins on the baseline and modified fish diet.

Methods

Methods for this modified diet study, including metabolomics, were those previously described (Venn-Watson, S., Baird, M., Novick, B., Parry, C., Jensen, E. D. Modified fish diet shifted serum metabolome and alleviated chronic anemia in bottlenose dolphins (*Tursiops truncatus*): Potential role of odd-chain saturated fatty acids. PLoS ONE doi10.1371/journal.pone.0230769 (2020)), including bioinformatics, principal component analysis, hierarchical clustering, and random forest regression to identify metabolites that best predicted dolphins on the modified versus baseline diet.

Bioinformatics

The informatics system consisted of four major components, the Laboratory Information Management System (LIMS), the data extraction and peak-identification software, data processing tools for QC and compound identification, and a collection of information interpretation and visualization tools for use by data analysts. The hardware and software foundations for these informatics components were the LAN backbone, and a database server running Oracle 10.2.0.1 Enterprise Edition. Peaks were quantified using area-under-the-curve. For studies spanning multiple days, a data normalization step was performed to correct variation resulting from instrument inter-day tuning differences. Essentially, each compound was corrected in run-day blocks by registering the medians to equal one (1.00) and normalizing each data point proportionately (termed the "block correction"). For studies that did not require more than one day of analysis, no normalization is necessary, other than for purposes of data visualization. In certain instances, biochemical data may have been normalized to an additional factor (e.g., cell counts, total protein as determined by Bradford assay, osmolality, etc.) to account for differences in metabolite levels due to differences in the amount of material present in each sample. Two-way ANOVA main effects models, including study group, month, and sex, were used to determine primary drivers of differences in the metabolome.

Principal Components Analysis and Hierarchical Clustering

Each principal component was a linear combination of every metabolite and the principal components were uncorrelated. The number of principal components was equal to the number of observations. The first principal component was computed by determining the coefficients of the metabolites that maximized the variance of the linear combination. The second component found the coefficients that maximize the variance with the condition that the second component was orthogonal to the first. The third component was orthogonal to the first two components and so on. The total variance was defined as the sum of the variances of the predicted values of each component (the variance is the square of the standard deviation), and for each component, the proportion of the total variance was computed. Hierarchical clustering was used as an unsupervised method for clustering the data to show any large-scale differences. Complete clustering using the Euclidean distance was applied, where each sample was a vector with all metabolite values.

Random Forest Regression

Random forest, a supervised classification technique based on an ensemble of decision trees, was used to provide "importance" rank ordering of serum biochemicals that changed due to the modified diet. A random subset of the data with identifying true class information was selected to build the tree ("bootstrap sample" or "training set"), and then the remaining data, the "out-of-bag" (OOB) variables, were passed down the tree to obtain a class prediction for each sample. This process was repeated thousands of times to produce the forest. The final classification of each sample was determined by computing the class prediction frequency ("votes") for the OOB variables over the whole forest. This method was unbiased since the prediction for each sample was based on trees built from a subset of samples that did not include that sample. When the full forest was grown, the class predictions were compared to the true classes, generating the "OOB error rate" as a measure of prediction accuracy. Thus, the prediction accuracy was an unbiased estimate of how well one can predict sample class in a new data set. To determine which biochemicals made the largest contribution to the classification, a "variable importance" measure was computed. The "Mean Decrease Accuracy" (MDA) was used as this metric. The MDA was determined by randomly permuting a variable, running the observed values through the trees, and then reassessing the prediction accuracy.

Results

Figure 1B:
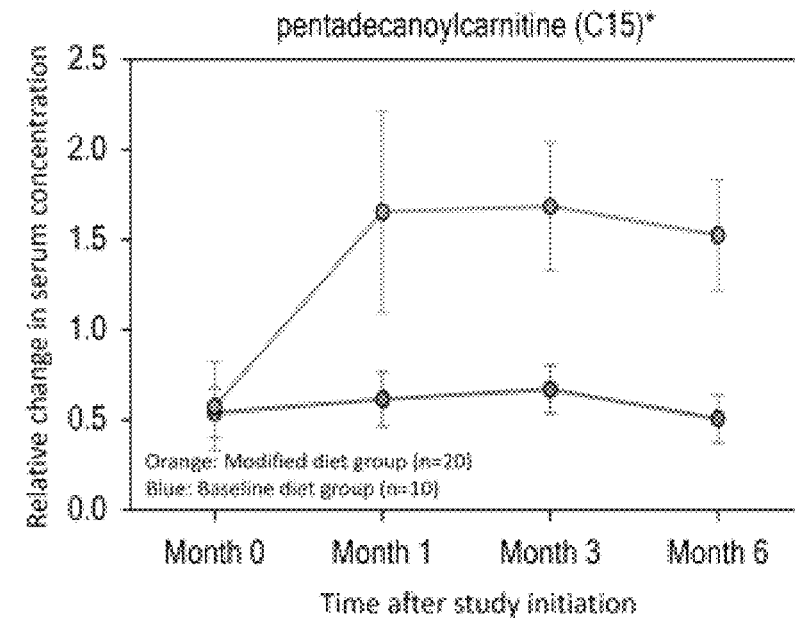
FIG. 1B shows increased pentadecanoylcarnitine concentrations within 1 month on the modified fish diet that was sustained through 6 months.

FIG. 1A shows increased serum pentadecanoic acid (C15:0) and FIG. 1B shows increased pentadecanoylcarnitine concentrations within 1 month on the modified fish diet that was sustained through 6 months. While there were no significant differences in serum C15:0 or pentadecanoylcarnitine concentrations between case and control groups at baseline (Month 0) ($p=0.81$ for C15:0 and $p=0.86$ for pentadecanoylcarnitine) using an ANOVA contrast model, both serum C15:0 and pentadecanoylcarnitine concentrations were higher among case versus control groups at Month 1 ($p<0.0001$ for C15:0 and $p<0.0001$ for pentadecanoylcarnitine), Month 3 ($p<0.0001$ for C15:0 and $p<0.0001$ for pentadecanoylcarnitine), and Month 6 ($p<0.0001$ for C15:0 and $p<0.0001$ for pentadecanoylcarnitine). As outlined in Table 1, both C15:0 (pentadecanoic acid) and pentadecanoylcarnitine were ranked within the top 30 important biochemical predictors of dolphins on the modified fish diet by the first month. Further, as the study moved from Month 1 to Month 6, pentadecanoylcarnitine's ranking increased to become the most important biochemical among dolphins on the modified diet.

TABLE 1

Ranking of biochemical importance in
predicting dolphins on the modified versus baseline diet

| Serum Biochemical | Month 0 | Month 1 | Month 3 | Month 6 |
|---|---|---|---|---|
| Pentadecanoic acid (C15:0) | 0 | $9^{th}$ | $5^{th}$ | $19^{th}$ |
| Pentadecanoylcarnitine | 0 | $25^{th}$ | $2^{nd}$ | $1^{st}$ |

Example 2

Given the observed increase in circulating concentrations of pentadecanoylcarnitine among dolphins on the modified fish diet, it was hypothesized that higher serum pentadecanoylcarnitine concentrations would correlate with changes in clinically relevant indices.

Methods

Methods for this correlation study have been previously described (Venn-Watson, S., Baird, M., Novick, B., Parry, C., Jensen, E. D. Modified fish diet shifted serum metabolome and alleviated chronic anemia in bottlenose dolphins (*Tursiops truncatus*): Potential role of odd-chain saturated fatty acids. PLoS ONE doi10.1371/journal.pone.0230769 (2020)), including Pearson's correlations to evaluate correlations between relative changes in serum pentadecanoylcarnitine concentrations and log-transformed cholesterol, glucose, hemoglobin, red blood cell count, and platelets; and Spearman correlations for glomerular filtration rate and insulin.

Results

Table 2 shows that rising serum pentadecanoylcarnitine concentrations observed in the modified diet study were correlated with lower cholesterol and lower insulin. Rising serum pentadecanoylcarnitine concentrations were correlated with higher hemoglobin, red blood cell count, platelets, and glomerular filtration rate. These data support that increasing serum pentadecanoylcarnitine concentrations may play a role in improving chronic conditions, including hypercholesterolemia, hyperinsulinemia, anemia, thrombocytopenia, and renal disease.

TABLE 2

| Tested Correlations with Serum Pentadecanoylcarnitine Concentrations | Correlation | P-value |
|---|---|---|
| Cholesterol | −0.26 | 0.005 |
| Glucose | 0.02 | 0.87 |
| Hemoglobin | +0.45 | <0.0001 |
| Red blood cell count | +0.44 | <0.0001 |
| Platelets | +0.31 | 0.0006 |
| Glomerular filtration rate | +0.18 | 0.05 |
| Insulin | −0.24 | 0.008 |

Example 3

Given our prior demonstration of C15:0's biologically relevant activities in human cell systems mimicking various chronic disease states, including lowering inflammation and fibrosis (Venn-Watson, S., Lumpkin, R., Dennis, E. A. Efficacy of dietary odd-chain saturated fatty acid pentadecanoic acid parallels broad associated health benefits in humans: could it be essential? Sci Rep 10:8161 (2020)), it was hypothesized that pentadecanoylcarnitine would have similar biologically relevant activities.

Methods

Methods for this human primary cell phenotypic profiling study were those previously described (Venn-Watson, S., Lumpkin, R., Dennis, E. A. Efficacy of dietary odd-chain saturated fatty acid pentadecanoic acid parallels broad associated health benefits in humans: could it be essential? Sci Rep 10:8161 (2020)). Significant activities of pentadecanoylcarnitine were those that were equal to or greater than 0.1|log 10| at 6.7 µM. Biomarkers with significant changes caused by pentadecanoylcarnitine were compared with results from the same study using pentadecanoic acid (C15:0).

Results

Table 3 demonstrates clear differences in primary cell-based activities between pentadecanoylcarnitine and pentadecanoic acid. Of 24 identified biological activities caused by pentadecanoylcarnitine, no specific biomarkers changed significantly in the same direction with pentadecanoic acid.

This study supports that pentadecanoylcarnitine has biologically activities relevant to preventing, managing or treating autoimmune diseases, allergies, asthma, chronic inflammation, cardiovascular disease, oncology, chronic obstructive pulmonary disease, lung inflammation, restenosis, fibrosis, dermatitis, psoriasis, and wound healing that are surprisingly distinct from pentadecanoic acid.

TABLE 3

| Cell System | Disease Biomarker | Representative Disease State | Pentadecanoic acid (C15:0) | Pentadecanoylcarnitine |
|---|---|---|---|---|
| 4H | VEGFR2 | Autoimmunity, allergy, asthma | NS (0.03) | −0.11 |
| LPS | Tissue Factor | Chronic inflammation, cardiovascular disease | NS (0.03) | +0.11 |
| SAg | E-Selectin | Chronic inflammation, autoimmune disease | NS (−0.06) | −0.11 |
|  | B-Cell Proliferation |  | NS (0.04) | −0.17 |
| BT | sIL-6 | Asthma, oncology, autoimmunity, allergy | +0.12 | −0.13 |
|  | sTNF-α |  | +0.14 | −0.10 |
| BE3C | uPAR | COPD, lung inflammation | NS (0.03) | −0.12 |
|  | CXCL10/IP-10 |  | NS (−0.004) | −0.10 |

TABLE 3-continued

| Cell System | Disease Biomarker | Representative Disease State | Pentadecanoic acid (C15:0) | Pentadecanoylcarnitine |
|---|---|---|---|---|
| | CXCL11/I-TAC | | NS (−0.02) | −0.54 |
| | CXCL8/IL-8 | | NS (−0.002) | −0.21 |
| | CXCL9/MIG | | NS (0.001) | −0.60 |
| | HLA-DR | | NS (0.008) | −0.63 |
| | IL-1a | | NS (0.005) | −0.19 |
| | MMP-1 | | NS (−0.02) | −0.27 |
| | MMP-9 | | NS (0.01) | −0.34 |
| | PAI-1 | | NS (0.01) | −0.24 |
| | tPA | | NS (0.03) | −0.43 |
| | uPA | | NS (−0.002) | −0.28 |
| CASM3C | Proliferation | Cardiovascular inflammation, restonosis | NS (−0.04) | +0.10 |
| HDF3CGF | MMP-1 | Fibrosis, chronic inflammation | NS (−0.03) | −0.12 |
| KF3CT | CXCL10/IP-10 | Dermatitis, psoriasis | NS (0.006) | −0.10 |
| MyoF | α-SM Actin | Wound healing, matrix remodeling, fibrosis, chronic inflammation | NS (0.02) | −0.26 |
| /IMphg | MCP-1 | Chronic inflammation, restenosis, cardiovascular disease | NS (0.009) | −0.25 |
| | sIL-10 | | NS (−0.02) | −0.13 |

Example 4

Given demonstration of pentadecanoylcarnitine as a biologically active compound in human cell systems mimicking various disease states, it was hypothesized that pentadecanoylcarnitine would have receptor-based pharmacological activities.
Methods Methods for this study have been previously described (Venn-Watson, S., Lumpkin, R., Dennis, E. A. Efficacy of dietary odd-chain saturated fatty acid pentadecanoic acid parallels broad associated health benefits in humans: could it be essential? Sci Rep 10:8161 (2020)). Significant activities of pentadecanoylcarnitine were those tagged as having maximum pharmacological activities that were greater than or equal to 70% that of the internal control between the concentrations of 1 to 20 µM. Significant pharmacological activities caused by pentadecanoylcarnitine were compared with results from the same assays using pentadecanoic acid (C15:0).
Results Table 4 shows multiple pharmacological activities, at RC50 concentrations between approximately 3 and 10 µM, of pentadecanoylcarnitine, approximately matching maximum activities of positive controls.

Pentadecanoylcarnitine is a cannabinoid receptor 1 and receptor 2 agonist at approximately 1 to 20 µM, further supporting its role in preventing, managing and treating cardiovascular disease, cancer, inflammation, arthritis and cholestatic pruritis (as shown at 6.7 µM in Example 3). Compounds with these activities have also been used or proposed to be used to prevent, manage, or treat nausea, obesity, neuropathic pain with multiple sclerosis, pain, gastrointestinal disorders, atherosclerosis, symptoms of multiple sclerosis, spinal cord injury, Alzheimer's disease, and amyotrophic lateral sclerosis, tics and behavioral problems with Tourette's syndrome, anxiety disorders, attention-deficit hyperactivity disorder, depression, brain damage, tardive dyskinesia, glaucoma, and cough (Pertwee, R. G. Emerging strategies for exploiting cannabinoid receptor agonists as medicines. Br J Pharmacol 156:397-411 (2009), Bryk, M. and Starowicz, K. Cannabinoid-based therapy as a future for joint degeneration. Focus on the role of CB2 receptor in the arthritis progression and pain: an updated review. Pharmacol Rep 73:681-699 (2021)).

The two most potent endogenous cannabinoids (also called endocannabinoids) are anadamide and 2-arachidonoylglyerol (Battista, N., Tommaso, M. D., Bari, M., Maccarrone, M. The endocannabinoid system: an overview. Front Behav Neurosci doi 10.3389/fnbeh.2012.00009 (2012).

Bouchouriab, F. Z., Fortin, M., Noll, C., Dube, J., Carpentier, A. C. Plasma palmitoyl-carnitine (AC16:0) is a marker of increased postprandial nonesterified incomplete fatty acid oxidation rate in adults with type 2 diabetes. Can J Diabetes 42:382-388.e1 (2018)). These compounds bind to an activate both cannabinoid 1 (CB1) and cannabinoid 2 (CB2) receptors found throughout the body, as well as peroxisome proliferator-activated receptors (PPARs). Through these mechanisms, naturally occurring endocannabinoids in the body have demonstrated a wide array of health benefits, including those related to modulating memory, cancer, appetite, fertility, pain, obesity, nausea, osteoarthritis, cardiovascular disease, metabolic disorders, hepatic diseases, inflammation, and neurological and neuropsychiatric disorders (Ligresti, A., Petrosino, S. Di Marzo, V. From endocannabinoid profiling to 'endocannabinoid therapeutics'. Curr Opin Chem Biol 13:21-31 (2009)).

Pentadecanoylcarnitine is a histamine H1 and H2 receptor antagonist at approximately 1 to 20 µM, further supporting its role in preventing, managing and treating allergies, asthma and dermatitis (as shown at 6.7 µM in Example 3). Compounds with these activities have also been used to manage or treat other hypersensitivity disorders and peptic ulcers.

Pentadecanoylcarnitine is a dopamine receptor D1 antagonist at approximately 1 to 20 µM. Compounds with these activities have been used or proposed to be used to prevent, manage, or treat neurological diseases, including Parkinson disease, as well as mental disorders, schizophrenia, cocaine abuse, obesity, pathological gambling, and Tourette's syndrome.

Pentadecanoylcarnitine is an α-2A adrenergic receptor agonist at approximately 1 to 20 µM, further supporting its role in preventing, managing and treating allergic reactions, asthma, nasal and sinus congestion, allergic rhinitis and facial erythema associated with rosacea (as shown at 6.7 µM in Example 3). Compounds with these activities have been used or proposed to be used to support weight loss.

Pentadecanoylcarnitine is a cholinergic receptor muscarinic 1 antagonist at approximately 1 to 20 µM, further supporting its role in preventing, managing and treating allergies, chronic obstructive pulmonary disease (COPD), and asthma (as shown at 6.7 µM in Example 3). Compounds with these activities have been used or proposed to be used to prevent, manage, or treat movement disorders including Parkinson disease, sleep disorders, nausea, inflammatory bowel syndrome spasms, mental disorders, peptic ulcers, hyperactive bladder, and depression.

Pentadecanoylcarnitine is a SERT blocker at approximately 1 to 20 µM. Compounds with these activities have been used or proposed to be used to prevent, manage, or treat depression and obsessive-compulsive disorders.

Pentadecanoylcarnitine is a 5-HT1A receptor agonist at approximately 1 to 20 µM. Compounds with these activities have been used or proposed to be used to regulate mood, sleep, nausea, sexuality and appetite, including increased sociability, decreased impulsivity, facilitation of sex drive and arousal, diminished food intake, and prolonged REM sleep. Compounds that activate this receptor have also been used as a means to prevent, manage, and treat depression, migraines, bipolar disorder, anxiety, hypertension, pain, schizophrenia, Parkinson's disease, aggression, drug-seeking behavior, and opioid-induced respiratory depression.

Pentadecanoylcarnitine is a 5-HT1B receptor agonist at approximately 1 to 20 µM. Compounds with these activities have been used or proposed to be used to manage depression and anxiety, and to reduce of aggression and impulsivity.

In summary, this study has identified pentadecenoyl carnitine as a newly discovered endocannabinoid that fully activates both cannabinoid 1 and 2 receptors at concentrations between 1 and 20 µM.

TABLE 4

| Assay Target | Activity | Result Type | RC50 (µM) C15:0 Acyl-carnitine | RC50 (µM) C15:0 | Max Response (%) Compared to Positive Control C15:0 Acyl-carnitine | Max Response (%) Compared to Positive Control C15:0 | Positive Control | Medical uses |
|---|---|---|---|---|---|---|---|---|
| Cholinergic receptor muscarinic 1 | Antagonist | IC50 | >20 | 10.5 | 0 | 77 | Atropine | Allergies, movement disorders (Parkinson disease), sleep, nausea, IBS spasms, COPD, asthma, antipsychotics, peptic ulcers, overactive bladder, antidepressant |
| Cholinergic receptor muscarinic 2 | Agonist | EC50 | >20 | 3.9 | 2 | 206 | Acetylcholine chloride | Contracts smooth muscles, dilates blood vessels, and slows heart rate |
| Histamine H1 receptor | Antagonist | IC50 | >20 | 10.9 | 5 | 71 | Mepyramine | Allergy, hypersensitivity reactions, pruritic skin disorders |
| Histamine H2 receptor | Antagonist | IC50 | >20 | 6.1 | 2 | 98 | Tiotidine | Peptic ulcers |
| Cannabinoid receptor 1 | Agonist | EC50 | >20 | 3.7 | 25 | 111 | CP 55940 | Nausea, obesity, neuropathic pain with multiple sclerosis |
| Cannabinoid receptor 2 | Agonist | EC50 | >20 | 3.2 | 22 | 106 | CP 55940 | pain, gastrointestinal disorders, atherosclerosis, cardiovascular disease, cancer, symptoms of multiple sclerosis/spinal cord injury/Alzheimer's disease/amyotrophic lateral sclerosis, tics and behavioral problems with Tourette's syndrome, anxiety disorders, attention-deficit hyperactivity disorder, depression, brain damage, tardive dyskinesia, glaucoma, cough, cholestatic pruritis, arthritis, inflammation (Pertwee, R.G. Emerging strategies for exploiting cannabinoid receptor agonists as medicines. Br J Pharmacol 156: 397-411 (2009), Bryk, M. and Starowicz, K. Cannabinoid-based therapy as a future for joint degeneration. Focus on the role of CB2 receptor in the arthritis progression and pain: an updated review. Pharmacol Rep 73: 681-699 (2021)) |
| 5-HT1A receptor | Agonist | EC50 | >20 | 9.6 | 0 | 78 | Serotonin hydrochloride | Regulation of mood, sleep, nausea, sexuality and appetite, including increased sociability, decreased impulsivity, facilitation of sex drive and arousal, diminished |

TABLE 4-continued

| Assay Target | Activity | Result Type | RC50 (μM) C15:0 | RC50 (μM) C15:0 Acyl-carnitine | Max Response (%) Compared to Positive Control C15:0 | Max Response (%) Compared to Positive Control C15:0 Acyl-carnitine | Positive Control | Medical uses |
|---|---|---|---|---|---|---|---|---|
| | | | | | | | | food intake, and prolonged REM sleep. Means to treat depression, migraines, bipolar disorder, anxiety, hypertension, pain, schizophrenia, Parkinson's disease, aggression, drug-seeking behavior, and opioid-induced respiratory depression. |
| 5-HT1B receptor | Agonist | EC50 | >20 | 9.3 | 0 | 74 | Serotonin hydrochloride | Means to manage depression and anxiety, reduction of aggression and impulsivity |
| α-2A adrenergic receptor | Agonist | EC50 | >20 | 5.9 | 22 | 105 | UK 14304 | Hypotension, allergic reactions, asthma, nasal and sinus congestion, allergic rhinitis, facial erythema associated with rosacea, obesity |
| Dopamine receptor D1 | Antagonist | IC50 | >20 | 6.2 | 4 | 105 | SCH 39166 | Antipsychotic, schizophrenia, cocaine abuse, obesity, pathological gambling, Tourette's syndrome |
| Serotonin Transporter | Blocker | IC50 | >20 | 7.4 | 1 | 83 | Clomipramine | Antidepressant, obsessive-compulsive disorder |

Various literature references include teachings related to fatty acid supplementation, including but not limited to Greenberg J A, Bell S J, Ausdal W V. Omega-3 Fatty Acid supplementation during pregnancy. Reviews in obstetrics & gynecology 2008, 1:162-169; Mihalik, S. J., Goodpaster, B. H., Kelley, D. E., Chace, D. H., Vockley, J., Toledo, F. G. S. et al. Increased levels of plasma acylcarnitines in obesity and type 2 diabetes and identification of a marker of glucolipotoxicity. Obesity 18:1695-1700 (2010); Venn-Watson, S., Parry, C., Baird, M., Stevenson, S., Carlin, K., Daniels, R, et al. Increased dietary intake of saturated fatty acid heptadecanoic acid (C17:0) associated with decreasing ferritin and alleviated metabolic syndrome in dolphins. PLoS ONE doi10.1371 (2015); Venn-Watson, S., Smith, C. R., Stevenson, S., Parry, C., Daniels, R. Jensen, E., et al. Blood-based indicators of insulin resistance and metabolic syndrome in bottlenose dolphins (Tursiops truncatus). Front Endocrinol: 10.3389 (2013); Venn-Watson, S., Benham, C., Carlin, K., DeRienzo, D., St. Leger, J. Hemochromatosis and fatty liver disease: building evidence for insulin resistance in bottlenose dolphins (Tursiops truncatus). J Zoo Wildlf Med 43:10.1638 (2012); Venn-Watson, S., Smith, C. R., Gomez, F., Jensen, E. D. Physiology of aging among healthy, older bottlenose dolphins (Tursiops truncatus): comparisons with aging humans. J Comp Physiol 181:667-680 (2011).

Exemplary Compositions, Uses, and Methods

Composition 1: A composition for treatment, management, amelioration, or prophylaxis of a condition selected from the group consisting of aggression, allergies, allergic rhinitis, Alzheimer's disease, anxiety, anxiety disorders, amyotrophic lateral sclerosis, arthritis, asthma, atherosclerosis, attention-deficit hyperactivity disorder, bipolar disorder, brain damage, cancer, cardiovascular disease, cholestatic pruritis, depression, chronic obstructive pulmonary disease (COPD), cocaine abuse, cough, dermatitis, depression, drug-seeking behavior, gastrointestinal disorders, facial erythema associated with rosacea, glaucoma, hepatic diseases, hyperactive bladder, hypersensitivity disorders, hypertension, impulsivity, inflammation, mental disorders, mental conditions, metabolic disorders, migraines, nasal congestion, sinus congestion, nausea, neuropathic pain with multiple sclerosis, symptoms of multiple sclerosis, neurological disorders, neuropsychiatric disorders, obesity, obsessive-compulsive disorders, opioid-induced respiratory depression, osteoarthritis, pain, Parkinson disease, pathological gambling, peptic ulcers, schizophrenia, sleep disorders, spinal cord injury, tardive dyskinesia, tics with Tourette's syndrome, behavioral problems with Tourette's syndrome, the composition comprising: pentadecanoylcarnitine or pentadecanoic acid, or pharmaceutically acceptable salts, solvates, or stereoisomers thereof.

Composition 2: A composition for supporting appetite, cardiovascular health, hematologic health, memory, metabolic health, mood, prolonged REM sleep, renal health, sexuality, sociability, metabolic health, hematological health, renal health, and weight loss, the composition comprising: pentadecanoylcarnitine or pentadecanoic acid, or pharmaceutically acceptable salts, solvates, or stereoisomers thereof.

Composition 3: Composition 1 or 2, comprising pentadecanoylcarnitine.

Composition 4: Composition 1 or 2, comprising pentadecanoic acid.

Composition 5: Composition 1 or 2, comprising pentadecanoylcarnitine and pentadecanoic acid.

Composition 6: Any one of Compositions 1-5, configured for administration of from 0.1 mg to 50 mg, per 1 kg of body weight, optionally from 0.3 mg to 5 mg, per 1 kg of body weight, of the pentadecanoylcarnitine or pentadecanoic acid, or pharmaceutically acceptable salts, solvates, or stereoisomers thereof to a subject in need thereof.

Composition 7: Any one of Compositions 1-6, configured for administration once per day.

Composition 8: Any one of Compositions 1-7, in a unit dosage form comprising from 0.01 mg to 10000 mg, optionally from 10 mg to 200 mg, of the pentadecanoylcarnitine or pentadecanoic acid, or pharmaceutically acceptable salts, solvates, stereoisomers, or esters thereof.

Composition 9: Any one of Compositions 1-7, wherein the composition is in a form selected from the group consisting of a foodstuff, a dietary supplement, a unit dosage form, a prescription drug, or a pharmaceutical drug.

Composition 10: Any one of Compositions 1-7, wherein the composition is in a form selected from the group consisting of a dietary supplement, a medical food, a food additive, a food fortifier, a beverage additive, a beverage fortifier, a fortified food, a fortified beverage, an additized food, and an additized beverage.

Use 11: Use of any one of Compositions 1-10, in the manufacture of a medicament for achieving a body concentration of pentadecanoylcarnitine of from 1 µM to 20 µM.

Method 12: A method of treatment, management, amelioration, or prophylaxis of a condition selected from the group consisting of aggression, allergies, allergic rhinitis, Alzheimer's disease, anxiety, anxiety disorders, amyotrophic lateral sclerosis, arthritis, asthma, atherosclerosis, attention-deficit hyperactivity disorder, bipolar disorder, brain damage, cancer, cardiovascular disease, cholestatic pruritis, depression, chronic obstructive pulmonary disease (COPD), cocaine abuse, cough, dermatitis, depression, drug-seeking behavior, gastrointestinal disorders, facial erythema associated with rosacea, glaucoma, hepatic diseases, hyperactive bladder, hypersensitivity disorders, hypertension, impulsivity, inflammation, mental disorders, mental conditions, metabolic disorders, migraines, nasal congestion, sinus congestion, nausea, neuropathic pain with multiple sclerosis, symptoms of multiple sclerosis, neurological disorders, neuropsychiatric disorders, obesity, obsessive-compulsive disorders, opioid-induced respiratory depression, osteoarthritis, pain, Parkinson disease, pathological gambling, peptic ulcers, schizophrenia, sleep disorders, spinal cord injury, tardive dyskinesia, tics with Tourette's syndrome, behavioral problems with Tourette's syndrome, the method comprising: administering to a subject in need thereof, an effective amount of pentadecanoylcarnitine or pentadecanoic acid, or pharmaceutically acceptable salts, solvates, or stereoisomers thereof.

Method 13: A method of supporting appetite, cardiovascular health, hematologic health, memory, metabolic health, mood, prolonged REM sleep, renal health, sexuality, sociability, metabolic health, hematological health, renal health, and weight loss, the composition comprising: administering to a subject in need thereof, an effective amount of pentadecanoylcarnitine or pentadecanoic acid, or pharmaceutically acceptable salts, solvates, or stereoisomers thereof.

Method 14: Method 12 or 13, wherein a body concentration of pentadecanoylcarnitine of from 1 µM to 20 µM is achieved in the subject.

Method 15: Method 12-14, wherein pentadecanoylcarnitine is administered.

Method 16: Method 12-14, wherein pentadecanoic acid is administered.

Method 17: Method 12-14, wherein pentadecanoylcarnitine and pentadecanoic acid are administered.

Method 18: Method 12-17, wherein from 0.1 mg to 50 mg, per 1 kg of body weight, optionally from 0.3 mg to 5 mg, per 1 kg of body weight, of the pentadecanoylcarnitine or pentadecanoic acid, or pharmaceutically acceptable salts, solvates, or stereoisomers thereof is administered.

Method 19: Method 12-18, wherein pentadecanoylcarnitine or pentadecanoic acid, or pharmaceutically acceptable salts, solvates, or stereoisomers thereof is administered once per day.

Method 20: Method 12-19, wherein pentadecanoylcarnitine or pentadecanoic acid, or pharmaceutically acceptable salts, solvates, or stereoisomers thereof is in a unit dosage form comprising from 0.01 mg to 10000 mg, optionally from 10 mg to 200 mg, of the pentadecanoylcarnitine or pentadecanoic acid, or pharmaceutically acceptable salts, solvates, stereoisomers, or esters thereof.

Method 21: Method 12-20, wherein pentadecanoylcarnitine or pentadecanoic acid, or pharmaceutically acceptable salts, solvates, or stereoisomers thereof is administered in a form selected from the group consisting of a foodstuff, a dietary supplement, a unit dosage form, a prescription drug, or a pharmaceutical drug.

Method 22: Method 12-20, wherein pentadecanoylcarnitine or pentadecanoic acid, or pharmaceutically acceptable salts, solvates, or stereoisomers thereof is administered in a form selected from the group consisting of a dietary supplement, a medical food, a food additive, a food fortifier, a beverage additive, a beverage fortifier, a fortified food, a fortified beverage, an additized food, and an additized beverage.

Dietary Supplement 23: A dietary supplement comprising pentadecanoylcarnitine, or pharmaceutically acceptable salts, solvates, or stereoisomers thereof.

Dietary Supplement 24: Dietary Supplement 23, configured for administration of a minimum of 0.1 mg per 1 kg of body weight, optionally of a minimum of 0.3 mg per 1 kg of body weight, optionally of a minimum of 1 mg per 1 kg of body weight, of the pentadecanoylcarnitine, or pharmaceutically acceptable salts, solvates, or stereoisomers thereof to a subject in need thereof.

Dietary Supplement 25: Any one of Dietary Supplements 23-24, configured for administration of from 0.1 mg to 50 mg, per 1 kg of body weight, optionally from 0.3 mg to 5 mg, per 1 kg of body weight, of the pentadecanoylcarnitine, or pharmaceutically acceptable salts, solvates, or stereoisomers thereof to a subject in need thereof.

Dietary Supplement 26: Any one of Dietary Supplements 23-25, configured for administration once per day.

Dietary Supplement 27: Any one of Dietary Supplements 23-26, in a unit dosage form comprising from 0.01 mg to 10000 mg, optionally from 1 mg to 1000 mg, optionally from 10 mg to 200 mg, of the pentadecanoylcarnitine, or pharmaceutically acceptable salts, solvates, or stereoisomers thereof.

Dietary Supplement 28: Any one of Dietary Supplements 23-27, in a form of a pharmaceutical drug or prescription drug.

Dietary Supplement 29: Any one of Dietary Supplements 23-27, in a form selected from the group consisting of a foodstuff, a medical food, a food additive, a food fortifier, a beverage additive, a beverage fortifier, a fortified food, a fortified beverage, an additized food, and an additized beverage.

Dietary Supplement 30: Any one of Dietary Supplements 23-27, in a form of a foodstuff.

Dietary Supplement 31: Any one of Dietary Supplements 23-27, in a form of a medical food.

Dietary Supplement 32: Any one of Dietary Supplements 23-27, in a form of a food additive.

Dietary Supplement 33: Any one of Dietary Supplements 23-27, in a form of a food fortifier.

Dietary Supplement 34: Any one of Dietary Supplements 23-27, in a form of a beverage additive.

Dietary Supplement 35: Any one of Dietary Supplements 23-27, in a form of a beverage fortifier.

Dietary Supplement 36: Any one of Dietary Supplements 23-27, in a form of a fortified food.

Dietary Supplement 37: Any one of Dietary Supplements 23-27, in a form of a fortified beverage.

Dietary Supplement 38: Any one of Dietary Supplements 23-27, in a form of an additized food.

Dietary Supplement 39: Any one of Dietary Supplements 23-27, in a form of an additized beverage.

Dietary Supplement 40: Any one of Dietary Supplements 23-39, for veterinary use.

Dietary Supplement 41: Any one of Dietary Supplements 23-39, for human use.

Composition 42: A composition substantially as described herein.

Method 43: A method substantially as described herein.

Use 44: A use substantially as described herein.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method of treatment, management, or amelioration of a condition selected from the group consisting of aggression, anxiety, anxiety disorders, attention-deficit hyperactivity disorder, bipolar disorder, brain damage, cholestatic pruritis, depression, cocaine abuse, drug-seeking behavior, facial erythema associated with rosacea, glaucoma, hyperactive bladder, hypertension, impulsivity, mental disorders, mental conditions, migraines, nasal congestion, sinus congestion, obsessive-compulsive disorders, opioid-induced respiratory depression, osteoarthritis, pathological gambling, schizophrenia, spinal cord injury, tardive dyskinesia, tics with Tourette's syndrome, and behavioral problems with Tourette's syndrome, the method comprising:
administering to a subject in need thereof, an effective amount of pentadecanoylcarnitine or a pharmaceutically acceptable salt or solvate thereof.

2. The method of claim 1, wherein a body concentration of pentadecanoylcarnitine of from 1 µM to 20 µM is achieved in the subject.

3. The method of claim 1, wherein pentadecanoylcarnitine or a pharmaceutically acceptable salt thereof is administered.

4. The method of claim 1, wherein from 0.1 mg to 50 mg, per 1 kg of body weight, of the pentadecanoylcarnitine or a pharmaceutically acceptable salt or solvate thereof is administered.

5. The method of claim 1, wherein pentadecanoylcarnitine or a pharmaceutically acceptable salt or solvate thereof is administered once per day.

6. The method of claim 1, wherein pentadecanoylcarnitine or a pharmaceutically acceptable salt or solvate thereof is in a unit dosage form comprising from 0.01 mg to 10000 mg, of the pentadecanoylcarnitine or a pharmaceutically acceptable salt or solvate thereof.

7. The method of claim 1, wherein the condition is selected from the group consisting of aggression, anxiety, anxiety disorders, attention-deficit hyperactivity disorder, cholestatic pruritis, depression, cocaine abuse, drug-seeking behavior, glaucoma, hyperactive bladder, hypertension, impulsivity, mental disorders, mental conditions, migraines, obsessive-compulsive disorders, opioid-induced respiratory depression, pathological gambling, schizophrenia, tardive dyskinesia, tics with Tourette's syndrome, and behavioral problems with Tourette's syndrome.

8. The method of claim 1, wherein the condition is selected from anxiety disorders, attention-deficit hyperactivity disorder, depression, brain damage, glaucoma, tardive dyskinesia, cholestatic pruritis, tics with Tourette's syndrome, and behavioral problems with Tourette's syndrome.

9. The method of claim 1, wherein the condition is selected from aggression, anxiety, bipolar disorder, depression, drug-seeking behavior, hypertension, migraines, opioid-induced respiratory depression, and schizophrenia.

10. The method of claim 1, wherein the condition is selected from anxiety, depression, aggression, and impulsivity.

11. The method of claim 1, wherein the condition is selected from facial erythema associated with rosacea, nasal congestion, and sinus congestion.

12. The method of claim 1, wherein the condition is selected from cocaine abuse, pathological gambling, obsessive-compulsive disorder, and schizophrenia.

13. The method of claim 1, wherein the condition is obsessive-compulsive disorder.

14. The method of claim 1, wherein the condition is hyperactive bladder or depression.

15. The method of claim 1, wherein pentadecanoylcarnitine or a pharmaceutically acceptable salt thereof is administered as a dietary supplement.

16. The method of claim 1, wherein pentadecanoylcarnitine or a pharmaceutically acceptable salt thereof is administered in a unit dosage form.

17. The method of claim 1, wherein pentadecanoylcarnitine or a pharmaceutically acceptable salt thereof is administered in a tablet, a capsule, an encapsulated pill, a gelcap pill, a dispensable form of an oral or injectable liquid suspension or solution, a spray, an aerosol, powder, or granules.

18. The method of claim 1, wherein pentadecanoylcarnitine or a pharmaceutically acceptable salt thereof is isolated from natural sources, semi-synthetic, synthetic, or any mixture thereof.

19. A method of supporting appetite, memory, mood, renal health, sexuality, sociability, or weight loss, the method comprising:
administering to a subject in need thereof, an effective amount of pentadecanoylcarnitine or a pharmaceutically acceptable salt or solvate thereof.

20. The method of claim 19, wherein a body concentration of pentadecanoylcarnitine of from 1 µM to 20 µM is achieved in the subject.

21. The method of claim 19, wherein pentadecanoylcarnitine or a pharmaceutically acceptable salt thereof is administered.

22. The method of claim 19, wherein from 0.1 mg to 50 mg, per 1 kg of body weight, of the pentadecanoylcarnitine or a pharmaceutically acceptable salt or solvate thereof is administered.

23. The method of claim 19, wherein pentadecanoylcarnitine or a pharmaceutically acceptable salt or solvate thereof is administered once per day.

24. The method of claim 19, wherein pentadecanoylcarnitine or or pharmaceutically acceptable salts, solvates, or stereoisomers thereof is in a unit dosage form comprising from 0.01 mg to 10000 mg, of the pentadecanoylcarnitine or pharmaceutically acceptable salts, solvates, stereoisomers, or esters thereof.

25. The method of claim 19, wherein the method supports appetite, mood, renal health, sexuality, or sociability.

26. The method of claim 19, wherein the method supports appetite, sexuality, or sociability.

27. The method of claim 19, wherein pentadecanoylcarnitine or a pharmaceutically acceptable salt thereof is administered as a dietary supplement.

28. The method of claim 19, wherein pentadecanoylcarnitine or a pharmaceutically acceptable salt thereof is administered in a unit dosage form.

29. The method of claim 19, wherein pentadecanoylcarnitine or a pharmaceutically acceptable salt thereof is administered in a tablet, a capsule, an encapsulated pill, a gelcap pill, a dispensable form of an oral or injectable liquid suspension or solution, a spray, an aerosol, powder, or granules.

30. The method of claim 19, wherein pentadecanoylcarnitine or a pharmaceutically acceptable salt thereof is isolated from natural sources, semi-synthetic, synthetic, or any mixture thereof.

* * * * *